United States Patent
Dai et al.

(10) Patent No.: US 9,814,620 B2
(45) Date of Patent: *Nov. 14, 2017

(54) SYSTEMS AND METHODS FOR TREATMENT DECONVOLUTION USING MULTI-SCALE KERNELS

(71) Applicant: AMO Development, LLC, Santa Ana, CA (US)

(72) Inventors: Guang-Ming Dai, Fremont, CA (US);
Anatoly Fabrikant, Fremont, CA (US);
Dimitri Chernyak, Sunnyvale, CA (US)

(73) Assignee: AMO Development, LLC, Santa Ana, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/294,056

(22) Filed: Oct. 14, 2016

(65) Prior Publication Data

US 2017/0049622 A1    Feb. 23, 2017

Related U.S. Application Data

(63) Continuation of application No. 14/523,467, filed on Oct. 24, 2014, now Pat. No. 9,498,117, which is a
(Continued)

(51) Int. Cl.
*G06K 9/00* (2006.01)
*A61F 9/008* (2006.01)
(Continued)

(52) U.S. Cl.
CPC ........ *A61F 9/00806* (2013.01); *A61B 3/0025* (2013.01); *A61B 3/028* (2013.01);
(Continued)

(58) Field of Classification Search
CPC ................ G06K 9/00; A61B 3/00; A61F 9/00
(Continued)

(56) References Cited

U.S. PATENT DOCUMENTS

| | | | | |
|---|---|---|---|---|
| 5,891,132 A | * | 4/1999 | Hohla | ................. A61F 9/00804 606/10 |
| 6,090,100 A | * | 7/2000 | Hohla | ..................... A61F 9/008 606/10 |

(Continued)

OTHER PUBLICATIONS

Durrie, et al; "Femtosecond laser versus mechanical keratome flaps in wavefront-guided laser in situ keratomileusis: Prospective contralateral eye study"; *Journal of Cataract and Refractive Surgery*, vol. 31, No. 1; (2005); pp. 120-126.
(Continued)

*Primary Examiner* — Abolfazl Tabatabai
(74) *Attorney, Agent, or Firm* — Abbott Medical Optics Inc.

(57) ABSTRACT

Deconvolution systems and methods based on cornea smoothing can be used to obtain an ablation target or treatment shape that does not induce significant high order aberrations such as spherical aberration. Exemplary ablation targets or treatment shapes can provide a post-operative spherical aberration that is equal to or below a naturally occurring amount of spherical aberration.

23 Claims, 53 Drawing Sheets

Related U.S. Application Data continuation of application No. 14/453,068, filed on Aug. 6, 2014, now abandoned.

(60) Provisional application No. 61/871,120, filed on Aug. 28, 2013.

(51) Int. Cl.
*A61B 3/028* (2006.01)
*A61B 3/00* (2006.01)
*A61B 34/10* (2016.01)
*G06F 19/00* (2011.01)
*G06T 5/00* (2006.01)
*G06G 7/48* (2006.01)

(52) U.S. Cl.
CPC .......... *A61B 34/10* (2016.02); *G06F 19/3437* (2013.01); *G06T 5/003* (2013.01); *A61B 2034/104* (2016.02); *A61F 2009/0088* (2013.01); *A61F 2009/00848* (2013.01); *A61F 2009/00872* (2013.01); *G06T 2207/30041* (2013.01)

(58) Field of Classification Search
USPC ......... 382/128, 129, 130, 131, 12, 133, 134, 382/132; 606/4, 5, 10, 204.25; 703/11
See application file for complete search history.

(56) References Cited

U.S. PATENT DOCUMENTS

| | | | |
|---|---|---|---|
| 7,044,602 B2 | 5/2006 | Chernyak | |
| 7,926,490 B2* | 4/2011 | Dai | A61F 9/008 128/898 |
| 9,498,117 B2* | 11/2016 | Dai | A61B 3/028 |
| 2013/0190736 A1 | 7/2013 | Fabrikant et al. | |
| 2014/0095137 A1 | 4/2014 | Dai et al. | |

OTHER PUBLICATIONS

Pallikaris, et al.; "Induced optical aberrations following formation of a laser in situ keratomileusis flap"; *Journal of Cataract and Refractive Surgery*, vol. 28 (2002); pp. 1737-1741.

Porter, et al.; "Separate Effects of the Microkeratome Incision and Laser Ablation on the Eye's Wave Aberration"; *American Journal of Ophthalmology*, vol. 136, No. 2 (2003); pp. 327-337.

Tran, et al.; "Randomized prospective clinical study comparing induced aberrations with IntraLase and Hansatome flap creation in fellow eyes: Potential impact on wavefront-guided laser in situ kertomileusis"; *Journal of Cataract and Refractive Surgery*, vol. 31 (2005); pp. 97-105.

* cited by examiner

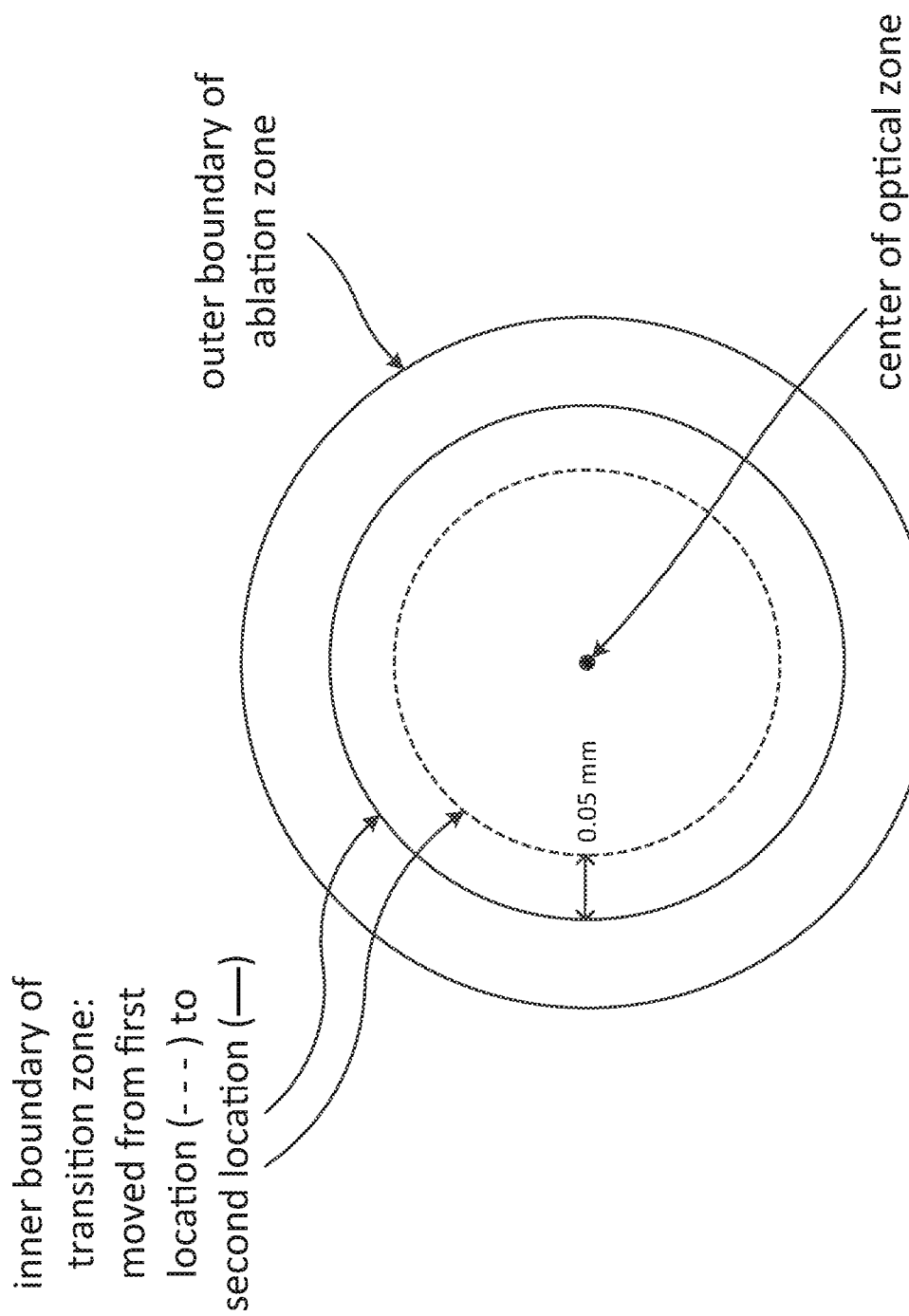

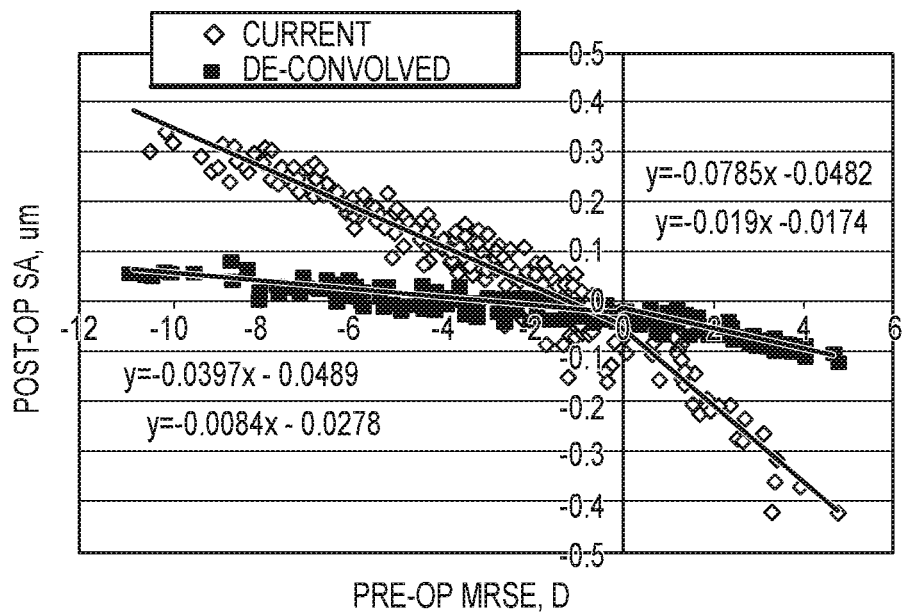
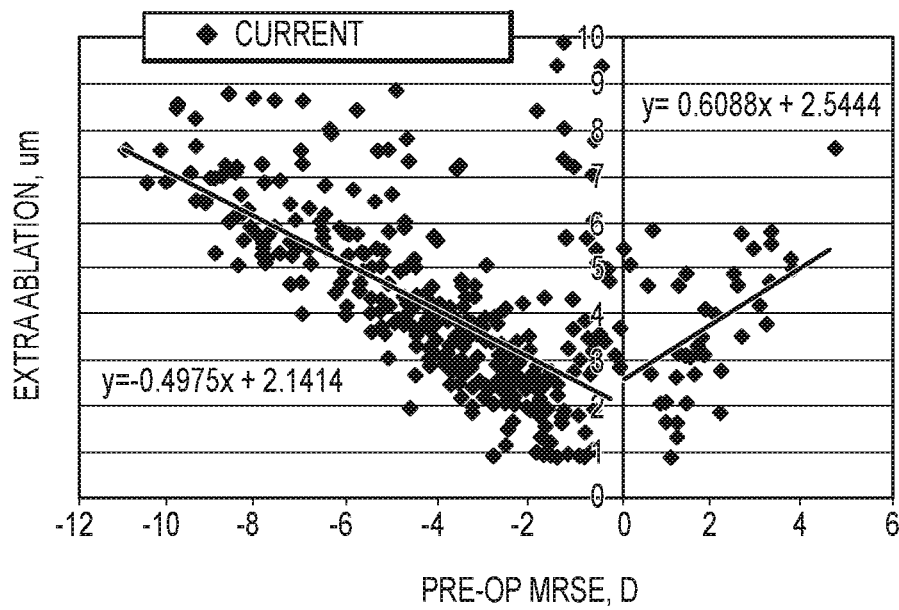
FIG.23

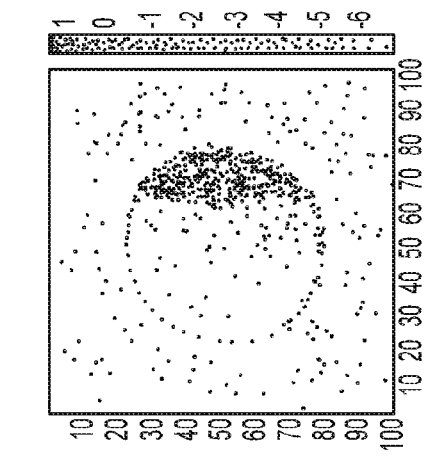
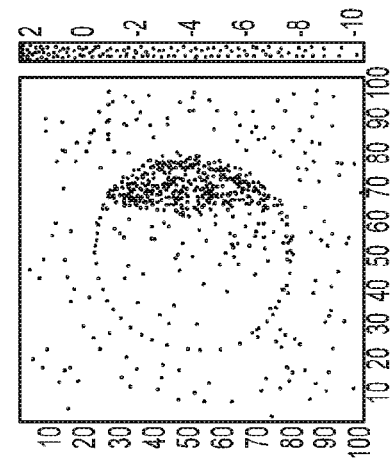
FIG. 32A
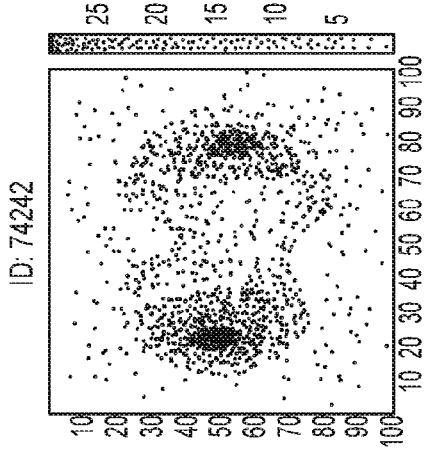
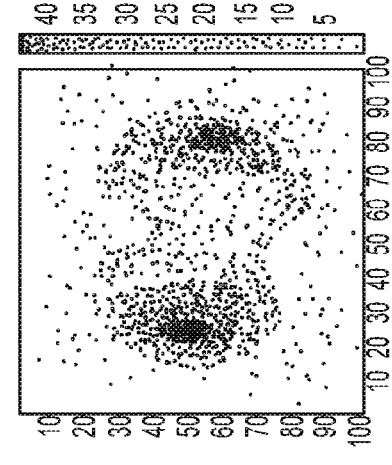
FIG. 32B
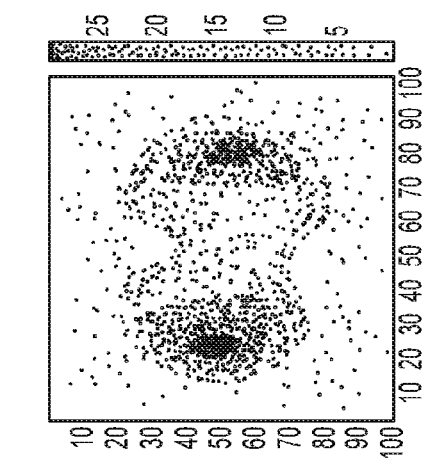
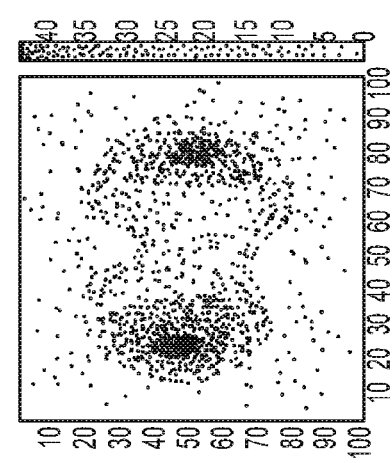

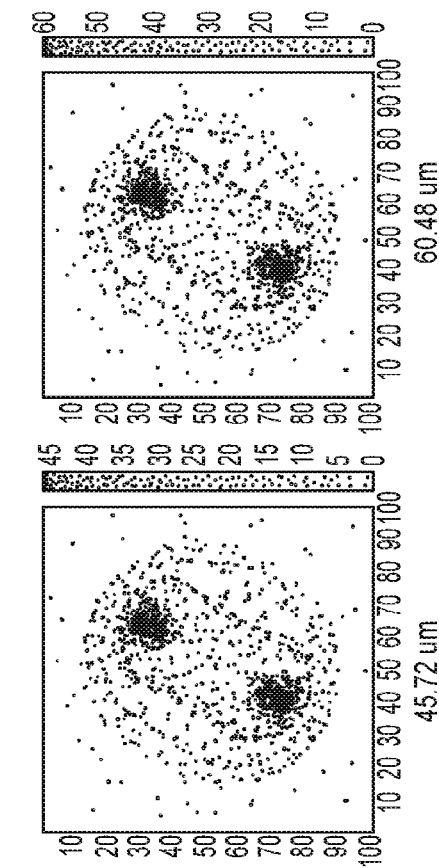
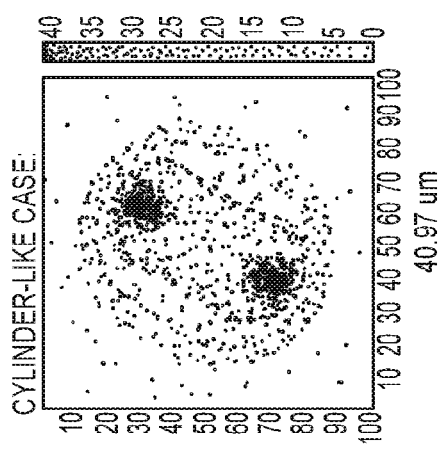
FIG. 35A
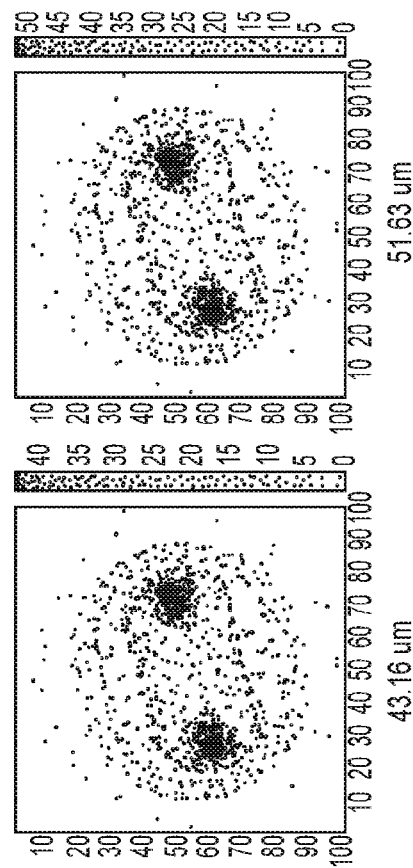
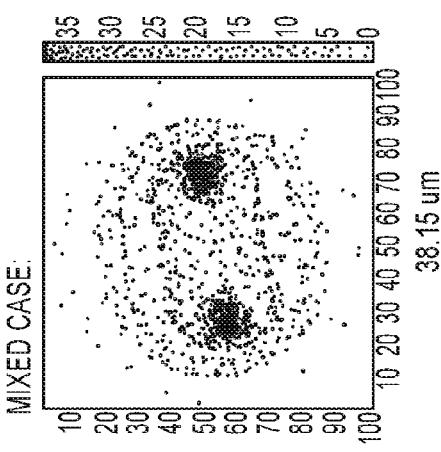
FIG. 35B

SYSTEMS AND METHODS FOR TREATMENT DECONVOLUTION USING MULTI-SCALE KERNELS

CROSS-REFERENCES TO RELATED APPLICATIONS

This application is a continuation of U.S. Non provisional application Ser. No. 14/523,467, filed on Oct. 24, 2014, which is a continuation of U.S. Non provisional application Ser. No. 14/453,068, filed on Aug. 6, 2014, which claims the benefit of priority to U.S. Provisional Application No. 61/871,120, filed Aug. 28, 2013. This application is related to U.S. Patent Application No. 61/708,815 filed Oct. 2, 2012. This application is also related to U.S. Pat. No. 7,926,490 issued Apr. 19, 2011, and U.S. patent application Ser. No. 13/554,276, filed Jul. 20, 2012. The entire content of each of the above filings is hereby incorporated by reference for all purposes.

BACKGROUND OF THE INVENTION

Embodiments of the present invention related to the field of vision treatment, and in particular to systems and methods for generating or modifying optical treatment shapes.

The post-operative induction of high-order aberrations (HOAs), especially spherical aberration (SA), remains an important issue for laser vision correction technology.

It has been found that post-operative cornea remodeling is a significant root cause of SA induction. One main effect of the cornea remodeling involves the smoothing of epithelium at the anterior surface of the eye, where the epithelium tends to grow thicker and fill in the dips of the cornea surface as created by refractive surgery. Epithelial smoothing can result in regression following refractive surgery, and sometimes leads to induced high-order aberrations that are particularly strong for high myopia and hyperopia cases.

Certain techniques have been proposed for minimizing induced post-operative SA, including linear adjustment of the basis data and nomogram adjustments. Although such techniques can provide benefits to patients in need thereof, further improvements would be desirable. Embodiments of the present invention provide solutions to address these and other outstanding needs.

BRIEF SUMMARY OF THE INVENTION

It has been discovered that deconvolution techniques based on a cornea smoothing model can be used to obtain an ablation target or treatment shape that induces little or no post-operative SA. In some instances, these ablation targets or treatment shapes can provide a post-operative SA that is equal to or below a naturally occurring amount of SA.

Hence, embodiments of the present invention encompass systems and methods for obtaining a modified ablation target that is capable of eliminating, reducing, or minimizing a systematic trend in post-operatively induced spherical aberration. In some cases, the modification of the target shape introduces only a small increase in the required depth for the ablation. Hence, such techniques are helpful in providing safe and effective treatments. In some cases, the modification of the target shape may change the peripheral cornea profile, which can affect the SA without changing the central refractive power.

In some instances, embodiments encompass techniques for determining a vision treatment for an eye of a patient, which may include obtaining an original target profile for the eye of the patient, obtaining a spatial domain kernel filter (e.g. based on an inverse Fourier transform of a Fourier domain noise filter), convolving the original target profile with the spatial domain kernel filter, and determining the vision treatment based on the convolved profile.

Embodiments of the present invention can be readily adapted for use with existing laser systems and other optical treatment devices. Although system, software, and method embodiments of the present invention are described primarily in the context of a laser eye surgery system, it should be understood that embodiments of the present invention may be adapted for use in or in combination with alternative eye treatment procedures, systems, or modalities, such as spectacle lenses, intraocular lenses, accommodating IOLs, contact lenses, corneal ring implants, collagenous corneal tissue thermal remodeling, corneal inlays, corneal onlays, other corneal implants or grafts, and the like. Relatedly, systems, software, and methods according to embodiments of the present invention are well suited for customizing any of these treatment modalities to a specific patient. Thus, for example, embodiments encompass custom preformed lenses, intraocular lenses, custom contact lenses, custom corneal implants, and the like, which can be configured to treat or ameliorate any of a variety of vision conditions in a particular patient based on their unique ocular characteristics or anatomy. Additionally, the modified ablation target or target shape may be implemented via other non-ablative laser therapies, such as laser-incised custom lenticule shapes and subsequent extraction and laser-based corneal incision patterns.

In some instances, these techniques can be carried out in conjunction with treatments provided by any of a variety of laser devices, including without limitation the WaveScan® System and the STAR S4® Excimer Laser System both by Abbott Medical Optics Inc., the WaveLight® Allegretto Wave® Eye-Q laser, the Schwind Amaris™ lasers, the 217P excimer workstation by Technolas PerfectVision GmbH, the Mel 80™ laser by Carl Zeiss Meditec, Inc., and the like.

In one aspect, embodiments of the present invention encompass systems and methods for determining a vision treatment for an eye of a patient. Exemplary techniques may include, for example, receiving, at an input, an original target profile for the eye of the patient, and convolving the original target profile with the spatial domain kernel filter. The spatial domain kernel filter can be based on an inverse Fourier transform of a Fourier domain noise filter. Techniques may also include determining the vision treatment based on the convolved profile. Optionally, techniques may include administering the treatment to the patient. In some instances, the Fourier domain noise filter is based on a conjugate of a Fourier domain complex matrix. In some instances, the Fourier domain noise filter is based on a modulus of a Fourier domain complex matrix. In some instances, the Fourier domain noise filter is based on a conjugate of a Fourier domain complex matrix and a modulus of the Fourier domain complex matrix. According to some embodiments, the Fourier domain noise filter is characterized by fraction having a numerator comprising a conjugate of a Fourier domain complex matrix and a denominator comprising a modulus of the Fourier domain complex matrix. In some cases, the Fourier domain complex matrix is characterized by the formula $$K(k_x, k_y) = \frac{1}{1 + \frac{\sigma^2(k_x^2 + k_y^2)}{(0.5 \, dL)^2}}$$

where σ represents a diffusion coefficient, $k_x$ and $k_y$ represent frequency domain variables, and dL represents a mesh size. In some cases, σ has a value of 0.35 mm and dL has a value of 0.1 mm. Optionally, σ may have a value within a range from about 0.2 mm to about 0.5 mm. In some cases, σ may have a value within a range from about 0.33 mm to about 0.4 mm. Optionally, the denominator can be characterized by the expression $|K(k_x, k_y)|^n$, where n is an integer having a value of 2 or more. In some instances, the denominator can be characterized by the expression $[|K(k_x, k_y)|^n + SNR^2]$ where n is an integer having a value of 2 or more and SNR represents a signal to noise ratio value. In some instances, the convolved profile includes a transition zone radius, and a method may further include zeroing the convolved profile at locations outside of the transition zone radius. In some instances, the original target profile may include an original refractive spherical equivalent value within a 4 mm diameter area, and the convolved target profile may include a target refractive spherical equivalent value within a 4 mm diameter area. Optionally, the method may further include scaling the original refractive spherical equivalent with the target refractive spherical equivalent value. Some methods may also include elevating the convolved profile so that a lowest point on the convolved profile is zero or greater. In some instances, a convolved profile includes a transition zone radius, and methods may include applying a damping multiplier at or near the transition zone radius. In some instances, the target shape includes an optical zone having a periphery, and the convolution effects a change in the target shape near the periphery of the optical zone.

In another aspect, embodiments of the present invention encompass systems for determining a vision treatment for an eye of a patient. Exemplary systems may include an input that receives an original target profile for the eye of the patient, and a convolution module that convolves the original target profile with a spatial domain kernel filter. The spatial domain kernel filter can be based on an inverse Fourier transform of a Fourier domain noise filter. Systems may also include a treatment generation or determination module that determines the vision treatment based on the convolved profile. Optionally, systems can include a treatment delivery module that delivers the treatment to the patient. In some instances, the Fourier domain noise filter is based on a conjugate of a Fourier domain complex matrix. In some instances, the Fourier domain noise filter is based on a modulus of a Fourier domain complex matrix. In some instances, the Fourier domain noise filter is based on a conjugate of a Fourier domain complex matrix and a modulus of the Fourier domain complex matrix. According to some embodiments, the Fourier domain noise filter is characterized by fraction having a numerator comprising a conjugate of a Fourier domain complex matrix and a denominator comprising a modulus of the Fourier domain complex matrix. In some cases, the Fourier domain complex matrix is characterized by the formula $$K(k_x, k_y) = \frac{1}{1 + \frac{\sigma^2(k_x^2 + k_y^2)}{(0.5 \, dL)^2}}$$

where σ represents a diffusion coefficient, $k_x$ and $k_y$ represent frequency domain variables, and dL represents a mesh size. In some cases, σ has a value of 0.35 mm and dL has a value of 0.1 mm. Optionally, σ may have a value within a range from about 0.2 mm to about 0.5 mm. In some cases, σ may have a value within a range from about 0.33 mm to about 0.4 mm. Optionally, the denominator can be characterized by the expression $|K(k_x, k_y)|^n$, where n is an integer having a value of 2 or more. In some instances, the denominator can be characterized by the expression $[|K(k_x, k_y)|^n + SNR^2]$ where n is an integer having a value of 2 or more and SNR represents a signal to noise ratio value. In some instances, the convolved profile includes a transition zone radius, and the convolution module can zero the convolved profile at locations outside of the transition zone radius. In some instances, the original target profile may include an original refractive spherical equivalent value within a 4 mm diameter area, and the convolved target profile may include a target refractive spherical equivalent value within a 4 mm diameter area. Optionally, the convolution module can scale the original refractive spherical equivalent with the target refractive spherical equivalent value. In some cases, the convolution module can elevate the convolved profile so that a lowest point on the convolved profile is zero or greater. In some instances, a convolved profile includes a transition zone radius, and the convolution module can apply a damping multiplier at or near the transition zone radius. In some instances, the target shape includes an optical zone having a periphery, and the convolution module can effect a change in the target shape near the periphery of the optical zone.

In still another aspect, embodiments of the present invention encompass computer program products for determining a vision treatment for an eye of a patient. An exemplary computer program product may be embodied on a non-transitory tangible computer readable medium, and may include computer code for receiving an original target profile for the eye of the patient, computer code for convolving the original target profile with a spatial domain kernel filter, and computer code for determining the vision treatment based on the convolved profile. The spatial domain kernel filter may be based on an inverse Fourier transform of a Fourier domain noise filter. Optionally, computer program products may include computer code for delivering or administering the treatment to the patient. In some instances, the Fourier domain noise filter is based on a conjugate of a Fourier domain complex matrix. In some instances, the Fourier domain noise filter is based on a modulus of a Fourier domain complex matrix. In some instances, the Fourier domain noise filter is based on a conjugate of a Fourier domain complex matrix and a modulus of the Fourier domain complex matrix. According to some embodiments, the Fourier domain noise filter is characterized by fraction having a numerator comprising a conjugate of a Fourier domain complex matrix and a denominator comprising a modulus of the Fourier domain complex matrix. In some cases, the Fourier domain complex matrix is characterized by the formula $$K(k_x, k_y) = \frac{1}{1 + \frac{\sigma^2(k_x^2 + k_y^2)}{(0.5 \, dL)^2}}$$

where σ represents a diffusion coefficient, $k_x$ and $k_y$ represent frequency domain variables, and dL represents a mesh size. In some cases, σ has a value of 0.35 mm and dL has a value of 0.1 mm. Optionally, σ may have a value within a range from about 0.2 mm to about 0.5 mm. In some cases, σ may have a value within a range from about 0.33 mm to about 0.4 mm. Optionally, the denominator can be characterized by the expression $|K(k_x, k_y)|^n$, where n is an integer having a value of 2 or more. In some instances, the denominator can be characterized by the expression $[|K(k_x, k_y)|^n + SNR^2]$ where n is an integer having a value of 2 or more and SNR represents a signal to noise ratio value. In some instances, the convolved profile includes a transition zone radius, and the computer code for convolving can include computer code for zeroing the convolved profile at locations outside of the transition zone radius. In some instances, the original target profile may include an original refractive spherical equivalent value within a 4 mm diameter area, and the convolved target profile may include a target refractive spherical equivalent value within a 4 mm diameter area. Optionally, the computer code for convolving can include computer code for scaling the original refractive spherical equivalent with the target refractive spherical equivalent value. In some cases, the computer code for convolving can include computer code for elevating the convolved profile so that a lowest point on the convolved profile is zero or greater. In some instances, a convolved profile includes a transition zone radius, and the computer code for convolving can include computer code for applying a damping multiplier at or near the transition zone radius. In some instances, the target shape includes an optical zone having a periphery, and the computer code for convolving can include computer code for effecting a change in the target shape near the periphery of the optical zone.

For a fuller understanding of the nature and advantages of the present invention, reference should be had to the ensuing detailed description taken in conjunction with the accompanying drawings.

BRIEF DESCRIPTION OF THE DRAWINGS

FIG. 6A shows post-operative values and FIG. 6B shows aspects of optical and transition zones according to embodiments of the present invention.

FIG. 23 illustrates aspects of deconvolution effects according to embodiments of the present invention.

FIGS. 32A-32C depict aspects of expected and inversed convolved targets according to embodiments of the present invention.

FIGS. 35A-35C show aspects of vision condition cases according to embodiments of the present invention.

DETAILED DESCRIPTION OF THE INVENTION

Embodiments of the present invention can be readily adapted for use with existing laser systems, wavefront measurement systems, and other optical measurement devices. While the systems, software, and methods of the present invention are described primarily in the context of a laser eye surgery system, it should be understood the present invention may be adapted for use in alternative eye treatment procedures and systems such as spectacle lenses, intraocular lenses, contact lenses, corneal ring implants, collagenous corneal tissue thermal remodeling, and the like.

Figure 1:
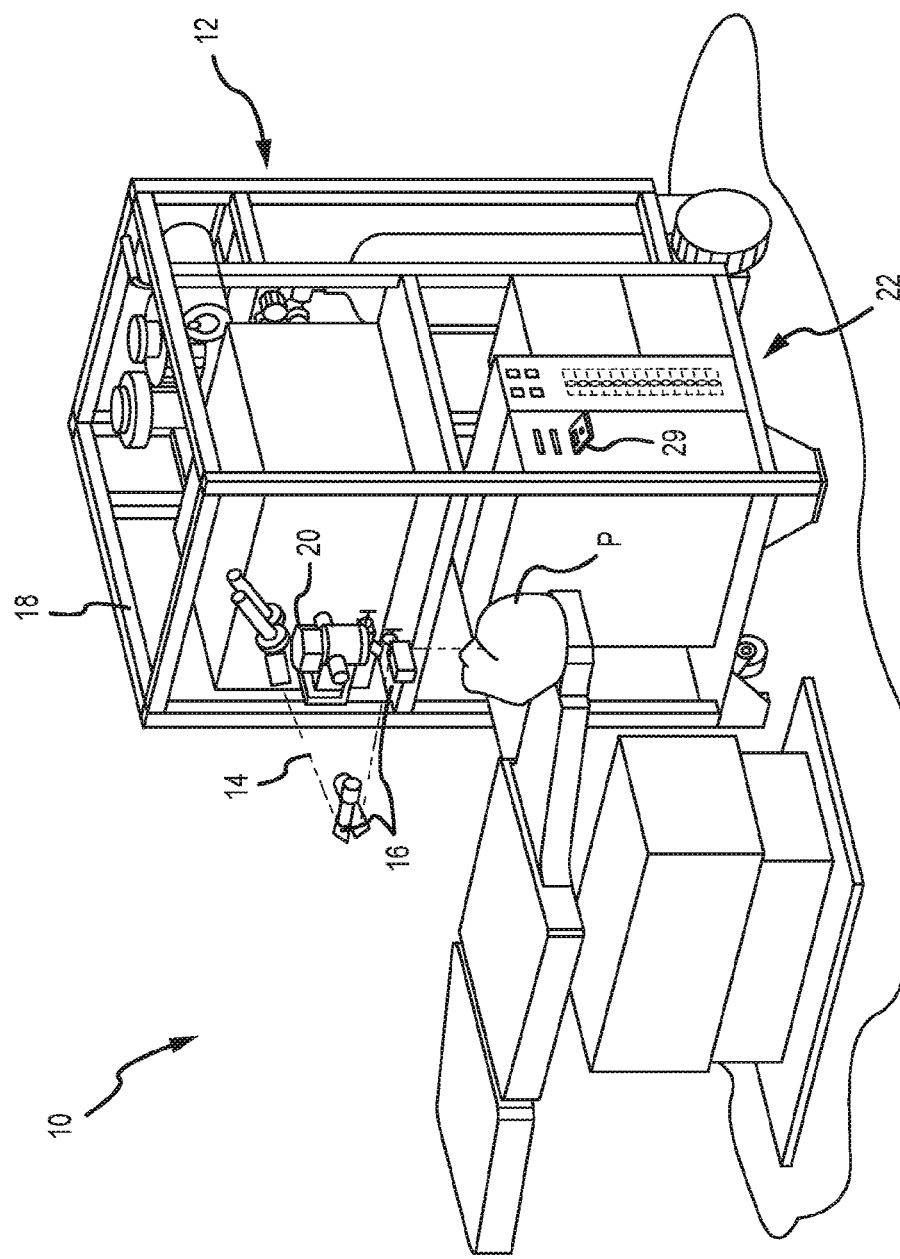
FIG. 1 illustrates a laser ablation system according to an embodiment of the present invention.

Turning now to the drawings, FIG. 1 illustrates a laser eye surgery system 10 of the present invention, including a laser 12 that produces a laser beam 14. Laser 12 is optically coupled to laser delivery optics 16, which directs laser beam 14 to an eye E of patient P. A delivery optics support structure (not shown here for clarity) extends from a frame 18 supporting laser 12. A microscope 20 is mounted on the delivery optics support structure, the microscope often being used to image a cornea of eye E.

Laser 12 generally comprises an excimer laser, ideally comprising an argon-fluorine laser producing pulses of laser light having a wavelength of approximately 193 nm. Laser 12 will preferably be designed to provide a feedback stabilized fluence at the patient's eye, delivered via delivery optics 16. The present invention may also be useful with alternative sources of ultraviolet or infrared radiation, particularly those adapted to controllably ablate the corneal tissue without causing significant damage to adjacent and/or underlying tissues of the eye. Such sources include, but are not limited to, solid state lasers and other devices which can generate energy in the ultraviolet wavelength between about 185 and 205 nm and/or those which utilize frequency-multiplying techniques. Hence, although an excimer laser is the illustrative source of an ablating beam, other lasers may be used in the present invention.

Laser system 10 will generally include a computer or programmable processor 22. Processor 22 may comprise (or interface with) a conventional PC system including the standard user interface devices such as a keyboard, a display monitor, and the like. Processor 22 will typically include an input device such as a magnetic or optical disk drive, an internet connection, or the like. Such input devices will often be used to download a computer executable code from a tangible storage media 29 embodying any of the methods of the present invention. Tangible storage media 29 may take the form of a floppy disk, an optical disk, a data tape, a volatile or non-volatile memory, RAM, or the like, and the processor 22 will include the memory boards and other standard components of modern computer systems for storing and executing this code. Tangible storage media 29 may optionally embody wavefront sensor data, wavefront gradients, a wavefront elevation map, a treatment map, a corneal elevation map, and/or an ablation table. While tangible storage media 29 will often be used directly in cooperation with a input device of processor 22, the storage media may also be remotely operatively coupled with processor by means of network connections such as the internet, and by wireless methods such as infrared, Bluetooth, or the like.

Laser 12 and delivery optics 16 will generally direct laser beam 14 to the eye of patient P under the direction of a computer 22. Computer 22 will often selectively adjust laser beam 14 to expose portions of the cornea to the pulses of laser energy so as to effect a predetermined sculpting of the cornea and alter the refractive characteristics of the eye. In many embodiments, both laser beam 14 and the laser delivery optical system 16 will be under computer control of processor 22 to effect the desired laser sculpting process, with the processor effecting (and optionally modifying) the pattern of laser pulses. The pattern of pulses may by summarized in machine readable data of tangible storage media 29 in the form of a treatment table, and the treatment table may be adjusted according to feedback input into processor 22 from an automated image analysis system in response to feedback data provided from an ablation monitoring system feedback system. Optionally, the feedback may be manually entered into the processor by a system operator. Such feedback might be provided by integrating the wavefront measurement system described below with the laser treatment system 10, and processor 22 may continue and/or terminate a sculpting treatment in response to the feedback, and may optionally also modify the planned sculpting based at least in part on the feedback. Measurement systems are further described in U.S. Pat. No. 6,315,413, the full disclosure of which is incorporated herein by reference.

Laser beam 14 may be adjusted to produce the desired sculpting using a variety of alternative mechanisms. The laser beam 14 may be selectively limited using one or more variable apertures. An exemplary variable aperture system having a variable iris and a variable width slit is described in U.S. Pat. No. 5,713,892, the full disclosure of which is incorporated herein by reference. The laser beam may also be tailored by varying the size and offset of the laser spot from an axis of the eye, as described in U.S. Pat. Nos. 5,683,379, 6,203,539, and 6,331,177, the full disclosures of which are incorporated herein by reference.

Still further alternatives are possible, including scanning of the laser beam over the surface of the eye and controlling the number of pulses and/or dwell time at each location, as described, for example, by U.S. Pat. No. 4,665,913, the full disclosure of which is incorporated herein by reference; using masks in the optical path of laser beam 14 which ablate to vary the profile of the beam incident on the cornea, as described in U.S. Pat. No. 5,807,379, the full disclosure of which is incorporated herein by reference; hybrid profile-scanning systems in which a variable size beam (typically controlled by a variable width slit and/or variable diameter iris diaphragm) is scanned across the cornea; or the like. The computer programs and control methodology for these laser pattern tailoring techniques are well described in the patent literature.

Additional components and subsystems may be included with laser system 10, as should be understood by those of skill in the art. For example, spatial and/or temporal integrators may be included to control the distribution of energy within the laser beam, as described in U.S. Pat. No. 5,646,791, the full disclosure of which is incorporated herein by reference. Ablation effluent evacuators/filters, aspirators, and other ancillary components of the laser surgery system are known in the art. Further details of suitable systems for performing a laser ablation procedure can be found in commonly assigned U.S. Pat. Nos. 4,665,913, 4,669,466, 4,732,148, 4,770,172, 4,773,414, 5,207,668, 5,108,388, 5,219,343, 5,646,791 and 5,163,934, the complete disclosures of which are incorporated herein by reference. Suitable systems also include commercially available refractive laser systems such as those manufactured and/or sold by Alcon, Bausch & Lomb, Nidek, WaveLight, LaserSight, Schwind, Zeiss-Meditec, and the like. Basis data can be further characterized for particular lasers or operating conditions, by taking into account localized environmental variables such as temperature, humidity, airflow, and aspiration.

Figure 2:
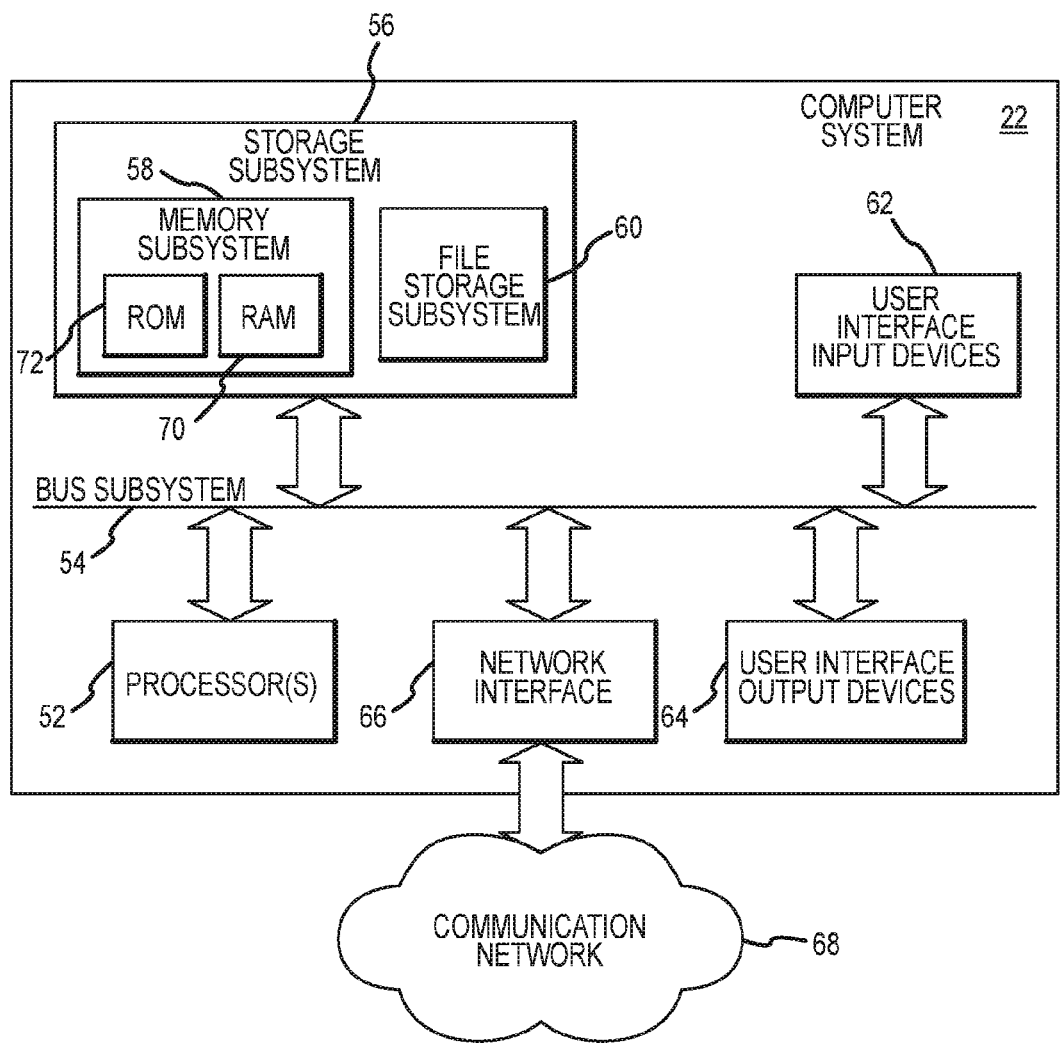
FIG. 2 illustrates a simplified computer system according to an embodiment of the present invention.

FIG. 2 is a simplified block diagram of an exemplary computer system 22 that may be used by the laser surgical system 10 of the present invention. Computer system 22 typically includes at least one processor 52 which may communicate with a number of peripheral devices via a bus subsystem 54. These peripheral devices may include a storage subsystem 56, comprising a memory subsystem 58 and a file storage subsystem 60, user interface input devices 62, user interface output devices 64, and a network interface subsystem 66. Network interface subsystem 66 provides an interface to outside networks 68 and/or other devices, such as the wavefront measurement system 30.

User interface input devices 62 may include a keyboard, pointing devices such as a mouse, trackball, touch pad, or graphics tablet, a scanner, foot pedals, a joystick, a touchscreen incorporated into the display, audio input devices such as voice recognition systems, microphones, and other types of input devices. User input devices 62 will often be used to download a computer executable code from a tangible storage media 29 embodying any of the methods of the present invention. In general, use of the term "input device" is intended to include a variety of conventional and proprietary devices and ways to input information into computer system 22.

User interface output devices 64 may include a display subsystem, a printer, a fax machine, or non-visual displays such as audio output devices. The display subsystem may be a cathode ray tube (CRT), a flat-panel device such as a liquid crystal display (LCD), a projection device, or the like. The display subsystem may also provide a non-visual display such as via audio output devices. In general, use of the term "output device" is intended to include a variety of conventional and proprietary devices and ways to output information from computer system 22 to a user.

Storage subsystem 56 can store the basic programming and data constructs that provide the functionality of the various embodiments of the present invention. For example, a database and modules implementing the functionality of the methods of the present invention, as described herein, may be stored in storage subsystem 56. These software modules are generally executed by processor 52. In a distributed environment, the software modules may be stored on a plurality of computer systems and executed by processors of the plurality of computer systems. Storage subsystem 56 typically comprises memory subsystem 58 and file storage subsystem 60.

Memory subsystem 58 typically includes a number of memories including a main random access memory (RAM) 70 for storage of instructions and data during program execution and a read only memory (ROM) 72 in which fixed instructions are stored. File storage subsystem 60 provides persistent (non-volatile) storage for program and data files, and may include tangible storage media 29 (FIG. 1) which may optionally embody wavefront sensor data, wavefront gradients, a wavefront elevation map, a treatment map, and/or an ablation table. File storage subsystem 60 may include a hard disk drive, a floppy disk drive along with associated removable media, a Compact Digital Read Only Memory (CD-ROM) drive, an optical drive, DVD, CD-R, CD-RW, solid-state removable memory, and/or other removable media cartridges or disks. One or more of the drives may be located at remote locations on other connected computers at other sites coupled to computer system 22. The modules implementing the functionality of the present invention may be stored by file storage subsystem 60.

Bus subsystem 54 provides a mechanism for letting the various components and subsystems of computer system 22 communicate with each other as intended. The various subsystems and components of computer system 22 need not be at the same physical location but may be distributed at various locations within a distributed network. Although bus subsystem 54 is shown schematically as a single bus, alternate embodiments of the bus subsystem may utilize multiple busses.

Computer system 22 itself can be of varying types including a personal computer, a portable computer, a workstation, a computer terminal, a network computer, a control system in a wavefront measurement system or laser surgical system, a mainframe, or any other data processing system. Due to the ever-changing nature of computers and networks, the description of computer system 22 depicted in FIG. 2 is intended only as a specific example for purposes of illustrating one embodiment of the present invention. Many other configurations of computer system 22 are possible having more or less components than the computer system depicted in FIG. 2.

Figure 3:
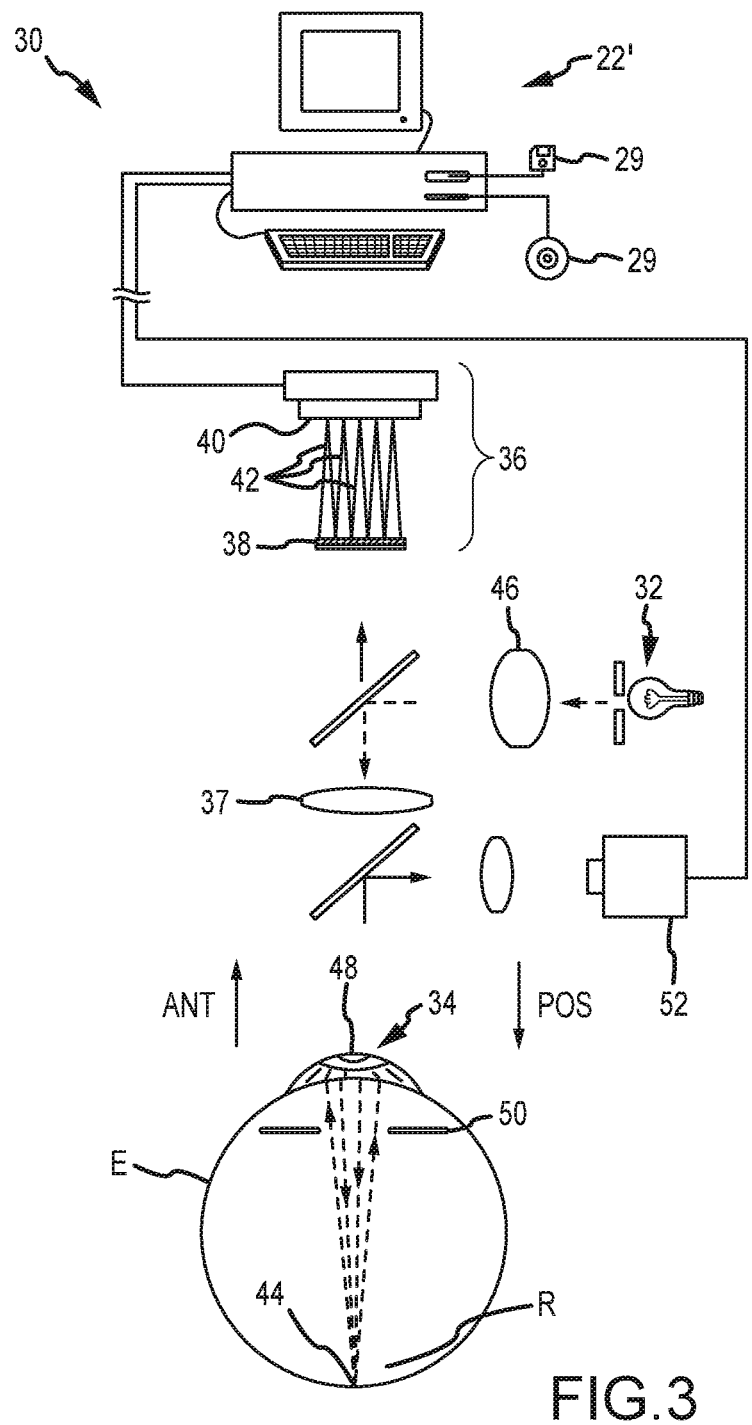
FIG. 3 illustrates a wavefront measurement system according to an embodiment of the present invention.

Referring now to FIG. 3, one embodiment of a wavefront measurement system 30 is schematically illustrated in simplified form. In very general terms, wavefront measurement system 30 is configured to sense local slopes of a gradient map exiting the patient's eye. Devices based on the Hartmann-Shack principle generally include a lenslet array to sample the gradient map uniformly over an aperture, which is typically the exit pupil of the eye. Thereafter, the local slopes of the gradient map are analyzed so as to reconstruct the wavefront surface or map.

More specifically, one wavefront measurement system 30 includes an image source 32, such as a laser, which projects a source image through optical tissues 34 of eye E so as to form an image 44 upon a surface of retina R. The image from retina R is transmitted by the optical system of the eye (e.g., optical tissues 34) and imaged onto a wavefront sensor 36 by system optics 37. The wavefront sensor 36 communicates signals to a computer system 22' for measurement of the optical errors in the optical tissues 34 and/or determination of an optical tissue ablation treatment program. Computer 22' may include the same or similar hardware as the computer system 22 illustrated in FIGS. 1 and 2. Computer system 22' may be in communication with computer system 22 that directs the laser surgery system 10, or some or all of the components of computer system 22, 22' of the wavefront measurement system 30 and laser surgery system 10 may be combined or separate. If desired, data from wavefront sensor 36 may be transmitted to a laser computer system 22 via tangible media 29, via an I/O port, via an networking connection 66 such as an intranet or the Internet, or the like.

Wavefront sensor 36 generally comprises a lenslet array 38 and an image sensor 40. As the image from retina R is transmitted through optical tissues 34 and imaged onto a surface of image sensor 40 and an image of the eye pupil P is similarly imaged onto a surface of lenslet array 38, the lenslet array separates the transmitted image into an array of beamlets 42, and (in combination with other optical components of the system) images the separated beamlets on the surface of sensor 40. Sensor 40 typically comprises a charged couple device or "CCD," and senses the characteristics of these individual beamlets, which can be used to determine the characteristics of an associated region of optical tissues 34. In particular, where image 44 comprises a point or small spot of light, a location of the transmitted spot as imaged by a beamlet can directly indicate a local gradient of the associated region of optical tissue.

Eye E generally defines an anterior orientation ANT and a posterior orientation POS. Image source 32 generally projects an image in a posterior orientation through optical tissues 34 onto retina R as indicated in FIG. 3. Optical tissues 34 again transmit image 44 from the retina anteriorly toward wavefront sensor 36. Image 44 actually formed on retina R may be distorted by any imperfections in the eye's optical system when the image source is originally transmitted by optical tissues 34. Optionally, image source projection optics 46 may be configured or adapted to decrease any distortion of image 44.

In some embodiments, image source optics 46 may decrease lower order optical errors by compensating for spherical and/or cylindrical errors of optical tissues 34. Higher order optical errors of the optical tissues may also be compensated through the use of an adaptive optic element, such as a deformable mirror (described below). Use of an image source 32 selected to define a point or small spot at image 44 upon retina R may facilitate the analysis of the data provided by wavefront sensor 36. Distortion of image 44 may be limited by transmitting a source image through a central region 48 of optical tissues 34 which is smaller than a pupil 50, as the central portion of the pupil may be less prone to optical errors than the peripheral portion. Regardless of the particular image source structure, it will be generally beneficial to have a well-defined and accurately formed image 44 on retina R.

In one embodiment, the wavefront data may be stored in a computer readable medium 29 or a memory of the wavefront sensor system 30 in two separate arrays containing the x and y wavefront gradient values obtained from image spot analysis of the Hartmann-Shack sensor images, plus the x and y pupil center offsets from the nominal center of the Hartmann-Shack lenslet array, as measured by the pupil camera 51 (FIG. 3) image. Such information contains all the available information on the wavefront error of the eye and is sufficient to reconstruct the wavefront or any portion of it. In such embodiments, there is no need to reprocess the Hartmann-Shack image more than once, and the data space required to store the gradient array is not large. For example, to accommodate an image of a pupil with an 8 mm diameter, an array of a 20×20 size (i.e., 400 elements) is often sufficient. As can be appreciated, in other embodiments, the wavefront data may be stored in a memory of the wavefront sensor system in a single array or multiple arrays.

While the methods of the present invention will generally be described with reference to sensing of an image 44, it should be understood that a series of wavefront sensor data readings may be taken. For example, a time series of wavefront data readings may help to provide a more accurate overall determination of the ocular tissue aberrations. As the ocular tissues can vary in shape over a brief period of time, a plurality of temporally separated wavefront sensor measurements can avoid relying on a single snapshot of the optical characteristics as the basis for a refractive correcting procedure. Still further alternatives are also available, including taking wavefront sensor data of the eye with the eye in differing configurations, positions, and/or orientations. For example, a patient will often help maintain alignment of the eye with wavefront measurement system 30 by focusing on a fixation target, as described in U.S. Pat. No. 6,004,313, the full disclosure of which is incorporated herein by reference. By varying a position of the fixation target as described in that reference, optical characteristics of the eye may be determined while the eye accommodates or adapts to image a field of view at a varying distance and/or angles.

The location of the optical axis of the eye may be verified by reference to the data provided from a pupil camera 52. In the exemplary embodiment, a pupil camera 52 images pupil 50 so as to determine a position of the pupil for registration of the wavefront sensor data relative to the optical tissues.

Figure 3A:
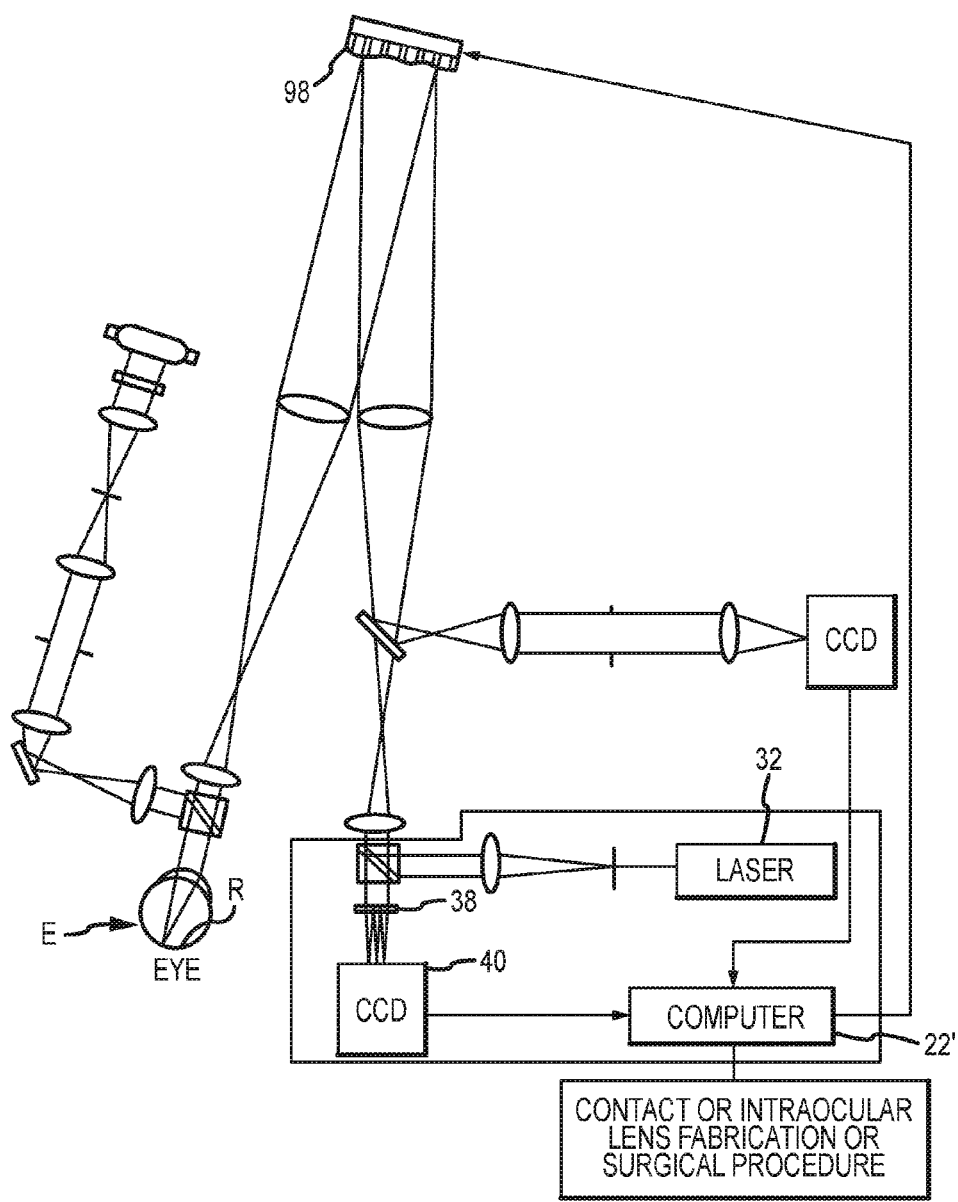
FIG. 3A illustrates another wavefront measurement system according to another embodiment of the present invention.

An alternative embodiment of a wavefront measurement system is illustrated in FIG. 3A. The major components of the system of FIG. 3A are similar to those of FIG. 3. Additionally, FIG. 3A includes an adaptive optical element 53 in the form of a deformable mirror. The source image is reflected from deformable mirror 98 during transmission to retina R, and the deformable mirror is also along the optical path used to form the transmitted image between retina R and imaging sensor 40. Deformable mirror 98 can be controllably deformed by computer system 22 to limit distortion of the image formed on the retina or of subsequent images formed of the images formed on the retina, and may enhance the accuracy of the resultant wavefront data. The structure and use of the system of FIG. 3A are more fully described in U.S. Pat. No. 6,095,651, the full disclosure of which is incorporated herein by reference.

The components of an embodiment of a wavefront measurement system for measuring the eye and ablations may comprise elements of a WaveScan® System. One embodiment includes a WaveScan® System with a deformable mirror as described above. An alternate embodiment of a wavefront measuring system is described in U.S. Pat. No. 6,271,915, the full disclosure of which is incorporated herein by reference. It is appreciated that any wavefront aberrometer could be employed for use with the present invention.

Post-Operative Aberrations

Refractive procedures may, in some cases, induce certain aberrations in an eye of a patient. For example, it is believed that laser-assisted in situ keratomileusis (LASIK) surgeries can induce high order aberrations, and in particular spherical aberration (SA). Spherical aberration is a special type of high order aberration that can affect night vision, and involves off-axis rays entering the eye with different heights of focus at different locations.

Embodiments of the present invention encompass systems and methods for reducing, eliminating, or otherwise compensating for such post-operative inductions. For example, whereas an original target shape applied to the eye may lead to induced aberrations, it is possible to deconvolve the original target shape so as to obtain a modified target shape, such that when the modified target shape is applied to the eye, there are fewer or less pronounced induced aberrations.

Figure 4:
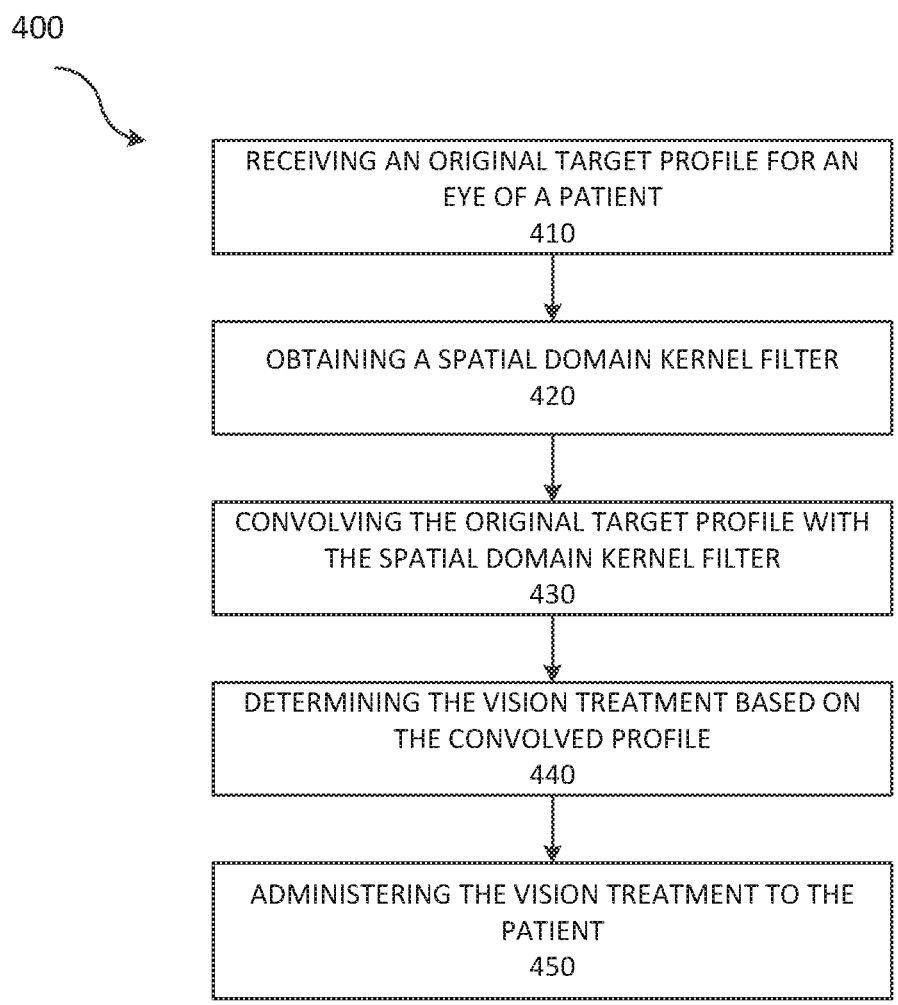
FIG. 4 depicts aspects of a method for determining a vision treatment for an eye, according to embodiments of the present invention.

FIG. 4 depicts aspects of a method 400 for determining a vision treatment for an eye of a patient As shown here, the method includes receiving (e.g. at an input) an original target profile for the eye of the patient as indicated by step 410. Method 400 also includes obtaining a spatial domain kernel filter as indicated by step 420. The spatial domain kernel filter can be based on an inverse Fourier transform of a Fourier domain noise filter. Further, the method may include convolving the original target profile with the spatial domain kernel filter as indicated by step 430. As illustrated here, method 400 also may include determining the vision treatment based on the convolved profile as indicated by step 440. According to some embodiments, methods may include administering the vision treatment to the patient as indicated by step 450.

Figure 5:
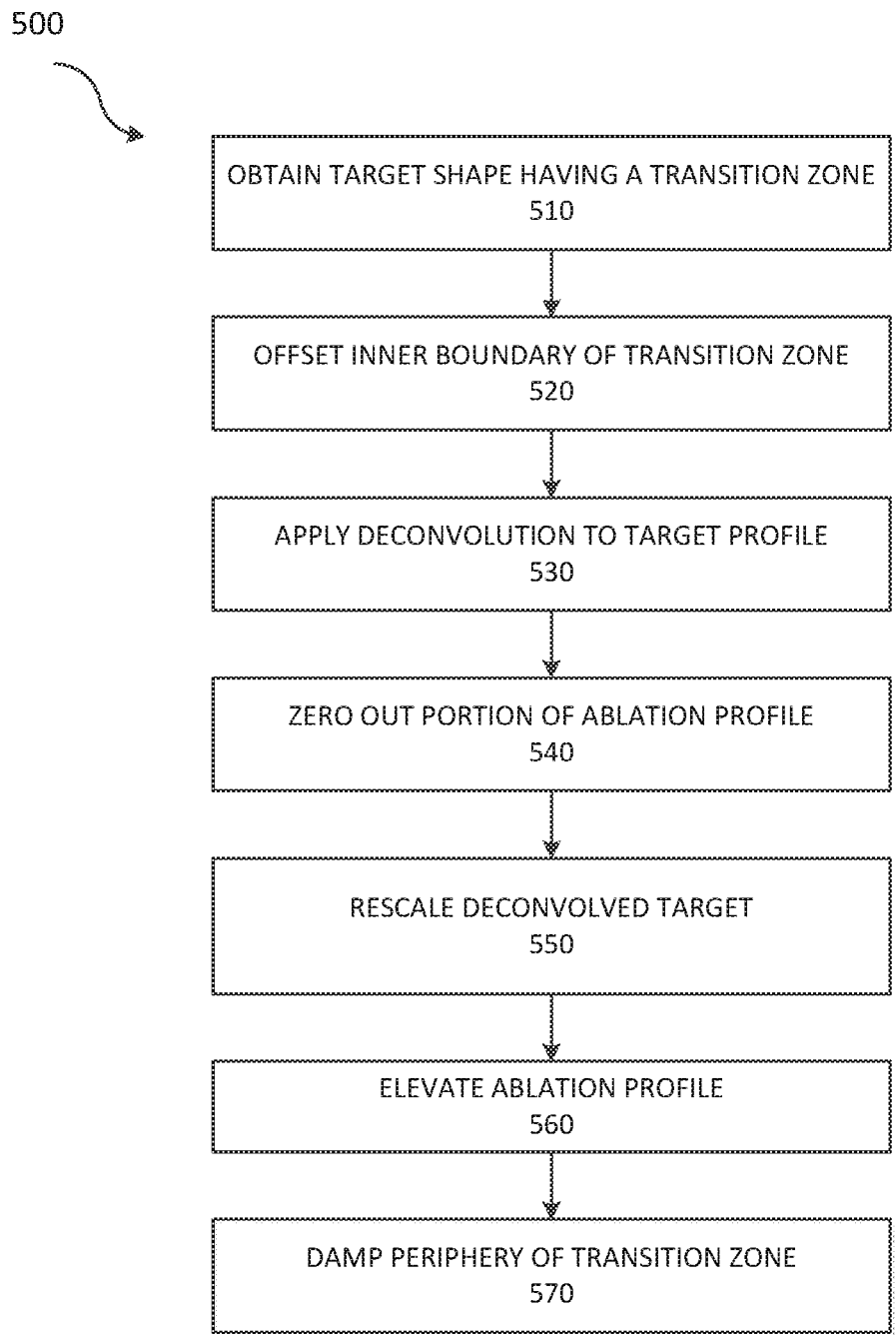
FIG. 5 depicts aspects of a method for modifying a target shape according to embodiments of the present invention.

FIG. 5 depicts aspects of a method for modifying a target shape according to embodiments of the present invention. As shown here, a modification method 500 includes obtaining a target shape as indicated by step 510. Often, the target shape or profile will have an optical zone and a transition zone. In some cases, a target shape may refer to an intended optical surface designed to achieve a given refractive correction. A method 500 for modifying or deconvolving a target shape may also include offsetting an inner boundary of the transition zone (e.g. by about 0.1 mm in diameter), as indicated by step 520. Further, the method may include inputting, receiving, or reading in an inverse smoothing kernel as described elsewhere herein. As illustrated by step 530, methods may include applying a deconvolution to a target profile, for example as a low pass filter multiplied with the target profile as discussed below with reference to Equation 14. Methods may also include zeroing out an ablation profile at distances greater than the transition zone radius, as indicated by step 540. In some cases, methods may include rescaling a deconvolved target, for example as indicated by step 550, so that its Zernike defocus term within the 4 mm diameter is the same as for the original target. In some instances, the rescaling factor can be 1.0. Optionally, methods may include elevating the entire ablation profile, as depicted by step 560, so that the lowest point on the ablation profile is zero. This elevation technique can help to ensure that the ablation profile does not have negative heights. In some instances, methods may include applying a damping multiplier (e.g. Equation 17) to the periphery of the transition zone, as indicated by step 570. Optionally, a modification or deconvolution method can be implemented before application of a cosine compensation step.

Post-Operative Epithelial Smoothing and Spherical Aberration

As noted above, cornea remodeling following treatment with a refractive target shape can induce SA, for example due to smoothing of epithelium at the anterior surface of the eye. To develop techniques that compensate for such remodeling, it is helpful to simulate the post-operative epithelium smoothing process with a model. An exemplary model may define the shape of the post-operative cornea surface as a convolution of an ablation target profile with a low-pass filter (LPF), as follows:

$$h_{post-op} = h_{pre-op} - K \otimes T \qquad \text{Equation 1}$$

where T is the ablation target profile. K=K(x,y) is the LPF kernel, which has the following Fourier transform:

$$K(k_x, k_y) = \frac{1}{1 + \sigma^2(k_x^2 + k_y^2)} \qquad \text{Equation 2}$$

K(x,y), the LPF kernel, can be considered as a spatial domain representation. The Fourier transform of K(x,y) (i.e. $K(k_x, k_y)$ or F[K]), can be considered as a frequency or Fourier domain representation.

According to some embodiments, the Fourier transform F[K], or $K(k_x, k_y)$, may be a squared Butterworth low-pass filter of the first order, which can be applied to the treatment target T in order to obtain the wavefront change due to corneal smoothing. In some instances, the Fourier transform of the LPF kernel can be defined by or based on a single diffusion coefficient σ, which has a unit of length.

In some embodiments, the post-operative induced spherical aberration can be computed with a Zernike decomposition of the simulated post-operative cornea surface after the smoothing, as follows:

$$SA_{post-op} = SA_{pre-op} - SA(K \otimes T) \qquad \text{Equation 3}$$

The spherical aberration computed by Zernike decomposition of a given target can be represented by the function SA(T), where SA(T) refers to SA from the target T.

According to an exemplary experimental embodiment, a target for each eye in a US IDE clinical study was computed as follows:

$$T = \text{scale} \cdot T_{controller} \qquad \text{Equation 4}$$

According to some embodiments, $T_{controller}$ may refer to a target created by production code. Such a target can be created according to various options. For example, the target shape can be generated based on input such as measured pre-operative Zernike coefficients with added flap-induced spherical aberration (e.g. flapSA). The target shape can also be generated with or without applying a cosine correction (e.g. warping adjustment). In some cases, the target can be generated based on scaling and/or physician adjustments. Target shapes may also be generated based on keratometry parameters. For example, if available, keratometry parameters k1, k2, k2a may be used. Optionally, for example if keratometry parameters are not available, default values of k1=43.5, k2=43.5, k2a=0 may be used.

Figure 7:
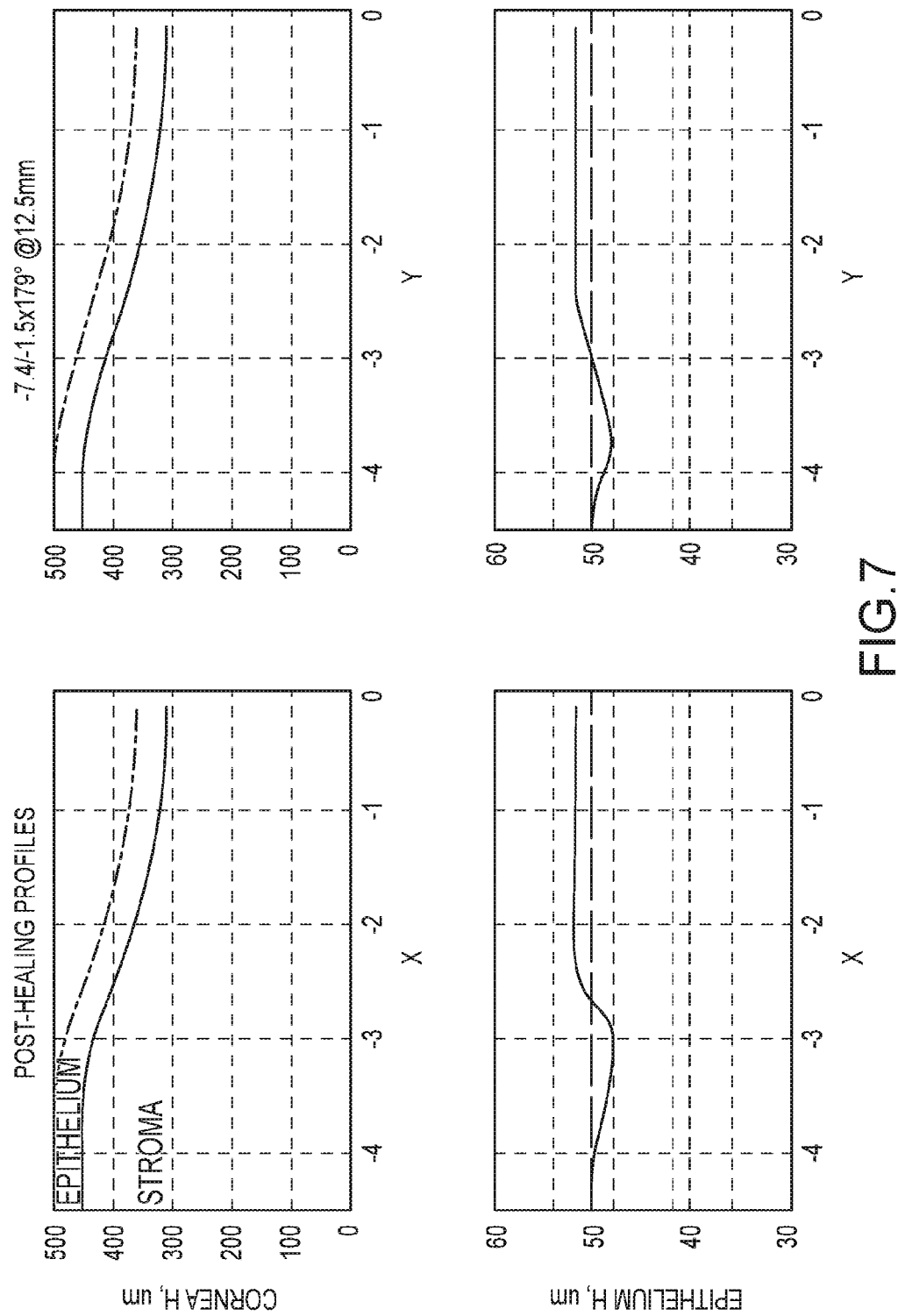
FIG. 7 shows aspects of simulated epithelium thickness profiles according to embodiments of the present invention.

It is possible to simulate the cornea thickness after smoothing using an LPF model. For example, FIG. 7 shows simulated epithelium thickness profiles after smoothing (High Myopia study, case ID=21011 OD, −7.4 D/−1.5 D×179). For this illustration, pre-operative epithelium was assumed uniform and 50 um thick. Corneal smoothing after a myopic ablation may lead to epithelium diffusion, from high curvature areas on the peripheral transition zone, toward the center where the curvature is smaller. As a result, the epithelium may become thicker in the center and thinner on the periphery of the ablation target. This effect may help explain partial regression after myopia refractive surgery.

Using available clinical data, a smoothed target was compared with the observed 6M corneal change within 6 mm and 5.5 mm diameter optical zone. A diffusion coefficient σ was estimated based on the comparison. In some cases, the comparison can be performed with a linear least-square fit of the model to the observed SA change, as described elsewhere herein. According to some embodiments, the fitting procedure yielded an estimation of σ and its confidence interval for each value of flapSA.

Figure 8A:
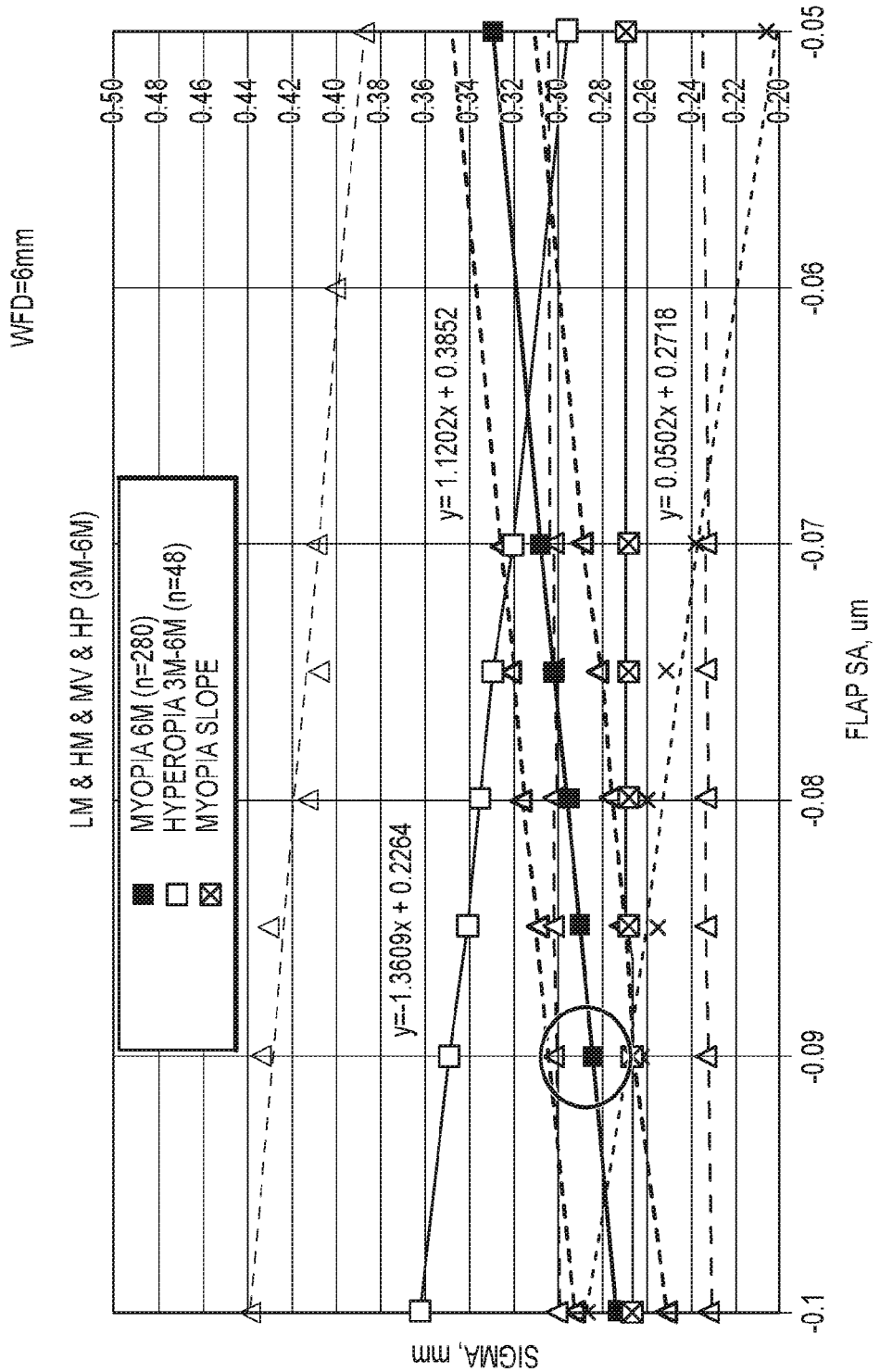
FIGS. 8A and 8B show aspects of flap SA and sigma relationships according to embodiments of the present invention.
Figure 8B:
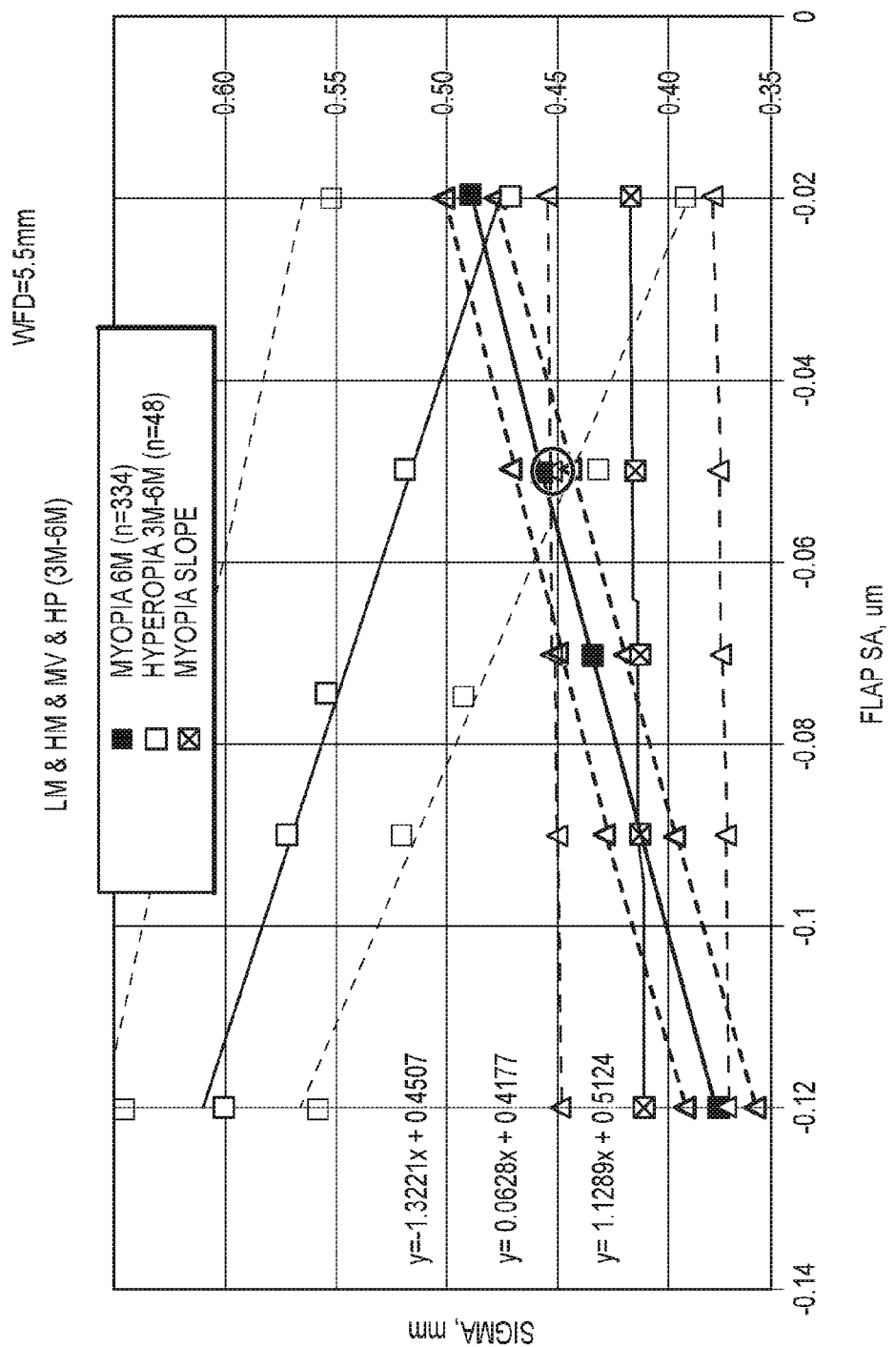

Various independent estimations of σ were used, including (a) RMS match for low and high Myopia (6M), (b) and Hyperopia (6M-9M), and (c) slope-based estimation for low Myopia (6M). For example, FIGS. 8A and 8B depict optimized sigma vs. flap induced SA (simulations for clinical studies) for WFD=6 mm and WFD=5.5 mm, respectively. The dashed lines represent confidence intervals. WFD refers to a wavefront diameter.

As flap-induced aberrations typically do not depend on the type of the subsequent treatment, it is possible to assume that the optimal values for flapSA and σ can be chosen within the crossing of confidence intervals for these three estimates (e.g. circled data points in FIGS. 8A and 8B). These points can define optimal values approximately σ=0.3 mm, flapSA=0.09 um for 6 mm wavefront and σ=0.45 mm, flapSA=0.05 um for 5.5 mm wavefront. Some clinical observations for a flap incision without a subsequent ablation show close values for the flap induced SA (e.g. flapSA≅=0.07 um).

Figure 9A:
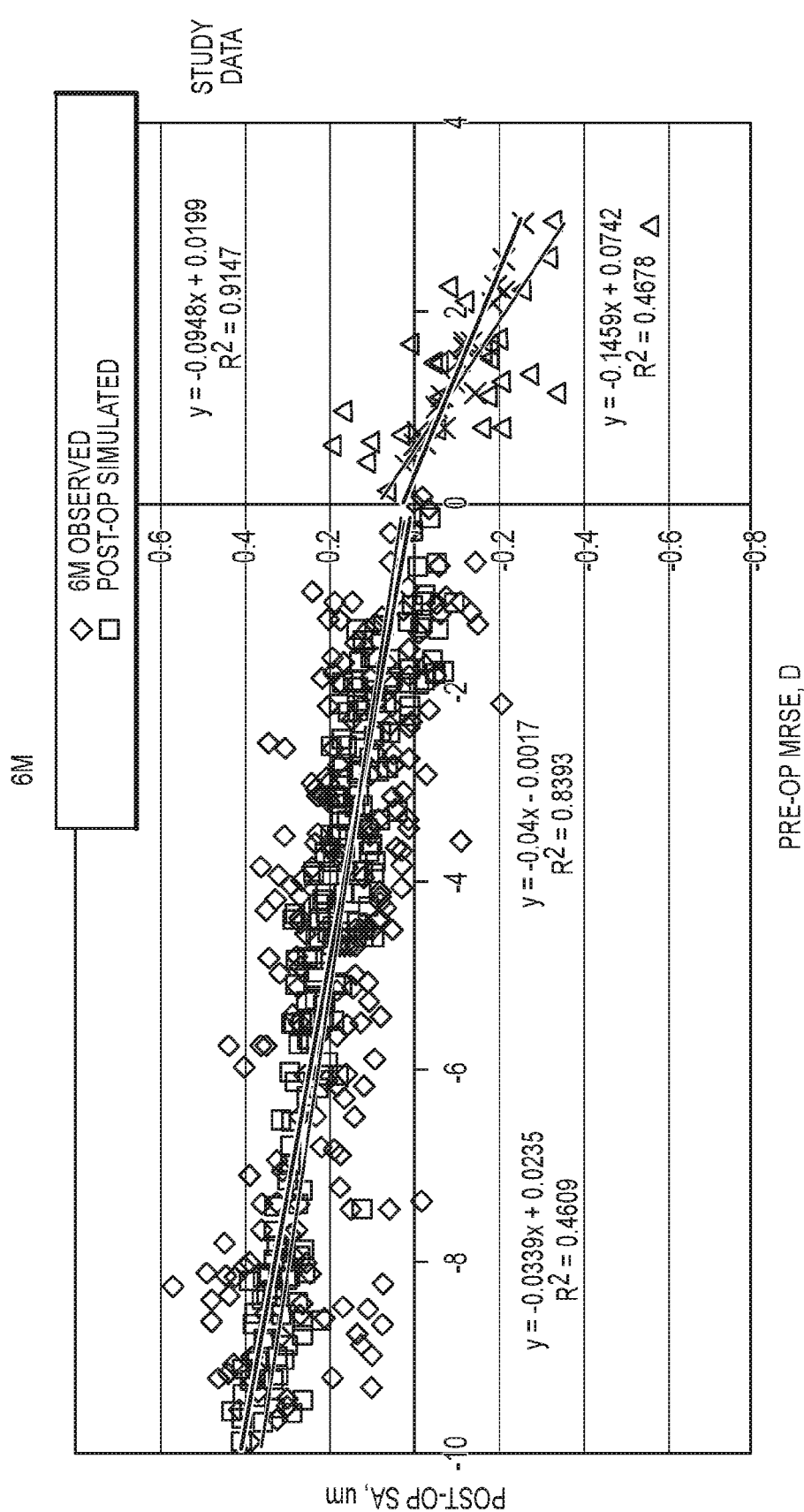
FIGS. 9A to 9C depict aspects of post-operative SA and pre-operative MRSE or SE relationships according to embodiments of the present invention.
Figure 9B:
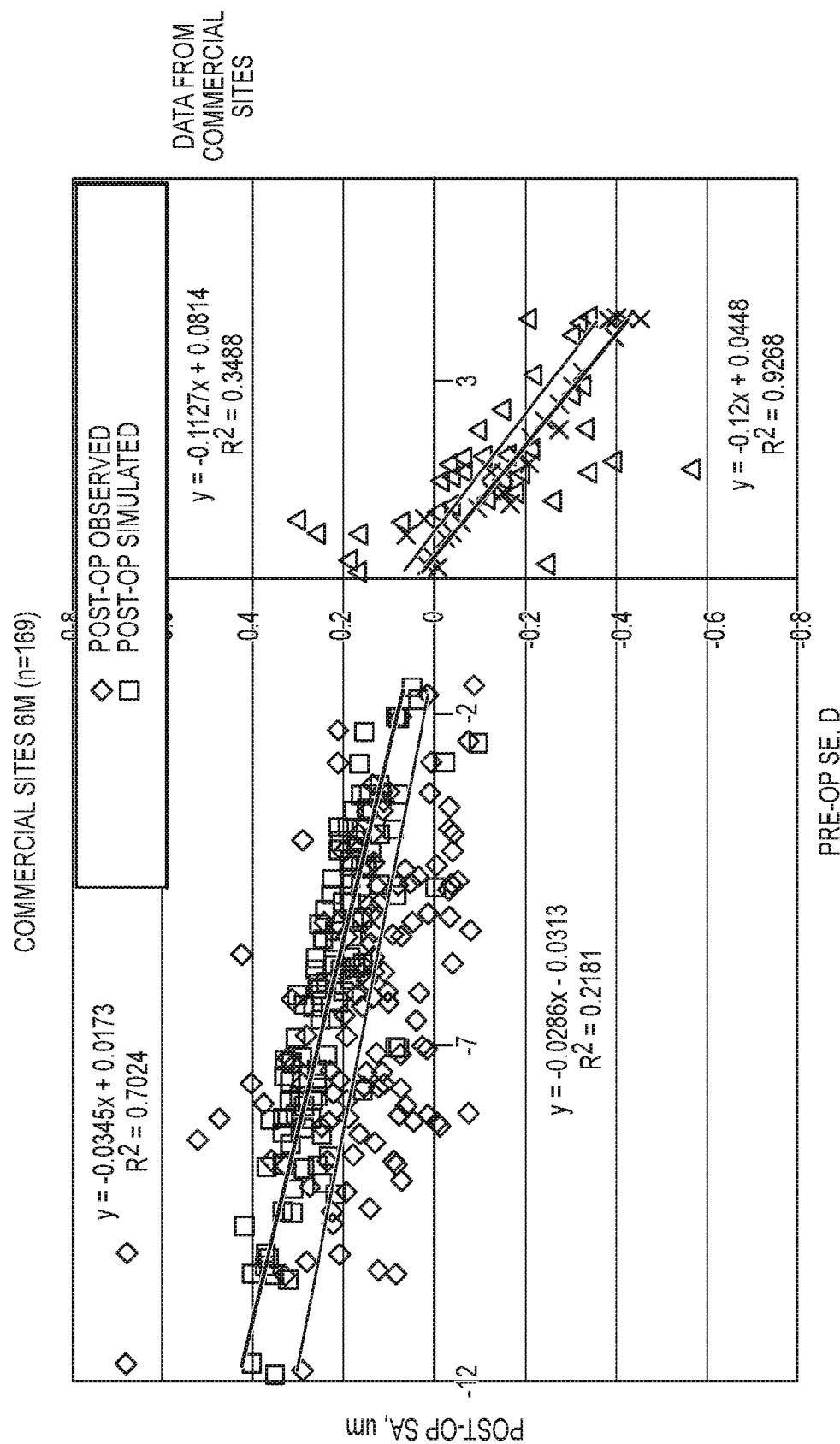
Figure 9C:
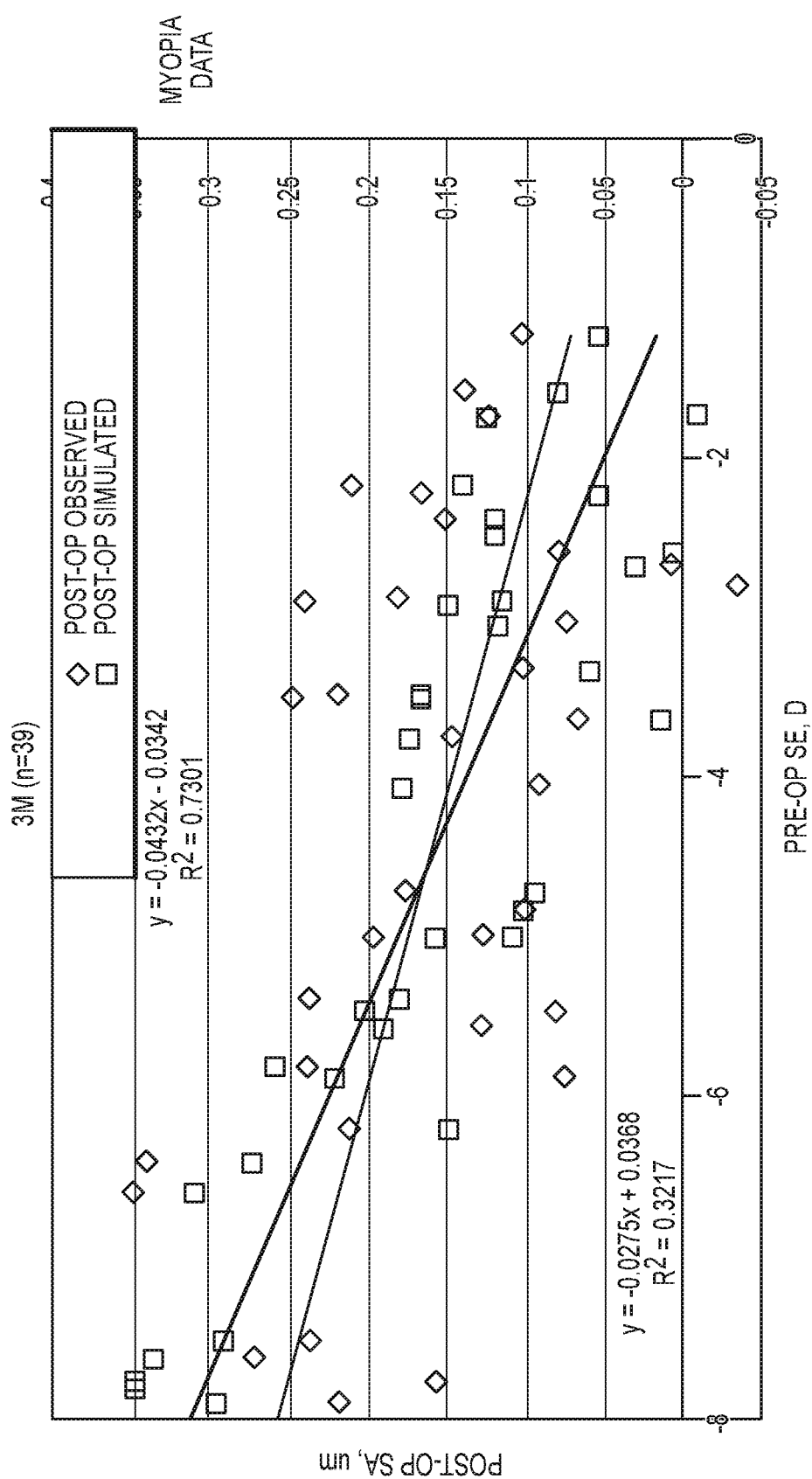

It is possible to compare simulated and observed post-operative SA (e.g. with WFD=6 mm). For example, as depicted in FIGS. 9A, B, and C, an estimated diffusion coefficient σ=0.3 mm for 6 mm wavefront diameter may be validated by comparison of simulated post-operative SA with the actual observed values. A flapSA=0.09 um was assumed for all data sets. In some embodiments, this value might be different for mechanical microkeratome and IntraLase® femtosecond laser treatments. As illustrated here, trend lines for simulated and observed data can be almost identical for myopia and high myopia data and rather close for other data sets.

Hence, it is understood that epithelial smoothing subsequent to refractive surgery can induce SA, and that simulation of smoothing can be helpful in developing approaches that compensate for the smoothing. In some cases, it is possible to define the shape of the post-operative cornea surface as a convolution of an ablation target profile with a low-pass filter (LPF).

In some cases, the post-operative epithelium smoothing process can be simulated by defining the shape of the post-operative cornea surface as a convolution of the ablation target profile with a low-pass filter (LPF) as follows (spatial domain):

$$h_{post-op} = h_{pre-op} - K(x,y) \otimes T(x,y) \qquad \text{Equation 5}$$

where h stands for the elevation maps, ⊗ denotes a convolution, T(x, y) is the ablation target profile and K(x, y) is a low pass filter (LPF) kernel, which has the following Fourier transform:

$$K(k_x, k_y) = \frac{1}{1 + \frac{\sigma^2(k_x^2 + k_y^2)}{(0.5\ dL)^2}} \qquad \text{Equation 6}$$

Equation 6, which is in the Fourier domain, represents a squared Butterworth low-pass filter of the first order, which can be applied to the treatment target in order to obtain the wavefront change due to the corneal smoothing. It can be defined by a single diffusion coefficient σ, which has a unit of length. For some discrete case embodiments, the 101×101 mesh size can be dL=0.1 mm. Based on optimizations using data from certain clinical trials, a sigma of 0.35 mm was determined to best explain that observed data.

According to some embodiments, K(x, y) is in the spatial domain, and is a Fourier transform of K($k_x$, $k_y$). Here, $k_x$ and $k_y$ are Fourier domain or frequency domain variables. According to some embodiments, K(x, y) is an LPF kernel that can be exemplified by a 101×101 matrix or by a 3-D surface expressed in matrix form where x and y are spatial domain variables.

Matching Simulation Results Vs. Observed Data

According to some embodiments, it is possible to match or compare simulated post-operative SA with observed 6M post-operative SA using linear least-square fit of the model to the observed SA change by minimizing the following function:

$$F = \sum_{all\_eyes} \frac{[flapSA + SA(K \otimes T) - (SA_{post-op} - SA_{pre-op})]^2}{N} \qquad \text{Equation 7}$$

Here $SA_{pre-op}$ and $SA_{post-op}$ are spherical aberration values for pre-operational and 6M post-operative wavefront measurements, flapSA is the immediate flap-induced SA value before the smoothing, and N is the number of eyes. It is possible to compute this function (F) for different flapSA and diffusion coefficients, σ, and for each flapSA to find the value σ min where fitting residual is minimal. SA (K⊗T) refers to the SA of the target T after LPF.

The confidence interval for the optimized σ can be roughly estimated as:

$$\Delta\sigma = \frac{std([SA(K \otimes T) - (SA_{post-op} - SA_{pre-op})]^2)}{\sqrt{N}} \cdot \frac{d\sigma}{dSA} \qquad \text{Equation 8}$$

Here std is a standard deviation, computed for the ensemble of eyes with the optimized value σ=$σ_{min}$.

Both optimized σ and its confidence interval can depend on the value of flapSA. This dependence can be computed separately for myopic (6M) and hyperopic (6M-9M) eyes, for example as depicted in FIGS. 8A and 8B. Hence, it is possible to have two independent estimations for optimized flapSA and σ.

An alternative estimation of these values can be obtained from matching the simulated vs. observed trend slopes, as follows:

$$\left(\frac{d\Delta SA^{(sim)}}{dSE_{pre-op}}\right)_{all\_eyes} = \left(\frac{\Delta SA^{(exp)}}{dSE_{pre-op}}\right)_{all\_eyes} \qquad \text{Equation 9}$$

Here $\Delta SA = SA(K \otimes T) - (SA_{post-op} - SA_{pre-op})$. The optimized σ can provide a simulated slope that is the same as the observed slope. A confidence interval for this estimate can be defined as 95% confidence interval for the slope of linear regression, as follows:

$$\Delta\sigma = \frac{d\sigma}{dSA} \cdot \frac{t_{0.025} \cdot s}{s_x \sqrt{N-1}} \qquad \text{Equation 10}$$

Here $$t_{0.025} = 1.96,\ s^2 = \frac{N-1}{N-2} \cdot \left(s_y^2 - s_x^2 \frac{dSA_{post-op}}{dSE_{pre-op}}\right),$$

$$s_x = stdev(SE_{pre-op}),\ s_y = stdev(SA_{post-op}).$$

The slope-based estimation was calculated for a Myopia study.

Offset Transition Zone

In some instances, a target shape or ablation target profile will include an optical zone and a transition zone. The aggregate of the optical zone and transition zone may be referred to as an ablation zone, corresponding to the entire corneal region covered by a laser ablation. The optical zone may refer to a corneal region which received a full intended refractive treatment. A transition zone may refer to a corneal region outside of the optical zone but inside of the ablation zone. Often, a transition zone receives a treatment that is not strictly optically correct. With returning reference to FIG. 5, exemplary methods may also include offsetting an inner boundary of the transition zone, as indicated by step 520.

According to some embodiments, an original target shape may include a transition zone starting at about 0.25 mm inside the boundary of the optical zone. It is possible that such a target may induce some post-operative SA, independent of any effect cornea smoothing may have on post-operative SA. Hence, a total induced SA may include a target-induced SA combined with a subsequent smoothing-induced SA.

Figure 6A:
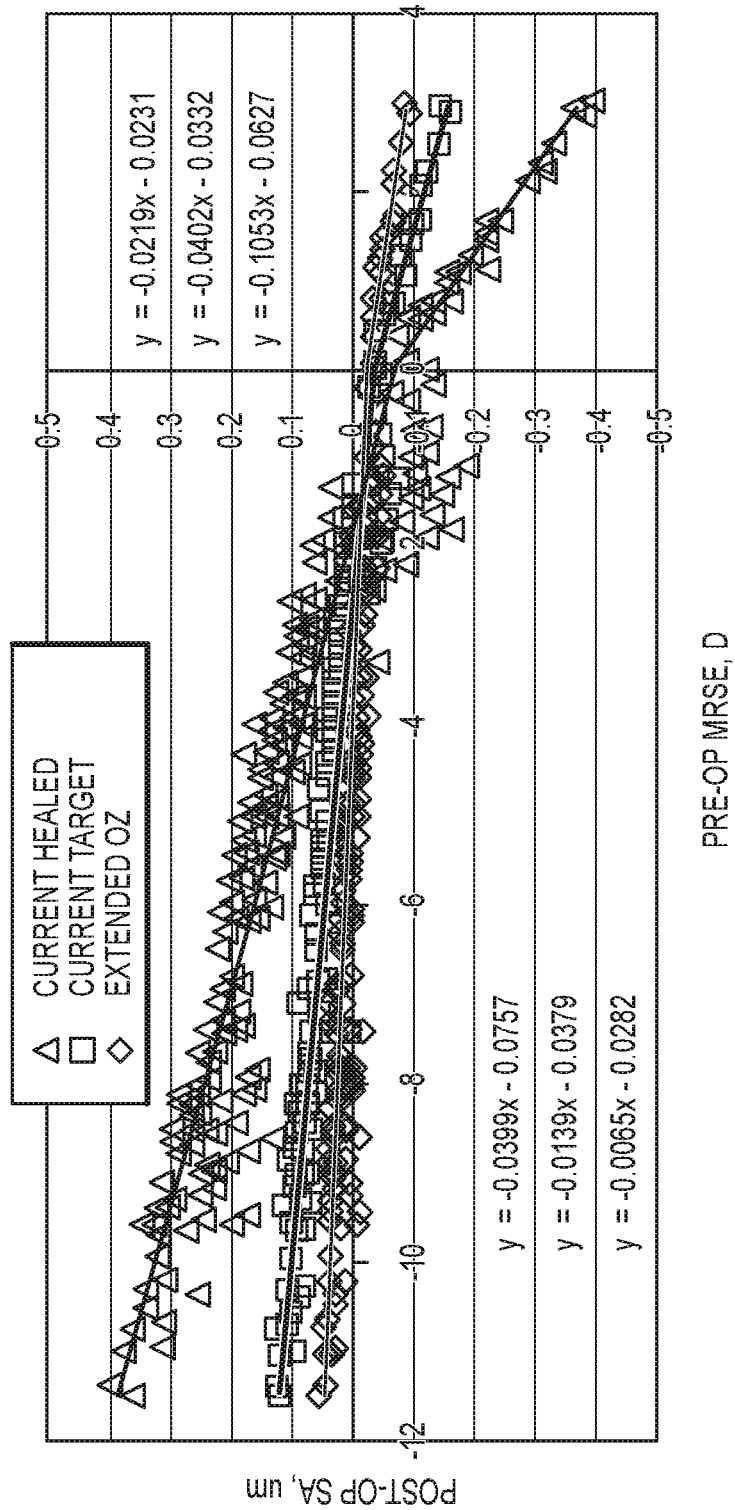

For example, FIG. 6A depicts post-operative values, in microns, simulated with σ=0.3 mm for study data (n=340), for SA as indicated in Table 1.

TABLE 1

| Symbol | Source of induced SA |
|---|---|
| □ | Original target shape, no corneal smoothing (i.e. immediately after ablation) |
| Δ | Original target shape, and corneal smoothing |
| ◊ | Modified target shape (transition zone extended by 0.1 mm), no corneal smoothing |

As shown here, a target-induced SA (□) may be reduced or even completely eliminated with a small offset of the transition zone (◊). In some cases, the offset of the transition zone may cause sharper gradients in the peripheral target. A 0.05 mm radial shift of the inner boundary of the transition zone away from the center of the optical zone, for example as shown in FIG. 6B, (corresponding to a diameter change of 0.1 mm), can make the trend slope for target-induced SA vs. pre-operative SE about twice as small and bring the magnitude of target-induced SA (◊) below 0.1 um level, which may be considered negligible. In some instances, by offsetting the inner boundary of the transition zone (e.g. by about 0.1 mm in diameter), the target induced SA can be reduced by about 50% (e.g. 0.1 mm change in diameter). As depicted here, correcting the target induced SA can be effective to remove post-operative SA.

Deconvolution

With returning reference to FIG. 5, a method of modifying a target shape can also include applying a deconvolution to the target profile or shape, as indicated by step 530. For example, methods may include applying a low pass filter (LPF) deconvolution (e.g. with σ=0.35 mm) to the target profile. Sigma (σ) can refer to a diffusion coefficient related to the strength of an LPF process.

According to some embodiments, the application of a deconvolution transformation to an original target can operate to compensate for the area of high curvature, which can be a significant cause of post-operatively induced SA.

In some instances, an LPF kernel for a deconvolution may be the same as the one optimized to fit an observed induced post-operative SA, for example such as those described above in connection with the post-operative epithelial smoothing and spherical aberration. Corneal smoothing, simulated as convolution with an identical or similar LPF kernel, can bring the cornea back to the desired shape.

In some instances, high-frequency variations may be suppressed by diffusion or LPF convolution. Restoration of such suppressed variations by deconvolution may introduce inaccuracies, which may also be influenced by a signal-to-noise level.

Embodiments of the present invention encompass the use of deconvolution techniques which can reduce the degree to which suppressed variations may introduce such inaccuracies. For example, deconvolution techniques may involve the use of a deconvolution filter, combining an LPF kernel, K, and a signal-to-noise ratio, SNR. The Fourier transform of such a filter can be expressed as follows:

$$DK(\vec{k}) = \frac{K^*(\vec{k})}{|K(\vec{k})|^2 + SNR^2}$$ Equation 11

Here K(k) represents a Fourier transform of a LPF kernel, the asterisks refers to a complex conjugate, and SNR is the signal-to-noise ratio. According to some embodiments, the SNR is assumed to be constant. The value of SNR can define which scales will be restored by the deconvolution, reversing diffusion effect on them. In some instances, SNR can be 0.1. If the SNR is excessively small, many small features may be amplified. If the SNR is excessively large, only relatively large features will be amplified. In exemplary embodiments of the present invention, SNR has a value within a range from 0 to 0.1.

If there are no noises and SNR=0, deconvolution should bring back exactly the original target, which existed before the LPF was applied. Where finite noises are present, small features may be irreversibly lost after low-pass filtering and, therefore, deconvolution may restore the original target only with a finite accuracy. The error of restoration can be estimated with applying a LPF to a target and then using deconvolution to restore it and compare it with the original target.

Figure 10A:
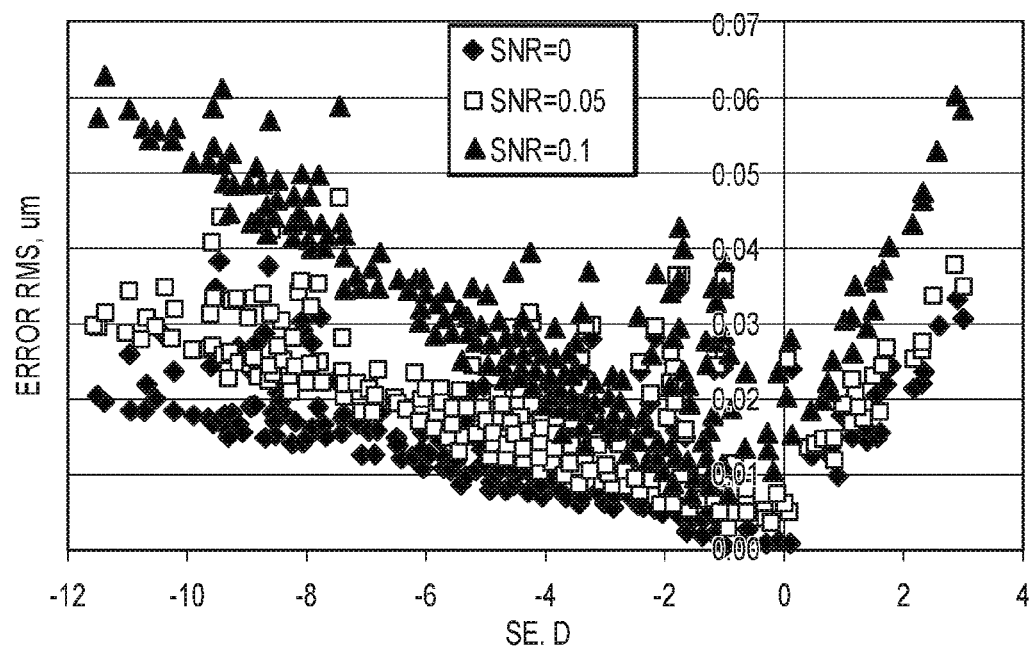
FIGS. 10A and 10B illustrate aspects of spherical aberration errors for deconvolution according to embodiments of the present invention.
Figure 10B:
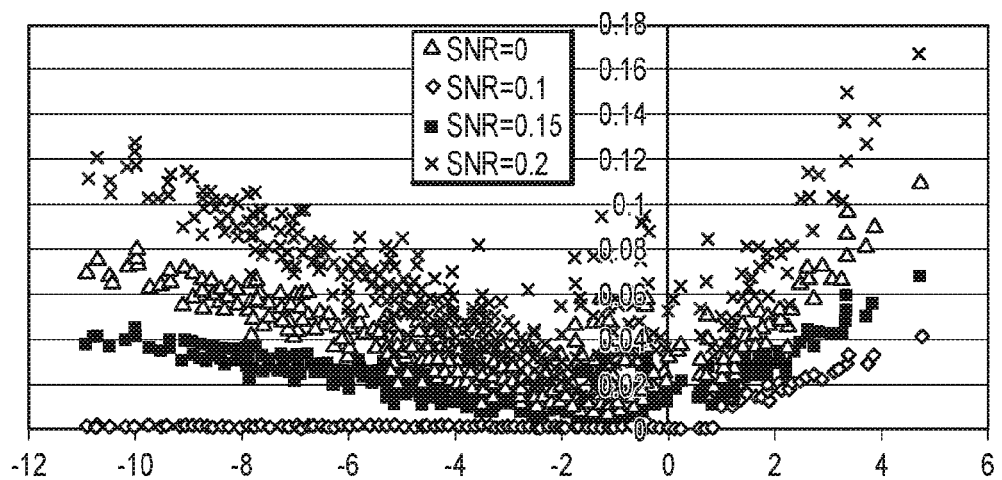

FIG. 10A shows spherical aberration RMS errors for deconvolution for different SNR values, estimated for study targets (n=340) with σ=0.3 mm, where WFD=6 mm. As depicted here, with SNR=0.1, all SA RMS errors are below 0.07 um level. FIG. 10B shows SA errors for a similar deconvolution, estimated for study targets (n=515) with σ=0.28 mm.

Any small and narrow dips in the measured pre-operative wavefront may be amplified by the deconvolution. This may result in small-size features that are too narrow to resolve with laser pulses, which are often restricted to a width of about 1 mm.

In some cases, it is not necessary or desirable to ablate these very narrow features, as they may be flattened by the smoothing process. What is more, these features may also have little influence on the vision quality. In some cases, it is possible to effect the deconvolution so as to neglect or minimize these features and amplify only relatively large-scale features of the ablation target. For example, this can be done by optimizing the SNR value in a deconvolution process. It has been found that by using SNR≥0.1, for example, any features smaller than 0.5 mm are not amplified by deconvolution. Hence, SNR=0.1 may be used a default parameter.

A deconvolved target typically has an oscillating profile at the periphery. These oscillations may be mainly caused by boundaries between the optical zone, transition zone, and an edge of the finite-size target, where either the target profile or its derivatives have sharp changes.

Embodiments of the present invention encompass the use of deconvolution and related techniques to compensate for the post-operative induction of high order aberrations (HOAs), and in particular spherical aberration (SA). Accordingly, the visual quality of patients receiving treatments according to these techniques provides desirable results, particularly in the management of night vision symptoms. Often, deconvolution procedures will result in treatment target shape changes near the periphery of the optical zone.

For example, within a central 4 mm area, the refraction of a modified target shape may be similar or identical to that of an original target shape.

According to some embodiments, to obtain a new or modified target shape, a deconvolution process can be employed as follows:

$$T_{new} = K_{INV} \otimes T_{current} = F\left[\frac{K*(k_x, k_y)}{|K(k_x, k_y)|^2 + SNR^2}\right] \otimes T_{current} \quad \text{Equation 12}$$

where F(•) stands for a Fourier transform, * denotes a complex conjugate, $T_{current}$ is an original treatment target, $T_{new}$ is the new target that is intended to remove the post-operative SA, and $K_{INV}$ is the inverse kernel of K. The SNR can be used to prevent or inhibit noise amplification and oscillation at the edge. In some instances, a SNR value of 0.1 may be suitable for practical purposes. To prevent or as a substitute for real-time calculation of the Fourier transforms, the inverse kernel $K_{INV}$ can be pre-calculated and applied in real-time as a look-up table or a resource file. A suitable SNR value can prevent the denominator from being zero or excessively small, which may otherwise results in the matrix quotient being unreasonably large.

According to some embodiments, an inverse kernel can be exemplified as a convolution kernel that operates like a deconvolution procedure. In this sense, a deconvolution operation may be considered to be an inverse procedure of a convolution operation.

Embodiments of the present invention encompass techniques for calculating an inverse smoothing kernel $K_{INV}$. Whereas a low pass filter (e.g. Butterworth kernel) such as K(x, y) is in the Fourier domain, the inverse kernel is in the spatial domain. Instead of implementing a Fourier transform, it is possible to perform a spatial convolution implemented as multiplication.

Figure 19:
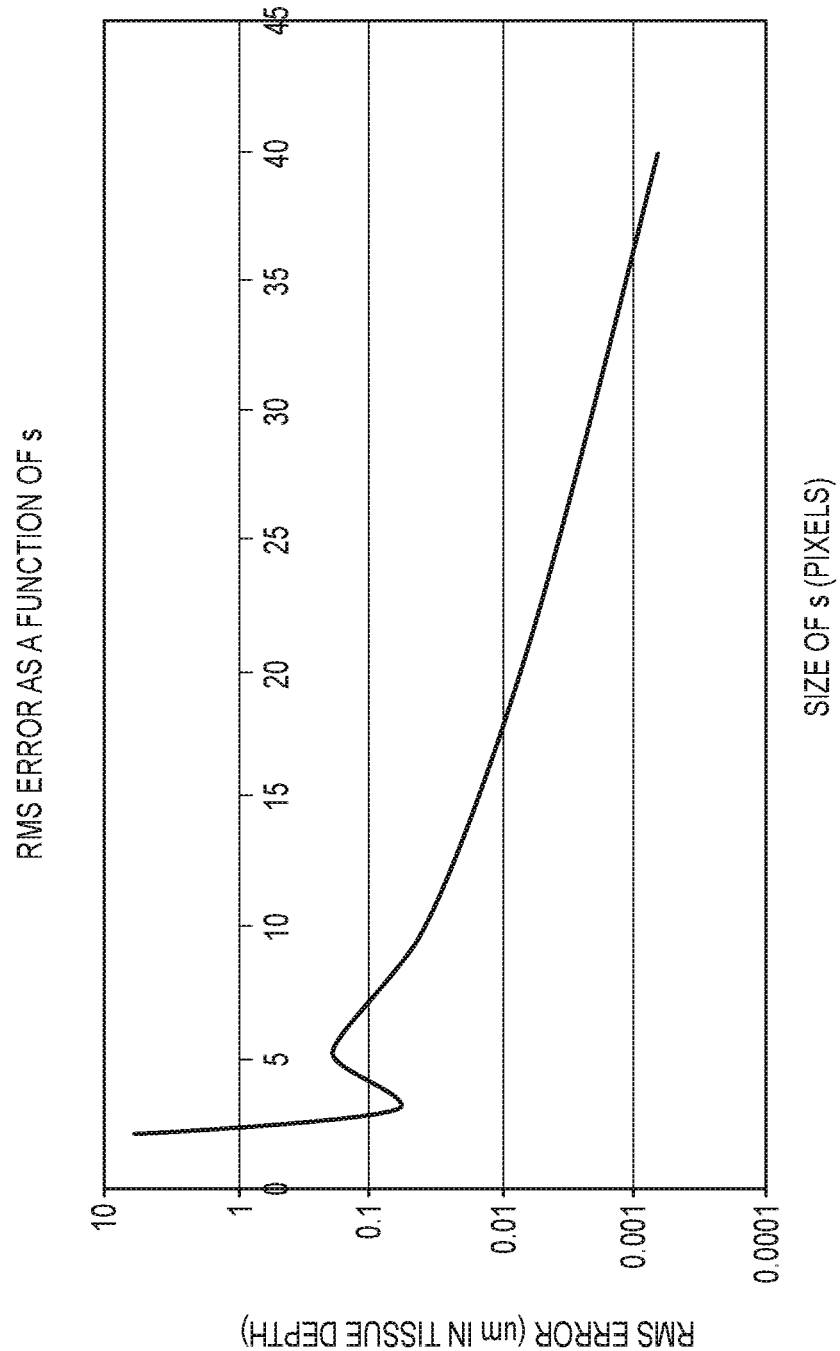
FIG. 19 depicts aspects of relationships between RMS error and size of s (pixels), according to embodiments of the present invention.

In some cases, embodiments encompass rapid convolution calculations (e.g. in the order of several milliseconds) for UI (user interface) manipulation, in a practical implementation. A normal implementation for a spatial 2-D convolution may involve four netted loops each with 101 elements. Such embodiments may be related to the 101×101 mesh size cases discussed above in the paragraph following Equation 6. A 2-D spatial convolution can be written as follows:

$$T_{new}(i, j) = \quad \text{Equation 13}$$

$$T_{current} \otimes K_{INV} = \sum_{k=-\infty}^{\infty} \sum_{l=-\infty}^{\infty} T_{current}(i-k, j-l) K_{INV}(k, l)$$

where $K_{INV}$ is the 2-D inverse smoothing kernel. In some cases, $K(k_x, k_y)$ may be a Butterworth of the first kind, and its inverse may have an actual size that is only a few pixels wide. Therefore, Equation 13 may be rewritten as follows:

$$T_{new}(i, j) = T_{current} \otimes K_{INV} = \quad \text{Equation 14}$$

$$\sum_{k=-s}^{s} \sum_{l=-s}^{s} T_{current}(i-k, j-l) K_{INV}(51+k, 51+l)$$

where the inverse kernel size is treated as (2s+1)×(2s+1) in size. When s=17, or the inverse kernel frame size of 35×35, RMS error using Equation B is about 0.01 microns. With s=37, use of Equation 14 may be about 7 times faster than Equation 13, but the error is within 0.001 microns. FIG. 19 shows the relationship between the RMS error and the size of s (pixels), with a simulation of 515 eyes. This figure depicts the RMS error as a function of s when Equation 14 is used (e.g. in contrast to Equation 17 as discussed below).

Zero Out

With returning reference to FIG. 5, a method of modifying a target shape can also include zeroing out an ablation profile at distances greater than the transition zone radius, as indicated by step 540.

Typically, no ablation is performed beyond the end of transition zone. Hence, it is possible to zero-out the ablation profile at distances greater than the transition zone outer radius, $R_{TZ}$, as discussed elsewhere herein, for example with regard to FIGS. 12C and 12D.

A zeroing-out procedure can be included, so as to prevent artifacts and the like that might occur as a result of performing convolution or deconvolution. For example convolution or deconvolution may inadvertently or unintentionally introduce nonzero or negative values at positions outside of the transition zone. A zeroing-out operation can be instituted as a safeguard, so as to ensure that such non-zero or negative values are removed, which could otherwise cause complications for a tissue ablation protocol.

Rescaling Deconvolved Target

As shown in FIG. 5, a method of modifying a target shape can also include rescaling a deconvolved target, as indicated by step 550. For example, a deconvolved target can be rescaled so that its Zernike defocus term within a 4 mm diameter is the same as that for an original target. In this way, the spherical equivalent refraction of a modified or deconvolved target can be the same as that for an original target. In some instances, a rescaling procedure can be performed to ensure that the refractive power for a deconvolved target is the same as that for an original target. In some cases, the refractive power for a deconvolved target is the same as that for an original target and no rescaling step is performed.

According to some embodiments, an original target shape may perform adequately for correcting or treating refraction errors, and hence a modified target shape based on the original target shape may be generated so that the refraction of the modified target is the same as for the original target. This can be achieved, for example, by rescaling of the deconvolved target so that its defocus Zernike term within the 4 mm area (which defines wavefront-based SE) is the same as for the current target. A rescaling coefficient, which is the ratio of the defocus terms for the current and deconvolved targets, may be expressed as follows:

$$\text{rescale} = \frac{SE_{current}}{SE_{de-conv}} \quad \text{Equation 15}$$

Figure 11A:
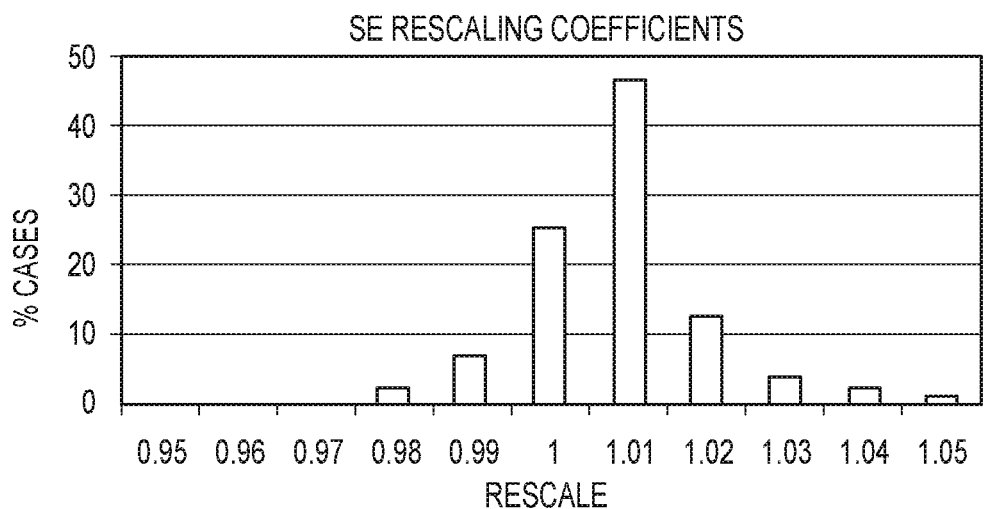
FIGS. 11A and 11B show aspects of rescaling coefficients and refraction errors, respectively, according to embodiments of the present invention.
Figure 11B:
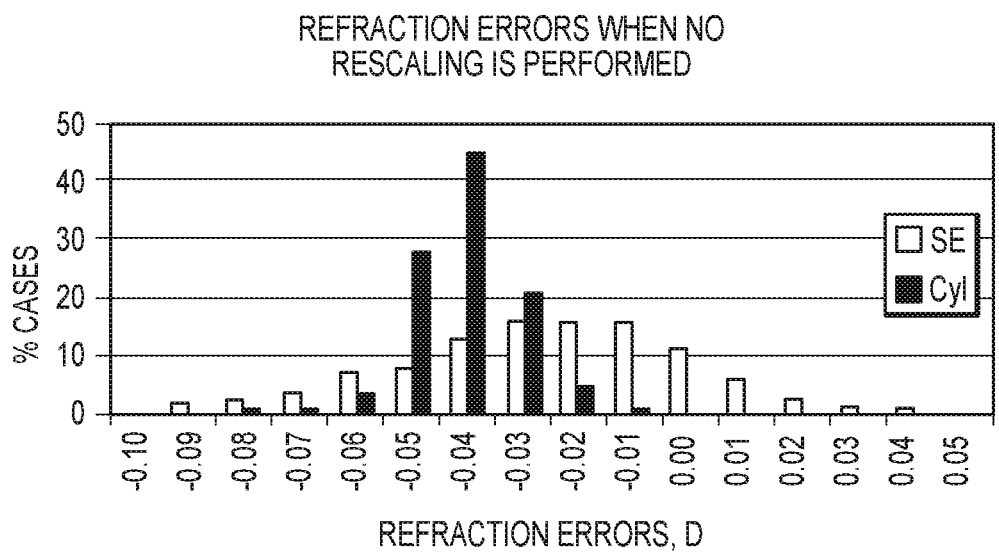

The rescaling coefficient may be close to 1, and distributed as shown in FIGS. 11A and 11B. For example, a rescaling coefficient may have a mean value of 1.003, such as that which was found for US IDE studies. In such instances, rescaling may not be needed, in practical terms. In no rescaling is performed, then resulting refraction errors may be below 0.1 D, for example as shown in FIG. 11A. Hence, it may be possible to neglect or ignore such small values. FIG. 11B shows a distribution of SE re-scaling coefficients and refraction errors without rescaling for the studies (n=340).

Figure 12B:
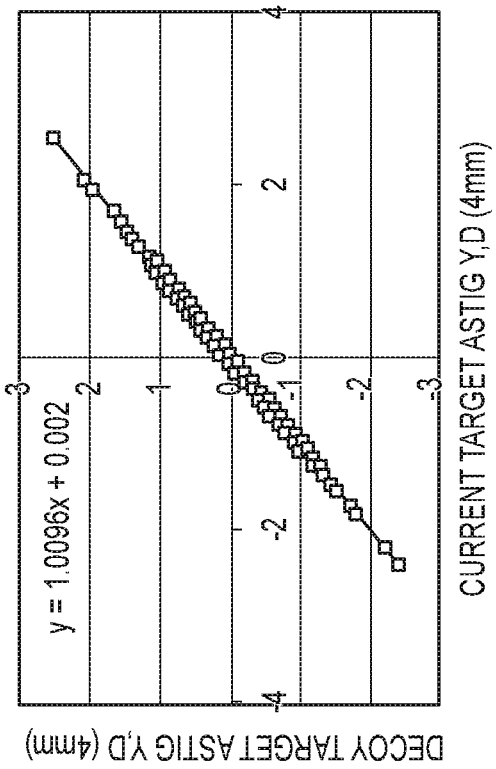
FIGS. 12A and 12B depict aspects of effects of deconvolution on cylinder refraction according to embodiments of the present invention.
Figure 12A:
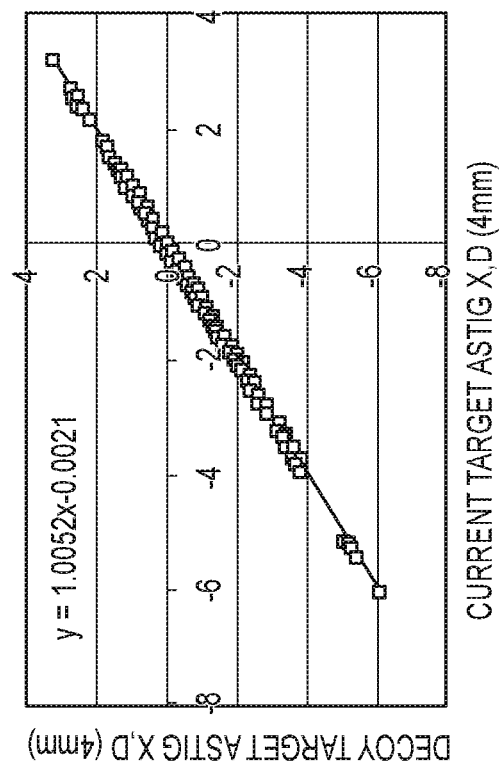

According to some embodiments, deconvolution may also affect the cylinder refraction. A magnitude of this effect is illustrated in FIGS. 12A and 12B. Here, it is possible to see a comparison of X, Y components of astigmatism for an original target and a deconvolved target (simulated for the studies, n=340). The deconvolved targets show slightly higher astigmatism, as compared with the original targets, although the difference is less than 1%.

According to some embodiments, a current or original target $T_{current}$ yields good matching to low order aberrations, and a scaling can be performed such that the refractive spherical equivalent over 4 mm of the new or modified target is the same as that of the current or original target. Exemplary studies have shown that such a scaling factor is about unity. Therefore, a scaling factor of 1.0 can be assumed in some cases.

Elevating Ablation Profile

As shown in FIG. 5, a method of modifying a target shape can also include elevating an ablation profile, as indicated by step 560. For example, in order to make all ablation values be non-negative, it is possible to elevate the entire ablation profile so that the lowest point on the ablation profile is zero or otherwise non-negative. In this way, the ablation profile can be generated so that it does not have negative heights.

Damping Periphery Of Transition Zone

As shown in FIG. 5, a method of modifying a target shape can also include damping a periphery of a transition zone, as indicated by step 570. For example, a damping multiplier or multiplication factor may be applied which suppresses the fluctuations of the periphery of the target shape. In some embodiments, after certain adjustments are made (e.g. such as the adjustment discussed above), a peripheral part of the ablation profile may have a small bump, which may be the result of a cut-off at the end of the transition zone. Ablating such a bump may require a sequence of many small laser pulses around the transition zone periphery. In some cases, this may cause a substantial reduction of speed in the entire ablation process. In some cases, the bump may not be needed because it lies away from the optical zone and its influence on the wavefront within the optical zone after smoothing may be very limited. Embodiments of the present invention encompass the application of a damping multiplier to the periphery of the transition zone, starting from the distance $R_b = R_{TZ} - 0.5$ mm, as follows:

$$T = T \cdot \begin{cases} \frac{R_{TZ} - R}{R_{TZ} - R_b} & R > R_b \\ 1 & R \leq R_b \end{cases}$$

Such a damping multiplier or factor can be used to eliminate or diminish the bump.

Figure 12C:
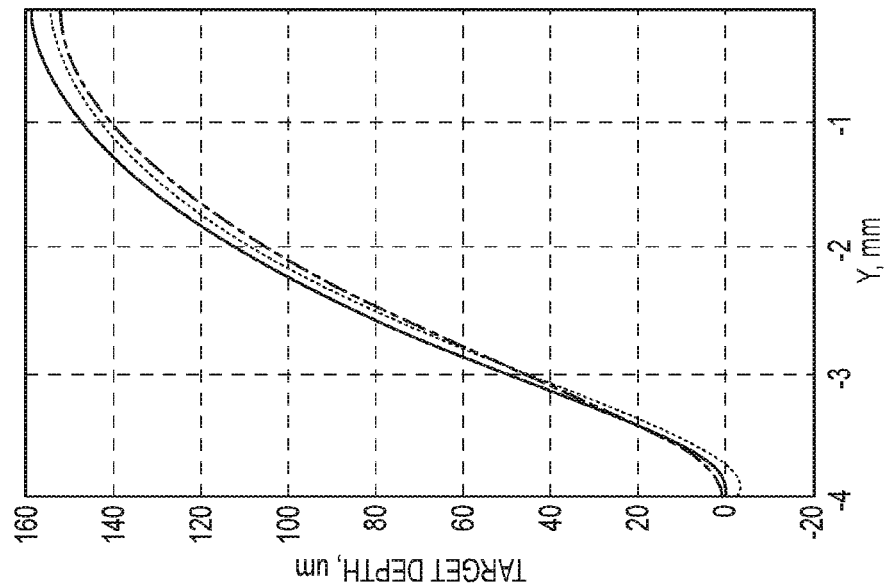
FIGS. 12C and 12D illustrate aspects of ablation profile modifications according to embodiments of the present invention.
Figure 12D:
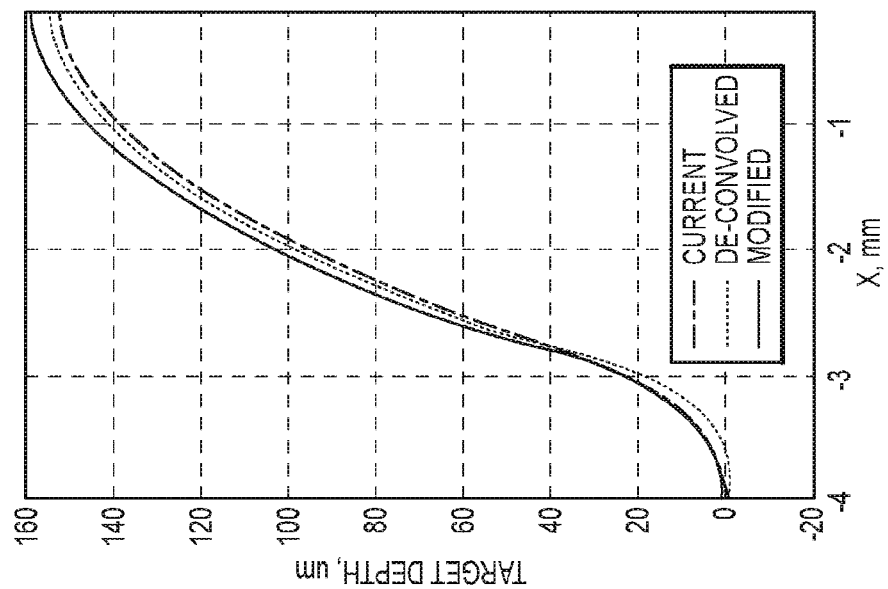

FIG. 12C shows an X cross-section of modifications of an ablation profile, and FIG. 12D shows a Y cross-section of modifications of an ablation profile. In some embodiments, modifications of an ablation profile (e.g. high myopia study, case ID=21011 OD) may include target deconvolution with σ=0.35 mm, as well as an elevation modification, or a cut-off beyond the transition zone.

Figure 13A:
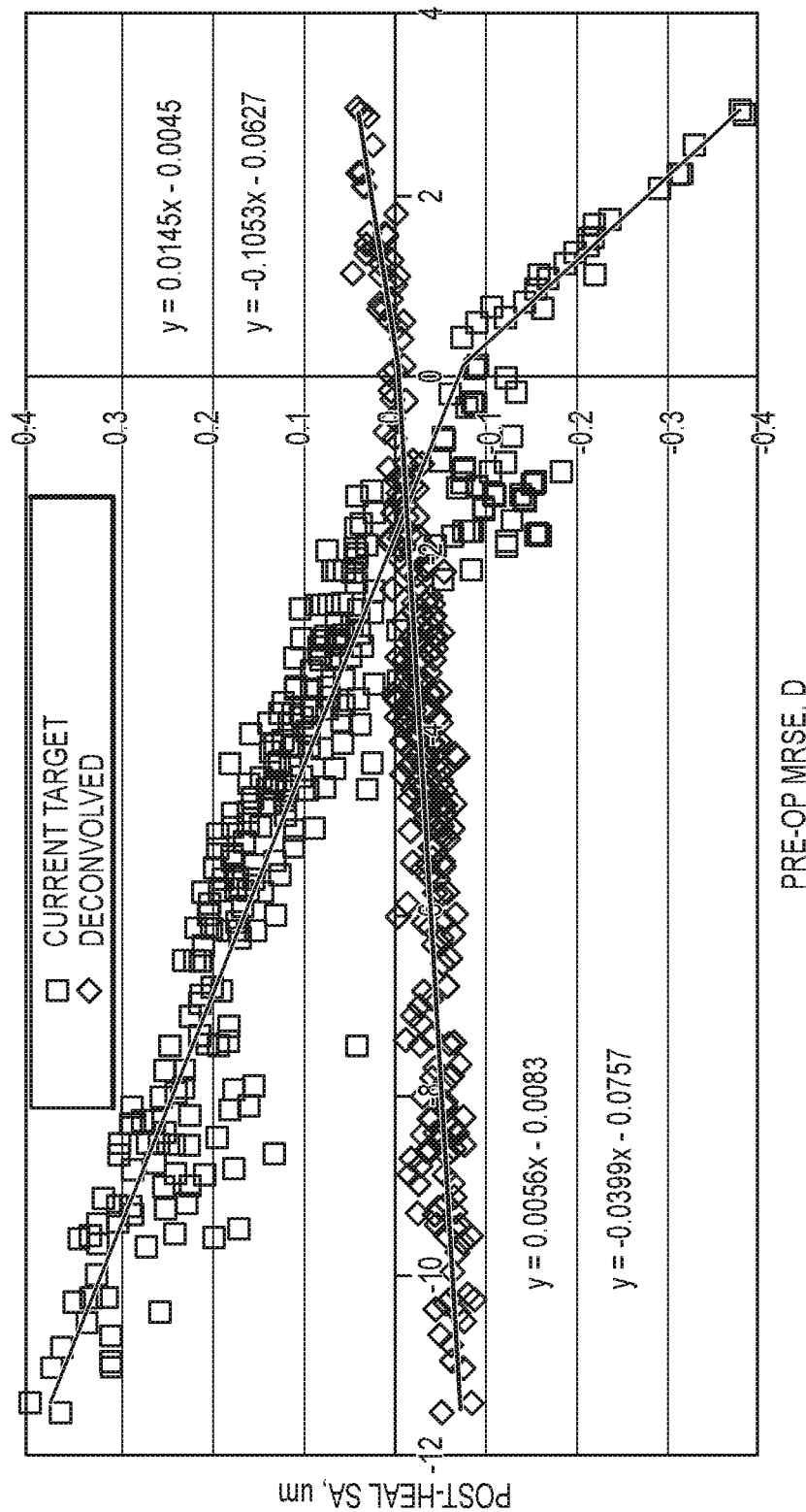
FIGS. 13A to 13C depict aspects of pre-operative MRSE (Manifest Refraction Spherical Equivalent) according to embodiments of the present invention.
Figure 13B:
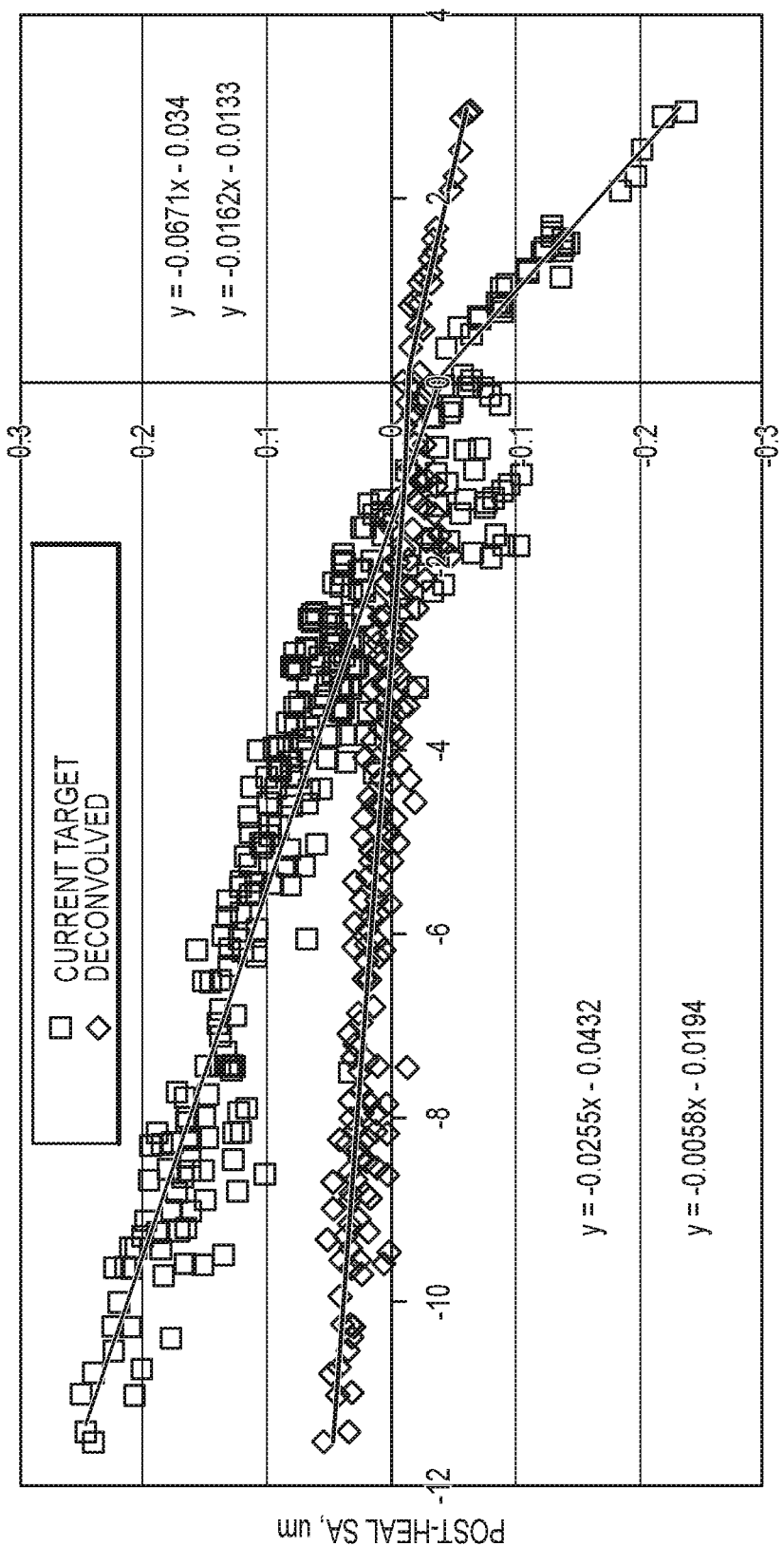
Figure 13C:
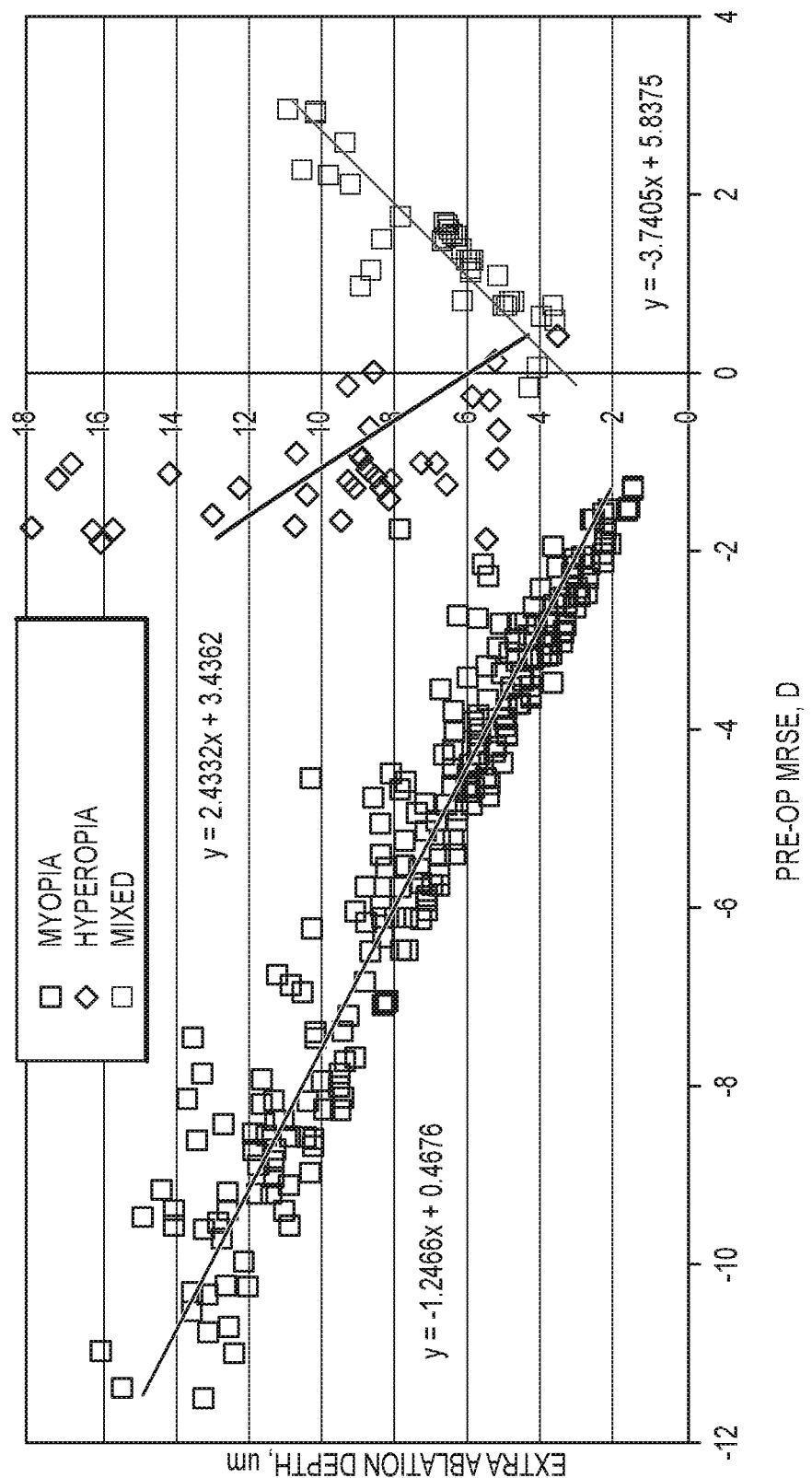

In some cases, a different wavefront diameter may use or benefit from a different diffusion coefficient (e.g. for an LPF model) to match post-operative measurements. In some cases, it is possible to use an approximated value of σ=0.35 mm, which is between optimized values for 6 mm and 5.5 mm wavefront diameters, as discussed elsewhere herein. Using a diffusion coefficient such as this for the target deconvolution, it is possible to predict or calculate a substantial reduction of induced SA for both WFD=6 mm and WFD=5 mm and also additional ablation depth requirement. For example, FIG. 13A depicts a simulated post-operative SA for a 6 mm wavefront, FIG. 13B depicts a simulated post-operative SA for a 5.5 mm wavefront, and FIG. 13C depicts an extra ablation that may benefit a deconvolved target. As such, these figures demonstrate the effect of deconvolution on post-smoothing SA and on additional maximum ablation depth.

Because deconvolution may amplify noises, the tail or outer periphery of the ablation profile may have some bumps. To remove such bumps, a damping multiplier can be applied as $$T' = T \cdot \begin{cases} 2(R_{TZ} - R) & R > R_b \\ 1 & R \leq R_b \end{cases} \quad \text{Equation 17}$$

where T' is the new target after damping, T is the target after Equation 14 and R is a variable in radius. $R_{TZ}$ is the transition zone radius, and the cutoff radius $R_b = R_{TZ} - 0.5$ mm. This damping multiplier can effectively and substantially eliminate the bumps.

Results and Data Analysis

Based on certain codes for treatment target creation, the following two phases of simulation studies were conducted. A first phase involved optimizing a one-parameter diffusion coefficient such that it best explains the clinically observed 6M post-operative spherical aberrations with the same surgical parameters as these eyes were treated. A second phase involved verifying that with the use of an optimized diffusion coefficient, the expected post-operative spherical aberration is significantly reduced when a deconvolution algorithm is used.

Optimization of a diffusion coefficient was based on data from various clinical studies and trials, as well as data from commercial sites. Only eyes with pre-operative and 6M (3M for iDesign™ system) post-operative wavefront measurements with at least 6 mm diameter were used. As such, 340 eyes were from the study, 169 eyes from the commercial sites, and 39 eyes from iDesign™ system based study. Of the 340 eyes from US IDE, 158 were in the low to moderate myopia cohort, 75 in the high myopia cohort, 26 from hyperopia cohort, 47 from the monovision cohort (dominant eyes only), and 34 from the mixed astigmatism cohort.

As explained elsewhere herein, a comparison between a simulated and an observed post-operative spherical aberration can be performed for a given diffusion coefficient. An optimization process was chosen such that the simulated post-operative spherical aberration has a substantially identical slope as compared with a pre-operative spherical equivalent to that of the observed post-operative spherical aberration.

Because of variations of the sample size in different cohorts, the 95% confidence bands are different for different cohort. A small overlap area can be identified for these 95% confidence bands. The optimized diffusion coefficient of 0.35 mm was obtained from the overlap area.

According to some embodiments, deconvolution, which can be used to reduce post-operative spherical aberrations, is a physical-model-backed approach. It is based on the smoothing effect observed from the clinical data. Therefore, not only can it account for the increase of the post-operative spherical aberration, but it can also account for the induction of other high order aberrations, such as coma, secondary astigmatism, and secondary spherical aberration. Furthermore, as discussed elsewhere herein, it provides a smaller ablation depth as compared with other techniques (e.g. larger optical zone, larger keratometric values) used to target the same level of spherical aberration reduction.

Many of the target shape modification discussed herein can operate to change a peripheral area of the target so as to reduce the induction of SA. It is possible to compare such methods, for example when their parameters are selected to generate a small slope of SA vs. SE trend, as indicated in Table 2. The parameters in this table were selected for the simulation to achieve a slope of SA vs. SE trend that is about the same as the slope from the observed clinical data.

TABLE 2

| | Modification parameter | SA vs. SE trend slope | $<SA>$ um | std(SA) um | max $|SA|$ um | $<extraH>$ um | max extraH um |
|---|---|---|---|---|---|---|---|
| Current target | | −0.04 | 0.16 | 0.16 | 0.58 | 0.0 | 0.0 |
| dOZ, mm | 0.4 | −0.01 | −0.01 | 0.10 | 0.31 | 11.02 | 26.0 |
| dK, D | 25 | −0.01 | −0.04 | 0.11 | 0.33 | 9.90 | 25.9 |
| sigma, mm | 0.35 | 0.01 | −0.03 | 0.09 | 0.29 | 7.24 | 17.9 |

Table 2 provides a comparison of three methods of target modifications, simulated for data from the studies. Parameters for each modification method were chosen to bring the magnitude of simulated slope of post-operative SA vs SE trend line down to 0.01. The simulated average post-op SA ($<SA>$), the worst case SA (max $|SA|$), the average extra ablation depth ($<extraH>$), and the worst case (max extraH) are also shown. Sigma ($\sigma$) is a diffusion coefficient related to the strength of an LPF process, described elsewhere herein. As shown in Table 2, a deconvolution method (sigma) can virtually eliminate both the mean SA and the SA vs. SE trend slope. Similarly, a widened optical zone method (dOZ) and a cosine correction adjustment method (dK) can also virtually eliminate both the mean SA and the SA vs. SE trend slope. Compared with widened optical zone and cosine adjustment methods, deconvolution techniques often require lower amounts of ablation, and hence can provide useful solutions where saving or maintaining more tissue is desired.

Figures 14A, 14B:
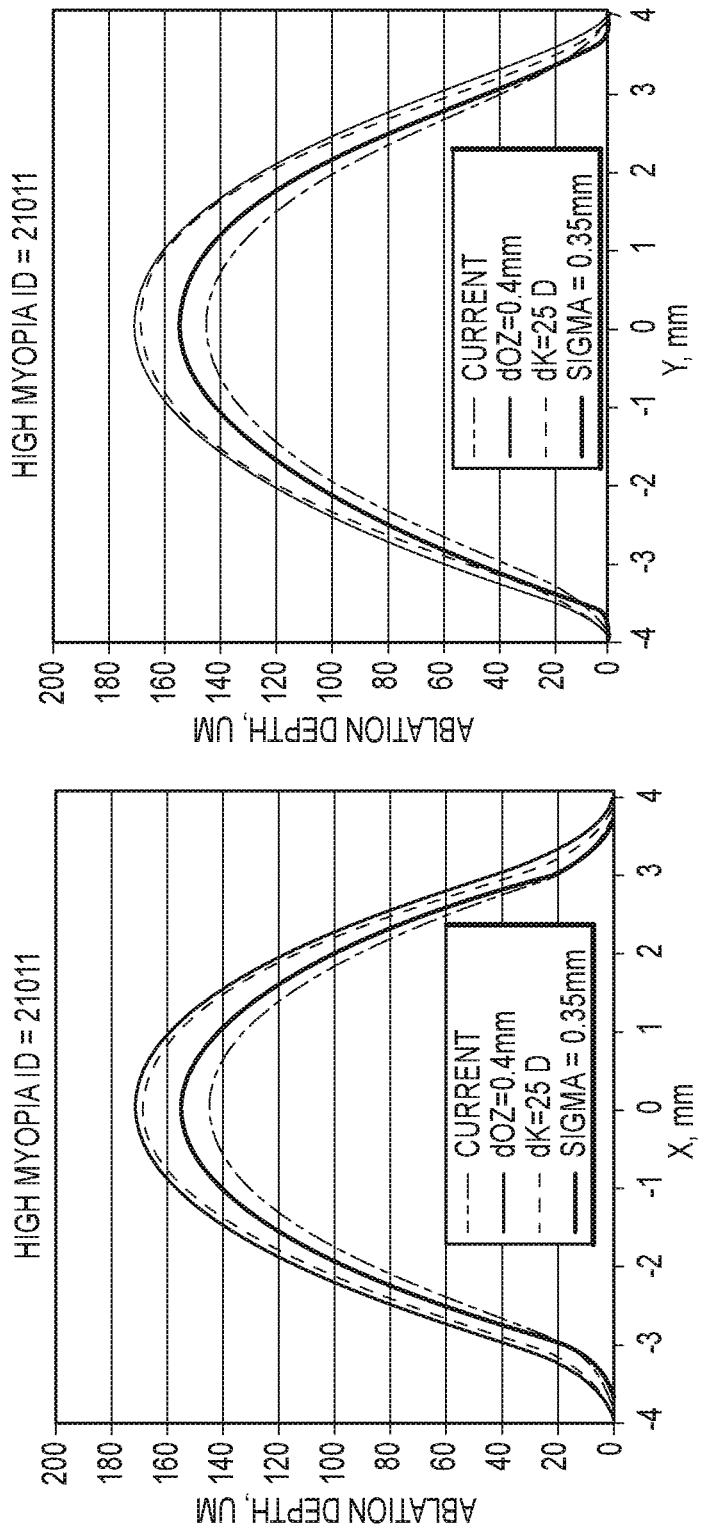
FIGS. 14A and 14B illustrate aspects of ablation profile modifications according to embodiments of the present invention.

FIG. 14A shows an X cross-section of modifications of an ablation profile, and FIG. 14B shows a Y cross-section of modifications of an ablation profile. These modifications of an ablation target are simulated for a high myopia study (study ID=21011 OD, −7.4 D/−1.5 D×179°). Simulation was performed for a wider optical zone approach (dOZ=0.4 mm), an adjusted cornea curvature for cosine correction approach (dK=25 D), and a deconvolution approach ($\sigma$=0.35 mm). When evaluating the expected post-operative SA, it may be helpful to consider that simulations may only show the changing SA vs SE trend line after the target modification. In reality the post-operative SA may deviate from the trend line due to some other factors which are not accounted for. These deviations can be estimated for the current target as follows:

$$\delta SA = SA_{observed}^{(6M)} - SA_{simulated}^{(post-op)} \qquad \text{Equation 18}$$

Figure 15A:
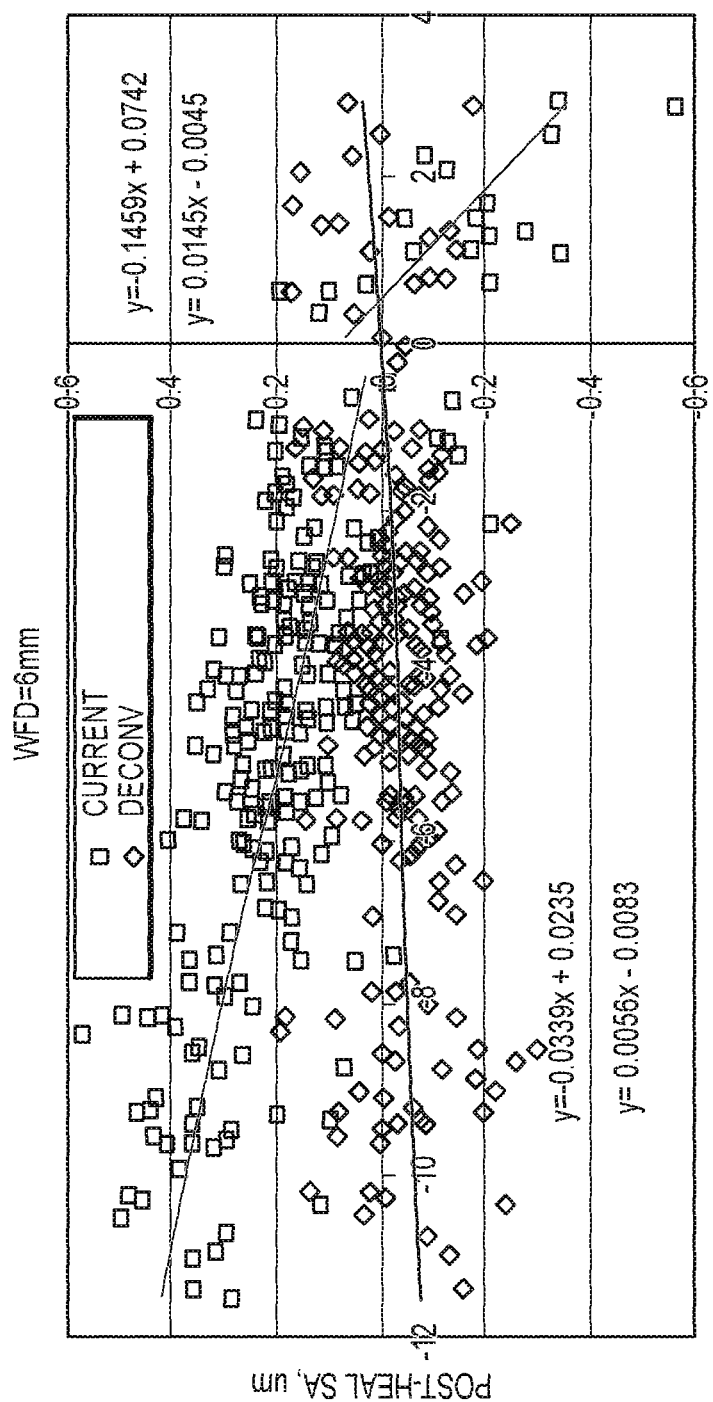
FIGS. 15A and 15B show aspects of pre-operative MRSE according to embodiments of the present invention.
Figure 15B:
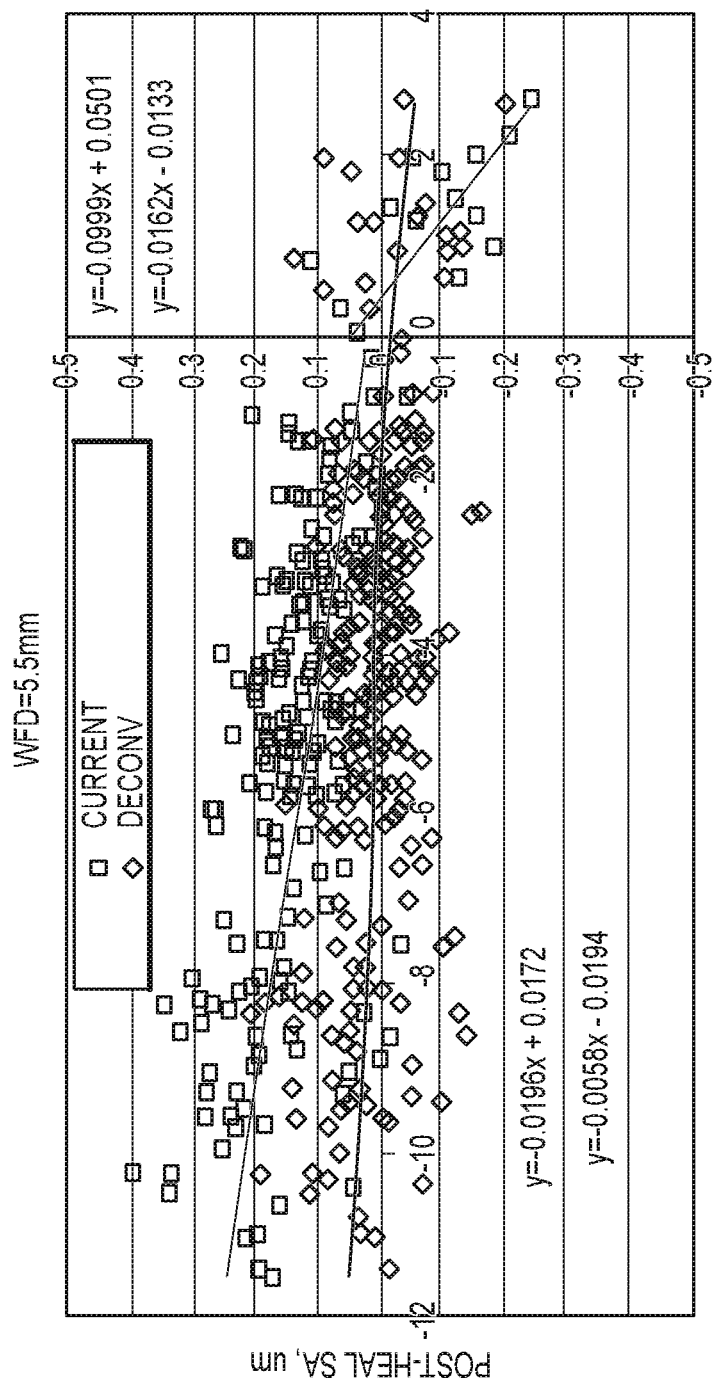

Assuming that the same deviations from the trend line can apply to a modified target, it is possible to add $\delta SA$ to the simulated post-operative SA values of every modified target, which can provide a realistic estimate of post-operative distribution of SA. For example, FIGS. 15A and 15B, depict post-operative SA for observed study data (n=340) and expected post-operative SA for de-convolved targets, simulated with $\sigma$=0.35 mm for the same eyes, for a 6 mm wavefront and 5.5 mm wavefront, respectively.

In addition to piston differences which may be present between the original and modified targets, there may be other shape differences as well. According to some embodiments, the following metrics can be used to compare shape differences:

$$\Delta = (H - \max(H)) - (H_{current} - \max(H_{current})) \qquad \text{Equation 19}$$

where H refers to ablation depth or target height.

Figure 16A:
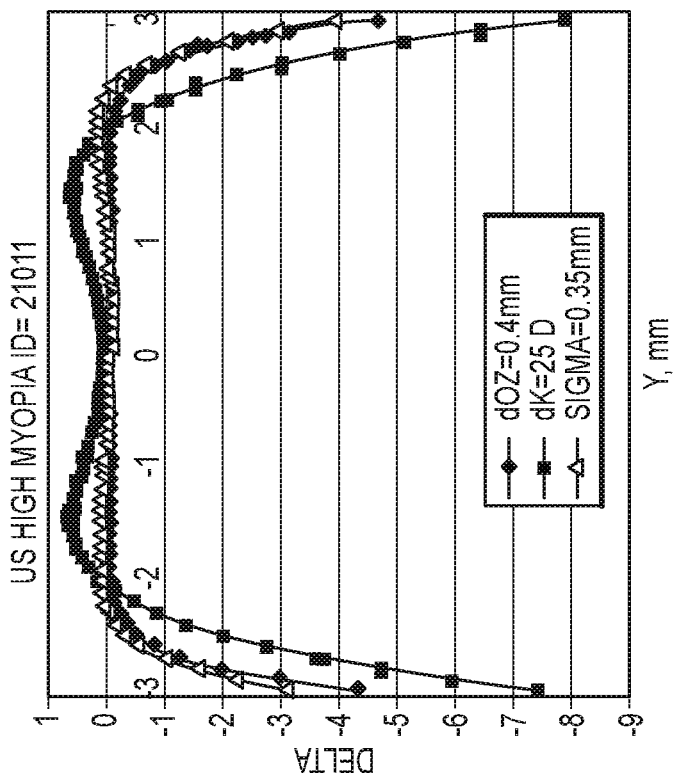
FIGS. 16A and 16B show aspects of differences between modified targets and original targets according to embodiments of the present invention.
Figure 16B:
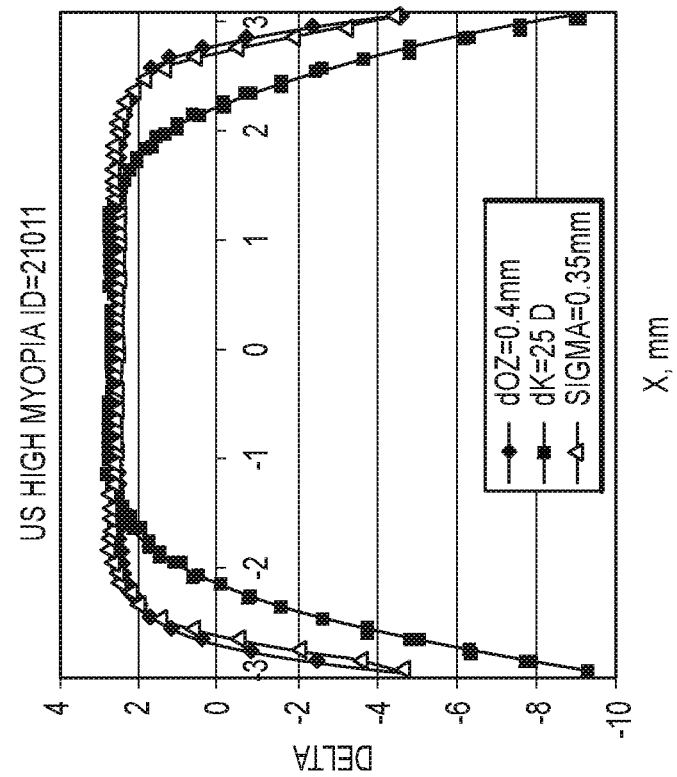

As illustrated in FIGS. 16A and 16B, target shapes subsequent to smoothing for two modification methods, namely widening optical zone (dOZ) and deconvolution (sigma) are almost identical within the 6 mm optical zone.

These figures show the differences (i.e. X and Y cross-sections, respectively) between a modified target and an original target, subsequent to smoothing, simulated for a high myopia case (ID=21011 OD, −7.4 D/−1.5 D×179°). Simulations were performed for a wider optical zone (dOZ=0.4 mm), an adjusted corneal curvature for cosine correction (dK=25 D), and a deconvolution ($\delta$=0.35 mm).

Figure 17:
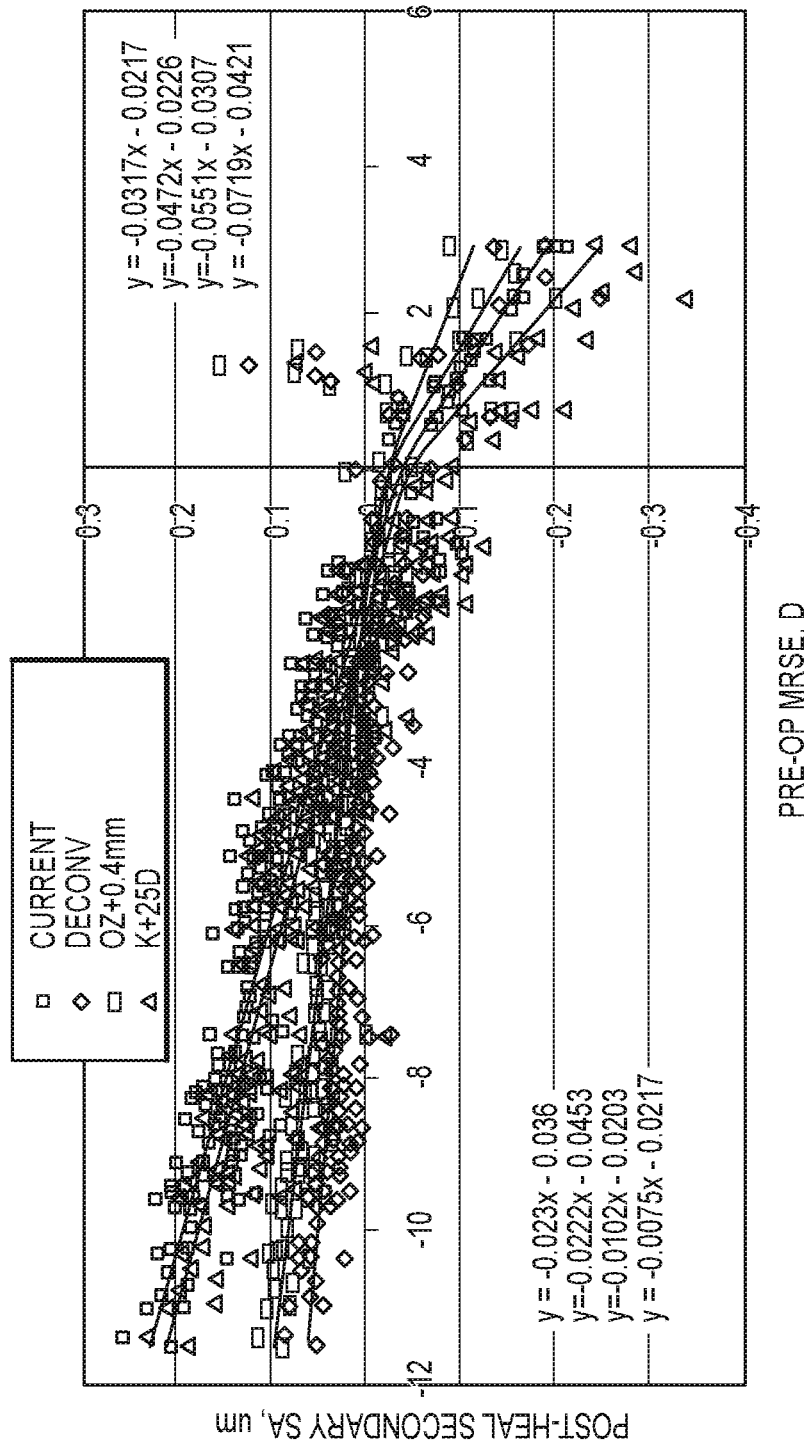
FIG. 17 depicts aspects of shows post-operating secondary spherical aberration according to embodiments of the present invention.

A cosine adjustment can make a different shape with a substantially higher secondary spherical aberration, as depicted in FIG. 17. In some cases, software or systems may allow both a user-defined optical zone and a user-defined adjustment of corneal curvature (e.g. defining the cosine correction), and these two adjustments can be used for validation for a deconvolution technique. In some cases, a wider optical zone, may provide a closer approximation than a curvature adjustment. FIG. 17 shows a post-operating secondary spherical aberration (WFD=6 mm), simulated for study data (n=340). Simulation was performed for original targets and for modified targets with a wider optical zone (dOZ=0.4 mm), an adjusted corneal curvature for cosine correction (dK=25 D), and a deconvolution ($\sigma$=0.35 mm).

In sum, the three methods for modification of an ablation target (widening optical zone, adjusting cosine correction, and deconvolution) are capable of eliminating a systematic trend in post-operatively induced spherical aberration. As shown here, the ablation profiles for these modifications can present different depths, and deconvolution can provide a technique which results in a maximum of tissue retention. That is, the amount of ablation associated with deconvolution is smaller than that of the other methods. In some instances, widened optical zone and deconvolution techniques may yield almost identical corneal shapes after smoothing. In some cases, a widened optical zone technique (e.g. based on a user-defined optical zone) may be used as a validation for a deconvolution technique.

Treatment Target Creation

Figure 18:
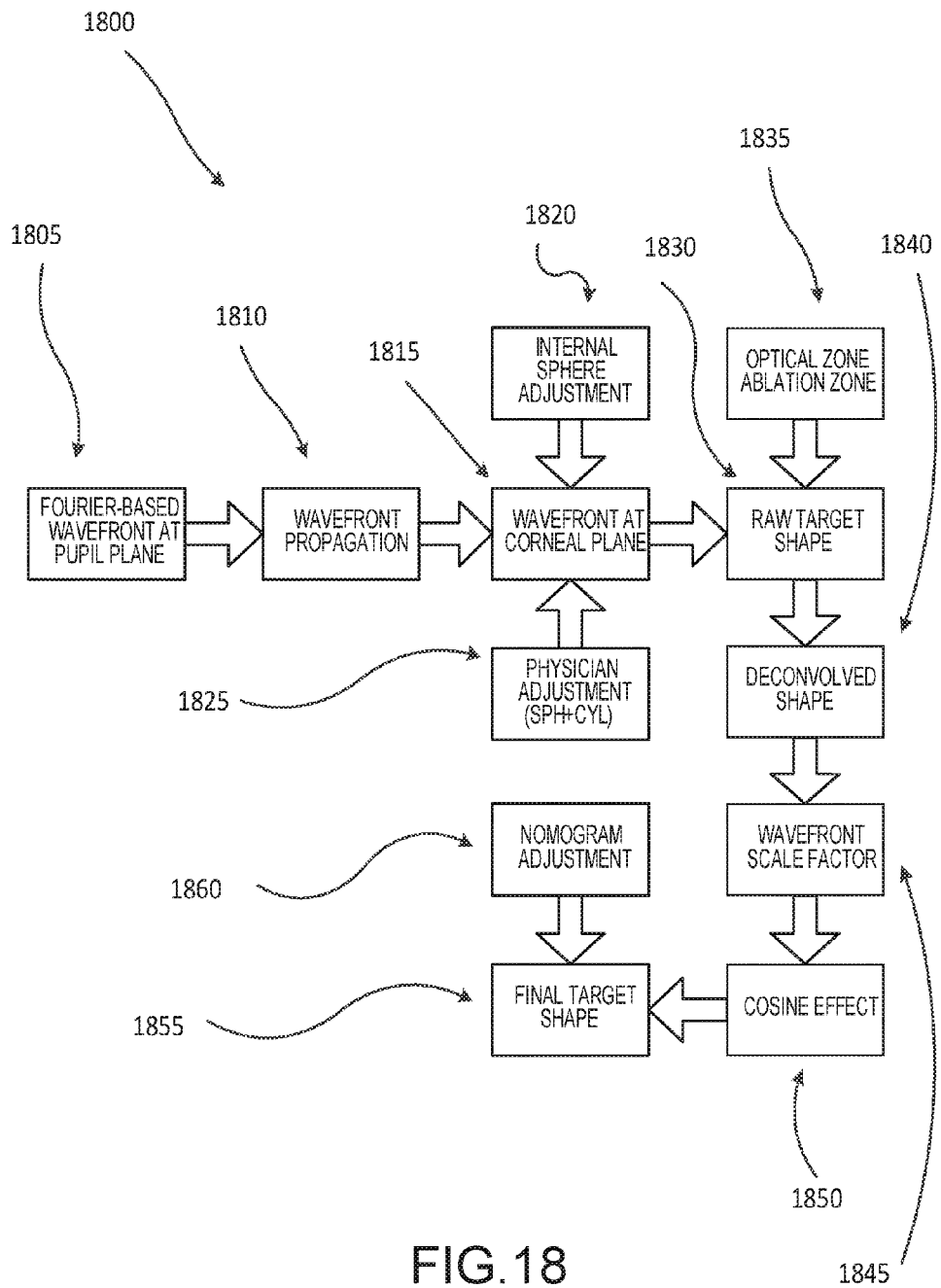
FIG. 18 depicts aspects of methods for generating a target shape, according to embodiments of the present invention.

As noted elsewhere herein, a treatment target shape may represent or correspond to an intended optical surface that is designed to achieve a particular refractive correction. FIG. 18 depicts a method 1800 for generating a target shape, according to embodiments of the present invention. Method 1800 may include obtaining a wavefront corresponding to a pupil plane, as indicated by module 1805. For example, for target creation, the input can be a Fourier-based wavefront, which represents the ocular aberrations on the pupil plane. Typically, a laser ablation is performed on the corneal surface, and hence to obtain the target shape the ocular aberrations are propagated from the pupil plane to the corneal surface. Accordingly, methods may include propagating the wavefront, as indicated by step 1810, and obtaining a wavefront corresponding to a corneal plane, as indicated by step 1815. Any physician adjustments or nomogram adjustments can also be represented on the corneal surface first before they are combined with the ocular aberrations. Hence, the process of obtaining a wavefront at the corneal plane may also be based on an internal sphere adjustment, as indicated by step 1820, or on a physician adjustment (e.g. Sph+Cyl), as indicated by step 1825, or both.

In some instances, parameters such as optical zone size and the ablation zone size, which may be user-defined, can be used to determine the ablation or target shape within such zones. Thus, the process of obtaining a raw or original target shape, as indicated by step 1830, may be based on a selection or definition of an optical zone, an ablation zone, or both, as indicated by step 1835.

A deconvolution technique can be used to deconvolved the raw or original shape, so as to obtain a deconvolved shape, as indicated by step 1840. Such a deconvolution can operate to reduce post-operative spherical aberration. Once the deconvolved shape is obtained, a scaling factor can be applied, as indicated by step 1845, and a cosine effect modification that compensates for the loss of energy due to the curved cornea can be applied, as indicated by step 1850. Hence, the final target shape can be determined based on the deconvolved shape, as indicated by step 1855, optionally considering a scaling factor, a cosine effect, or both.

In some instances a nomogram adjustment can be applied, as indicated by step 1860, when obtaining the final target shape. Following creation of the final or modified target shape, as indicated by step 1855, the target shape can be transmitted to a treatment table generation engine.

Exemplary Techniques for Target Shape Deconvolution

As explained elsewhere herein, treatment target shapes can lead to induced aberrations, and deconvolution can be applied to such treatment target shapes so as to reduce or inhibit the induced aberrations.

Figure 20:
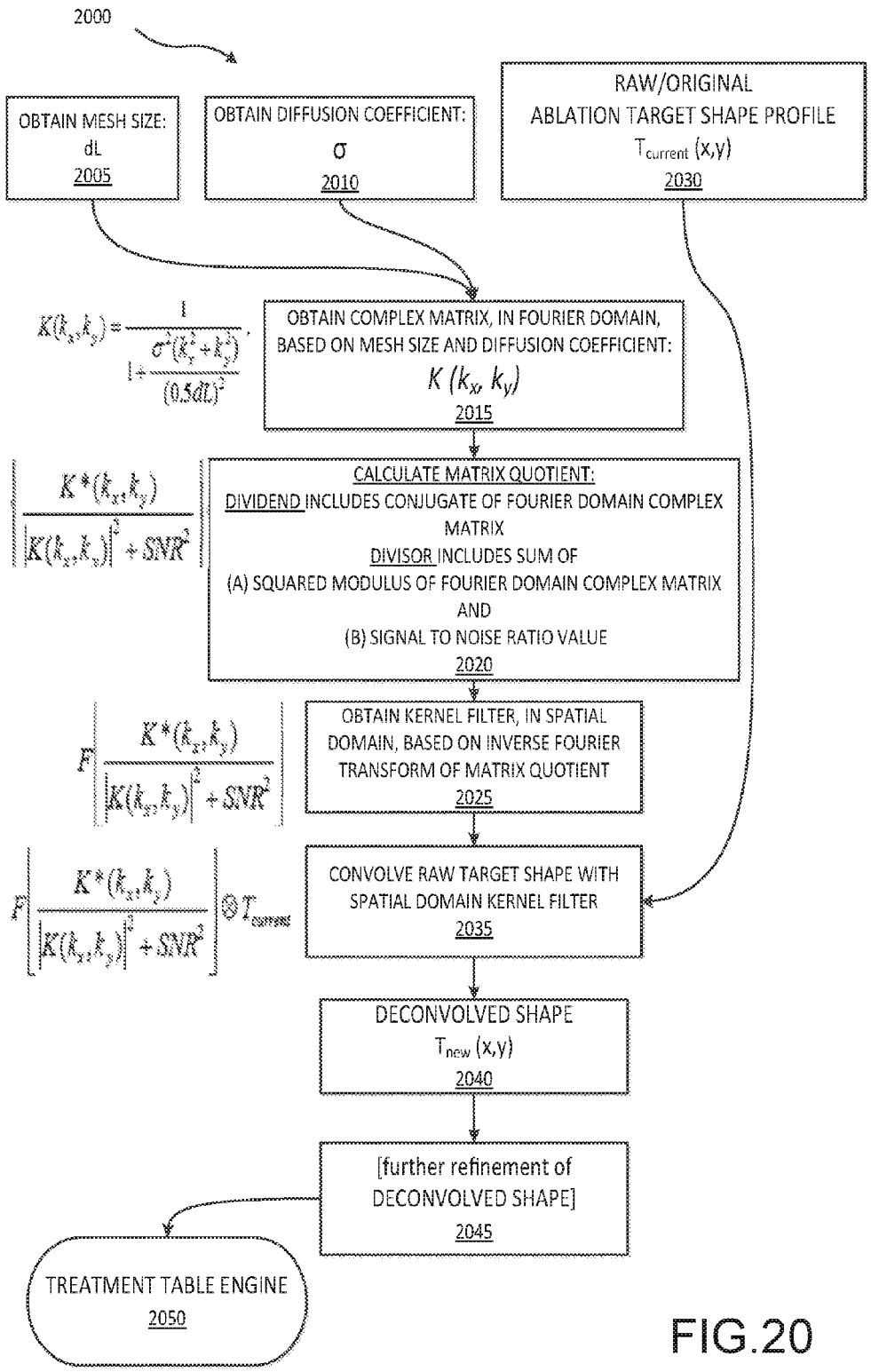
FIG. 20 illustrates aspects of deconvolution methods according to embodiments of the present invention.

FIG. 20 depicts aspects of a deconvolution method 2000 for a target shape, according to embodiments of the present invention. As illustrated here, method 2000 of deconvolving a target shape may include obtaining a mesh size as indicated by step 2005 and obtaining a diffusion coefficient as indicated by step 2010. Method 2000 may also include obtaining a complex matrix, in Fourier domain, based on a mesh size and diffusion coefficient as indicated by step 2015.

Complex Matrix

According to some embodiments, a complex matrix $K(k_x, k_y)$ can be applied to a treatment target to obtain a wavefront change due to corneal smoothing The complex matrix can be considered to represent a three dimensional matrix in a Fourier or frequency domain. In some cases, the complex matrix may be a squared Butterworth low-pass filter of the first order. Other types of low-pass filters may be suitable for use with embodiments of the present invention. In some cases, a low-pass filter may refer to a function or operation that makes details smoother by suppressing high spatial frequency information.

In some instances, the Fourier domain complex matrix can be expressed as follows:

$$K(k_x, k_y) = \frac{1}{1 + \frac{\sigma^2(k_x^2 + k_y^2)}{(0.5dL)^2}} \quad \text{Equation 20}$$

where $\sigma$ represents a diffusion coefficient, $k_x$ and $k_y$ represent frequency domain variables, and dL represents a mesh size. Optionally, the diffusion coefficient $\sigma$ can have a value of 0.35 mm and the mesh size dL can have a value of 0.1 mm. In some instances, the diffusion coefficient can have a value with a range from about 0.2 to about 0.5 (see, e.g. FIG. 8A). In some instances, the diffusion coefficient can have a value with a range from about 0.33 to about 0.4 (see, e.g. FIG. 33).

In some instances, the term Fourier transform as used herein may refer to a transform operation. In some instances, the term Fourier transform as used herein may refer to a complex valued function produced by a transform process.

Mesh Size

In an exemplary discrete case, a complex matrix $K(k_x, k_y)$ can be based on a 101×101 mesh size of dL=0.1 mm. Often, such matrix formats (e.g. 101×101) are used when characterizing treatment planning. In some cases, a mesh size or dL may refer to the spacing or spatial distance between two neighboring pixels. In some cases, dL may refer to the pixel resolution in the kernel, which can be 101×101 in pixel frame size or 10 mm×10 mm in space. When a discrete Fourier transform is involved, it is possible to represent the frame in 101×101, although it may no longer be 0.1 mm because it is in frequency domain (more like cycles per degree). Hence, dL may involve a 0.1 mm spacing in the spatial domain.

In some instances, selection of a kernel or matrix format may represent a balance between accuracy and speed concerns. For example, a larger kernel or matrix format such as 101×101 may provide greater relative accuracy and lower relative speed, whereas a smaller kernel or matrix format such as 25×25 may provide lower relative accuracy and greater relative speed.

Diffusion Coefficient

As noted above, a complex matrix can also be based on a diffusion coefficient $\sigma$. Typically, a diffusion coefficient $\sigma$ has a unit of length. This parameter can describe the strength of corneal smoothing during and after a refractive surgical procedure, and as such can be considered as a biologically related parameter. The parameter can be used to characterize a single individual, or a group of individuals. Based on the analysis of results from several clinical trials, it has been discovered that a diffusion coefficient $\sigma$ of 0.35 mm is consistent with such observed data. In some instances, a diffusion coefficient can have a value within a range from about 0.2 mm to about 0.5 mm. In some instances, a diffusion coefficient can have a value of about 0.3 mm.

Because a Fourier domain complex matrix can be based on the mesh size, the diffusion coefficient, or both, it follows that a corresponding spatial domain kernel filter, as discussed elsewhere herein can also be based on the mesh size, the diffusion coefficient, or both.

According to some embodiments, an LPF can be used to emulate the diffusion of corneal tissue cells. Exemplary techniques may involve estimating or receiving a diffusion coefficient value, and using that value to effect a compensation for a high order aberration before administering a treatment such as a laser vision corrective procedure. By pre-compensating for high order aberrations, it is possible to obtain an outcome with a reduced amount of high order aberrations.

Diffusion coefficients may be evaluated based on simulations. For example, a diffusion coefficient σ value can be selected for application to clinical data in a deconvolution procedure as described herein, and the expected outcome (e.g. deconvolved target shape) can be compared to the actual outcome (e.g. clinical data). The diffusion coefficient can be adjusted or optimized so as to reduce or minimize variance or a standard deviation in the comparison results. Exemplary adjustment or optimization techniques are described elsewhere herein, for example in connection with FIGS. 25 to 28A.

Relatedly, embodiments encompass systems and methods for adjusting refractive surgery parameters, which may include a diffusion coefficient, for use in a vision treatement. An exemplary method may include inputting or receiving a refractive case, determining a model optical surface shape based on the refractive case and a set of refractive surgery system parameters, comparing the refractive case and the model optical surface shape to determine an aberration induced by the set of refractive surgery system parameters, adjusting the set of refractive surgery system parameters so as to inhibit the induced aberration, and administering the refractive treatment to a patient. The refractive treatment can be based on the adjusted set of refractive surgery system parameters.

Matrix Quotient

As depicted by step 2020, methods may include calculating a matrix quotient, where the dividend includes a conjugate of a Fourier domain complex matrix (e.g. $K^*(k_x, k_y)$), and the divisor includes the sum of a squared modulus of the Fourier domain complex matrix and a signal to noise ratio value. In some cases, the signal to noise ratio value may be a squared value. An exemplary matrix quotient can be expressed as follows:

$$\left[\frac{K*(k_x, k_y)}{|K(k_x, k_y)|^2 + SNR^2}\right], \quad \text{Equation 21}$$

In some cases, the denominator or divisor of the matrix quotient can be characterized at least in part by the expression $|K(k_x, k_y)|^n$, where n is an integer having a value of 2 or more. In some cases, the denominator or divisor of the matrix quotient can be characterized at least in part by the expression $[|K(k_x, k_y)|^n + SNR^2]$ where n is an integer having a value of 2 or more and SNR represents a signal to noise ratio value. Equation 21 may refer to a filtering process that is in the frequency domain. A complex conjugate may be part of the filtering process.

Spatial Domain Kernel Filter

As depicted by step 2025, methods may also include obtaining a kernel filter, in the spatial domain, based on an inverse Fourier transform of the matrix quotient. An exemplary kernel filter can be expressed as follows:

$$F\left[\frac{K*(k_x, k_y)}{|K(k_x, k_y)|^2 + SNR^2}\right] \quad \text{Equation 22}$$

In some cases, the kernel filter of Equation 22 can be provided as a pre-calculated or pre-defined matrix, and can be used or saved as a lookup table. As discussed elsewhere herein, this kernel filter can also be referred to as an inverse kernel $K_{INV}$. Optionally, this kernel filter can be referred to as $K(x, y)$. This spatial domain filter or inverse kernel can also be provided as a low pass filter, such as a Butterworth or Gaussian filter. Optionally, the spatial domain kernel filter can present a grid or matrix that reflects how the filtered value of a pixel depends on neighboring pixel values, and is independent of the target shape.

Convolving Raw Target

As depicted by step 2035, methods may include convolving a raw or original target shape with the spatial domain kernel filter. Optionally, methods may include receiving, at an input, an original target profile or shape for the eye of the patient, as indicated by step 2030. As shown here, the spatial domain kernel filter can be based on an inverse Fourier transform of a Fourier domain noise filter, for example, which may be based on a conjugate of a Fourier domain complex matrix, on a modulus of a Fourier domain complex matrix, or on a combination thereof. In some instances, a Fourier domain noise filter can be characterized by fraction having a numerator comprising a conjugate of a Fourier domain complex matrix and a denominator comprising a modulus of the Fourier domain complex matrix. Method 2000 indicates that an original target shape $T_{current}(x, y)$ can be convolved with a spatial domain kernel filter so as to obtain a deconvolved shape $T_{new}(x, y)$, as indicated by step 2040. In some instances, the deconvolved shape 2040 emphasizes curvature changes, or corners, sharp edges, sharp transitions, and the like. In some cases, methods may involve the application of a low pass filter deconvolution to a target profile having a slightly extended optical zone. In some instances, parameters of a low pass filter can be optimized by comparing an LPF model prediction against observed clinical data.

Other Refinements

As depicted by step 2045, methods may include additional refinements of a shape prior to transmitting the shape to a treatment table engine. For example, a convolved profile may include a transition zone radius, and exemplary techniques may include zeroing the convolved profile at locations outside of the transition zone radius. In some cases, an original target profile may have an original refractive spherical equivalent value within a 4 mm diameter area, and the convolved target profile may have a target refractive spherical equivalent value within a 4 mm diameter area, and method 2000 may include scaling the original refractive spherical equivalent with the target refractive spherical equivalent value. In some cases, methods may include elevating the convolved profile so that a lowest point on the convolved profile is zero or greater. In some cases, a convolved profile may include a transition zone radius, and methods may involve applying a damping multiplier at or near the transition zone radius. In some instances, refinement can be performed prior to, or subsequent to, deconvolution, with an equivalent effect.

As discussed elsewhere herein, a deconvolved target may have an oscillating profile at the periphery. Such oscillations may be caused by boundaries between the optical zone, transition zone, and edge of the finite-size target, where either the target profile or its derivatives have sharp changes. In some instances, it may be helpful to elevate the entire ablation profile so that the lowest point on the ablation profile is zero, or so that all ablation values are non-negative. What is more, it may be helpful to zero-out the ablation profile at distances greater than the transition zone radius, $R_{TZ}$, where no ablation is desired beyond the end of the transition zone. Such refinements are illustrated in the X and Y target cross-sections of FIG. 21A, which depicts modifications of an ablation profile (high myopia study, case ID=21011 OD) including deconvolution (σ=0.28 mm), elevation, and cut-off beyond the transition zone. In some cases, after such refinements or adjustments are made, only the peripheral curvature will be changed, for example as depicted in FIG. 21B, which shows a change of ablation profile after target deconvolution (High Myopia study, case ID=21011, OD, −7.4 D/−1.5 D×179 deg).

In some instances, an original target shape may operate to effectively address refraction errors, and hence it may be desirable to maintain the refraction of the modified target at the same value as the refraction of the original target. This can be done with rescaling of the deconvolved target so that its defocusing term within the 4 mm area is the same as for the original target.

Figure 21A:
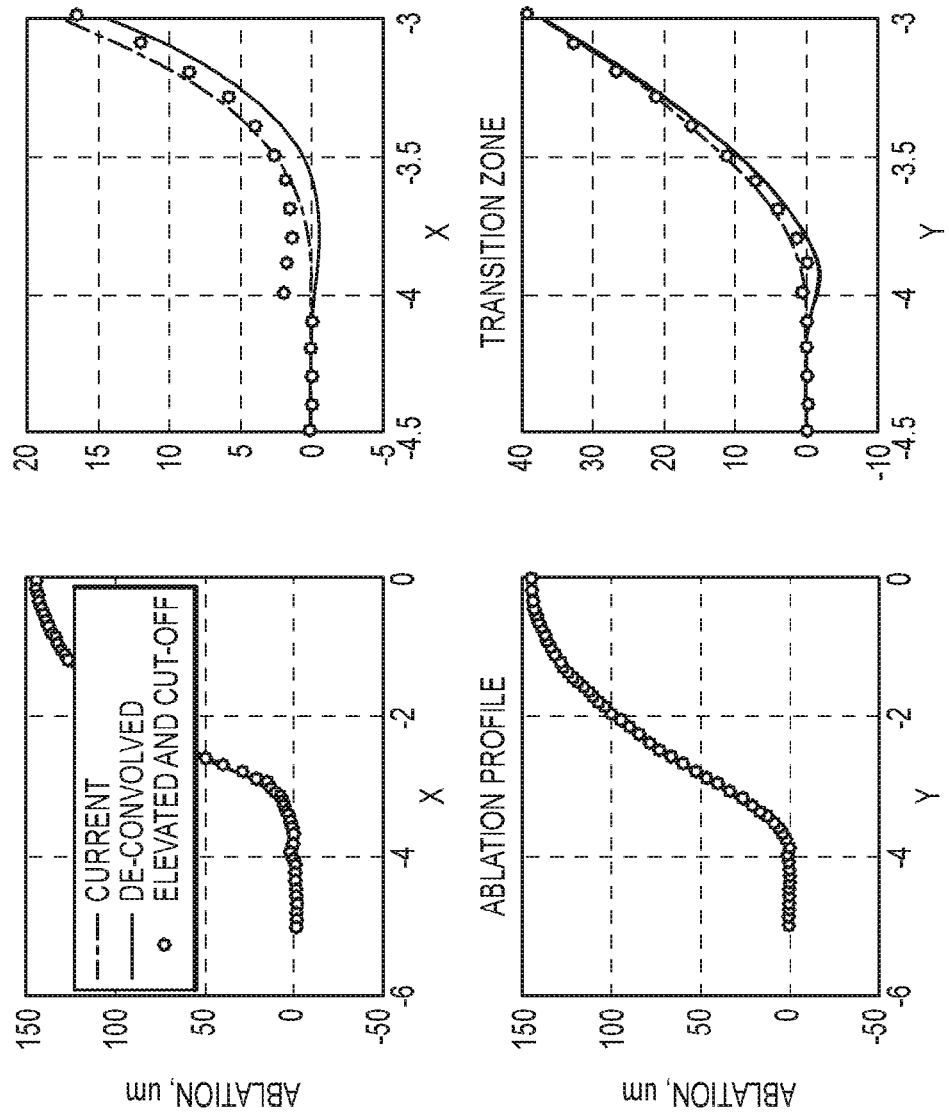
FIGS. 21A and 21B show aspects of ablation profile changes or modifications according to embodiments of the present invention.
Figure 21B:
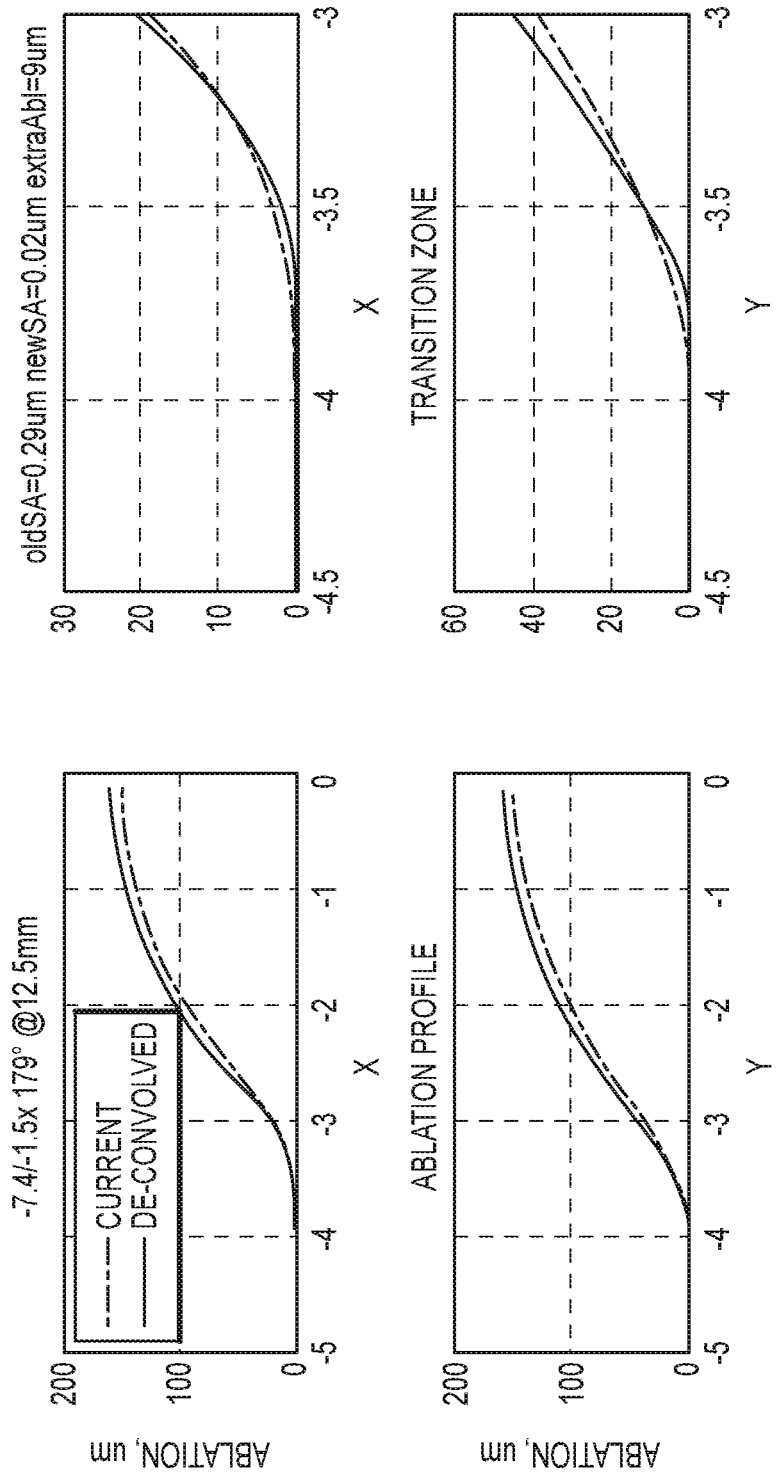

In addition to, or following some or all of the above mentioned adjustments, the peripheral part of the ablation profile may have a small bump, which results mainly from the cut-off at the end of the transition zone, for example as depicted in FIG. 21A. Ablating such a bump may involve application of a sequence of many small laser pulses around the transition zone periphery. In some instances, this may lead to a substantial slow-down of the entire ablation process. Yet this bump may be unnecessary, because it lies away from the optical zone and its influence on the wavefront within the optical zone shall be rather small after healing. With this consideration, it is possible to apply a damping multiplier to the periphery of the transition zone, as described elsewhere herein.

Spherical Aberration and Related Topics

As discussed elsewhere herein, spherical aberration (SA) may be induced by a target shape, a healing effect, or a combination thereof. In some cases, it is possible to reduce or even completely eliminate target-induced SA by implementing a small offset of the transition zone. In some original target shapes, the inner boundary of the transition zone is located within the optical zone, e.g. at about 0.25 mm from the edge of the optical zone. In addressing target-induced SA, it may be helpful to shift the transition zone boundary, by moving it farther from the center of the optical zone. In this way, the target-induced SA can be decreased, although squeeze the transition zone and cause sharper gradients in the peripheral target. In some instances, this may mean there will be a narrower transition zone band. In some instances, shifting the thegg inner boundary of the transition zone away from the center of the optical zone by a distance of about 0.1 mm can operate to reduce the target-induced SA to a level below 0.1 um, which may be considered negligible.

Figure 22:
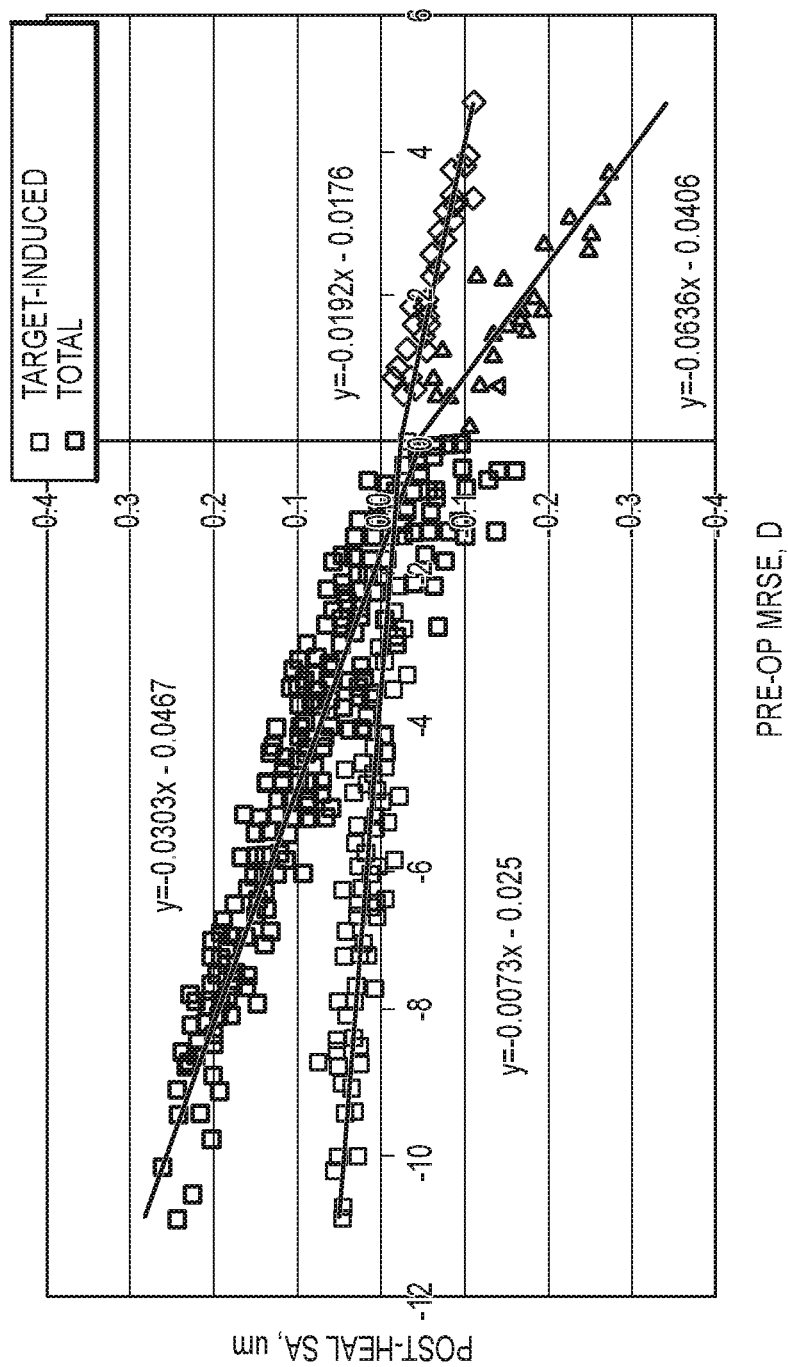
FIG. 22 illustrates aspects of induced SA according to embodiments of the present invention.

FIG. 22 shows a simulated induced SA immediately after ablation (target-induced) and after healing (total) for a target with an inner boundary of the transition zone shifted outward by 0.1 mm, using a healing model where σ=0.28 mm. As shown here, after healing, the total SA reached a level of about 0.3 um.

In order to compensate for the spread of the high curvature, which is a main cause of post-healing induced SA, it is helpful to apply a deconvolution transformation to the original target. In some cases, the LPF core for deconvolution is the same as the one optimized to fit observed induced post-operative SA. Then healing, simulated as convolution with the same LPF core, can bring the healed cornea back to the desired shape.

FIG. 23 shows the effect of deconvolution on post-healing SA (left panel) and additional maximum ablation depth (right panel) simulated with σ=0.28 mm for studies (n=515).

Relatedly, Table 3 shows simulated changes in post-healing SA and extra ablation, caused by deconvolution and additional adjustments of an original target. Statistics for studies: Myopia and High Myopia (n=327), Hyperopia (n=43), and all studies together (n=515).

TABLE 3

|  | old SA(SE) Slope | new SA(SE) Slope | <SA> | max \|SA\| | <extra Abl> | max extAb |
|---|---|---|---|---|---|---|
| Myopia & HM | −0.04 | −0.01 | 0.01 | 0.08 | 4.3 | 8.9 |
| Hyperopia | −0.09 | −0.02 | −0.05 | 0.11 | 3.5 | 7.6 |
| All US IDE | −0.04 | −0.01 | 0.00 | 0.11 | 4.2 | 9.9 |

Figure 24:
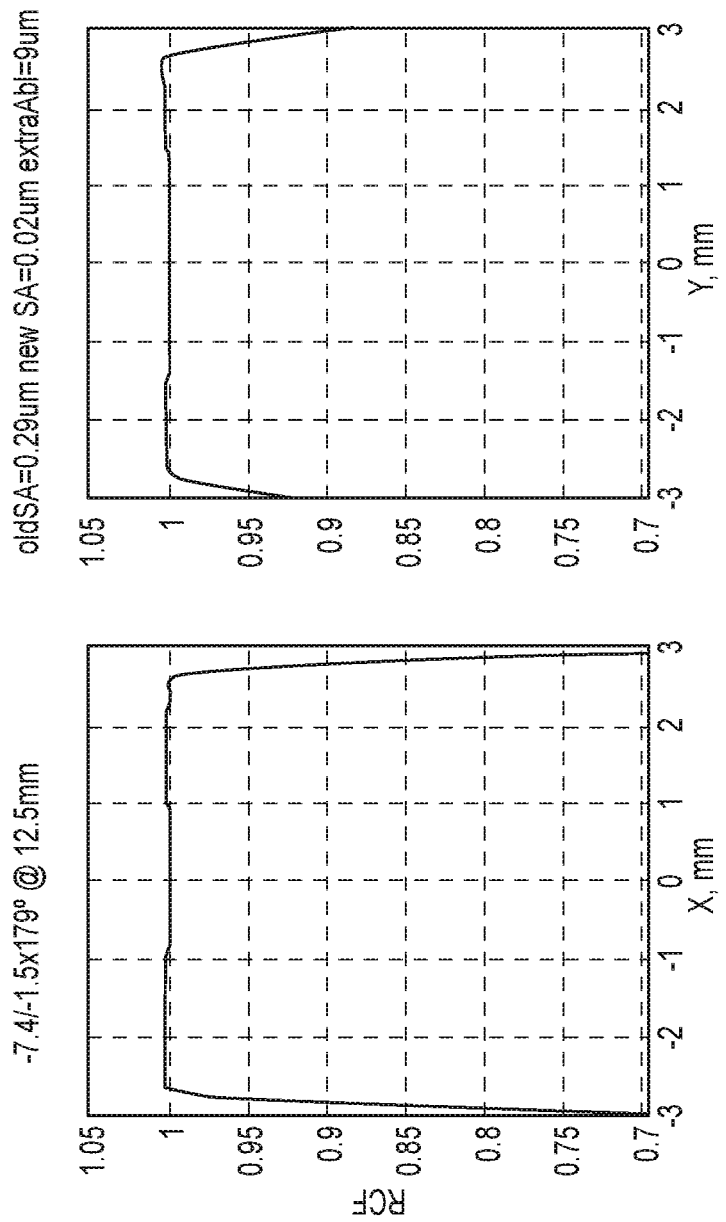
FIG. 24 illustrates aspects of radial compensation function according to embodiments of the present invention.

FIG. 24 depicts a radial compensation function (RCF) for a deconvolved target in a high myopia case, according to embodiments of the present invention. Specifically, a radial compensation function was calculated for a deconvolved target corresponding to a High Myopia study (case ID=21011 OD, −7.4 D/−1.5 D×179 deg.). As shown here, the RCF is almost flat in the central part and decreases in the periphery.

Figure 25:
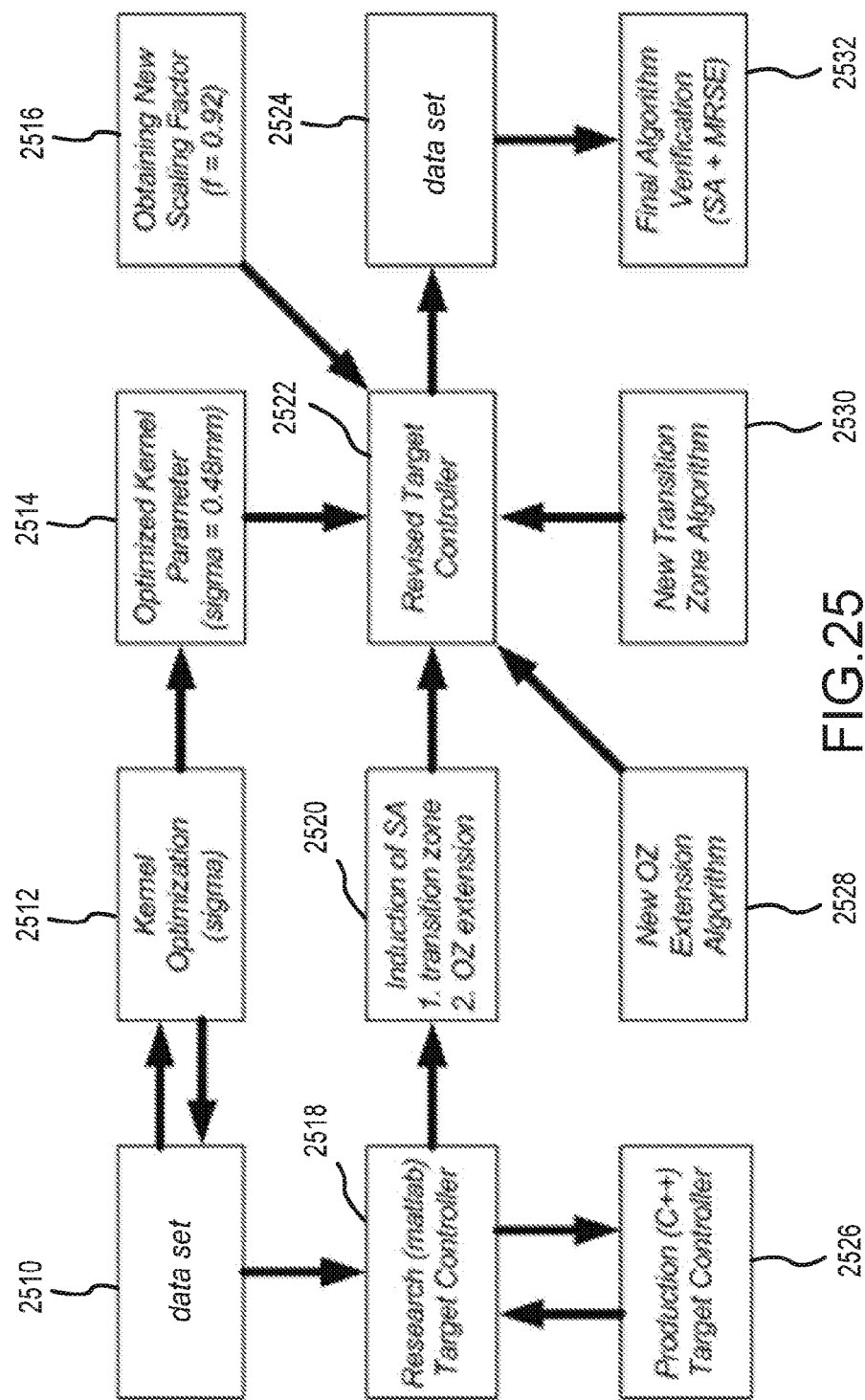
FIG. 25 illustrates aspects of target shape modification according to embodiments of the present invention.

FIG. 25 schematically illustrates techniques for obtaining and implementing a modified target shape, according to embodiments of the present invention. As shown here, study data can be used to derive parameters of a kernel for simulating a low-pass filtering process, for corneal healing and the like. Embodiments may also include optimizing the parameters by using a clinical data set. These techniques may also involve evaluating the extent to which observed spherical aberration is attributed to error, due to an imperfect optical treatment shape. In some instances, methods may also include addressing target shape induced SA by providing transition zone adjustments, optical zone extension adjustments, or both. In some cases, a deconvolution (e.g. inverse of low pass filter) may boost the total treatment depth. Techniques may also involve running a revised target controller (e.g. without a cosine effect) with a low-pass filter, to evaluate the extent to which SA for a clinical data set correlates with observed SA, or to evaluate the extent to which post-operative refractions correlate with what is expected based on the clinical data. The Optimized Kernel Parameter can be related to LPF, and sigma can represent the diffusion coefficient.

Shape Induced SA

Figure 26:
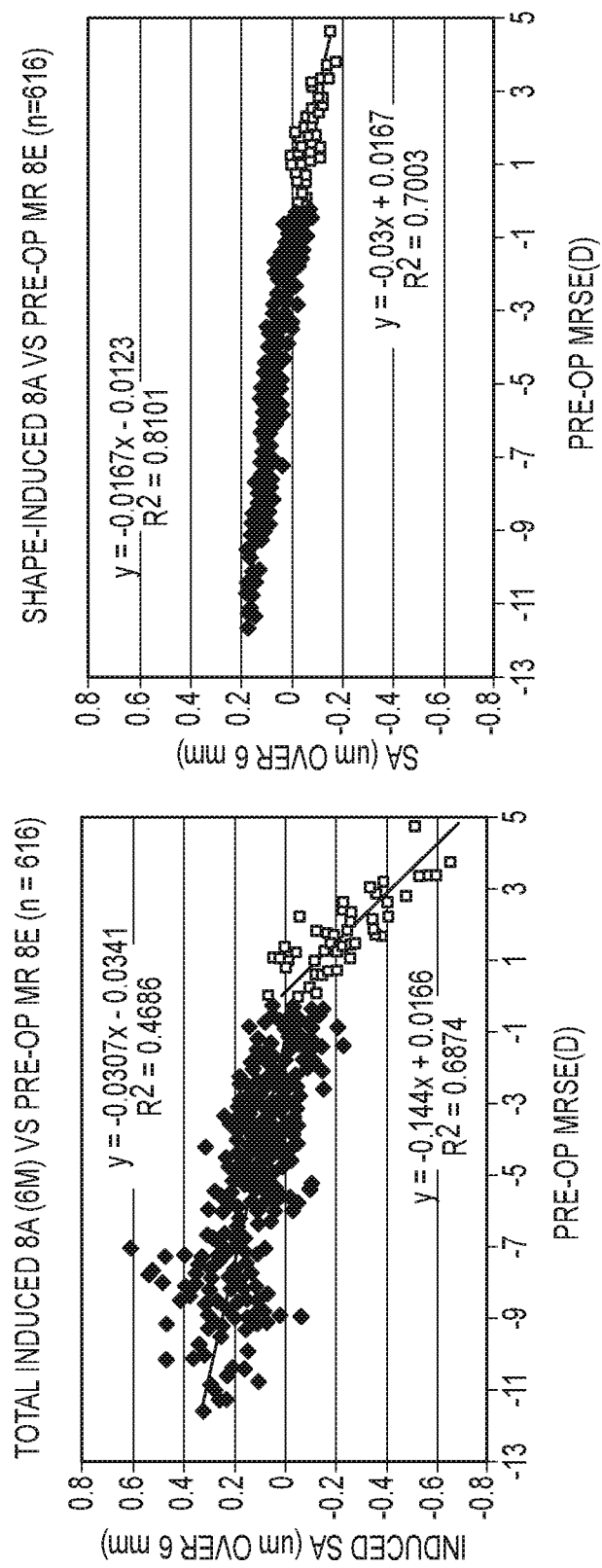
FIG. 26 shows aspects of induced SA according to embodiments of the present invention.

FIG. 26 shows a total induced SA (left panel, 0.188±0.139 for myopia and −0.110±0.179 for hyperopia) and a shape-induced SA (right panel, 0.064±0.049 for myopia and −0.071±0.038 for hyperopia) after taking into account a low-pass filtering effect, according to embodiments of the present invention. When considering the mean, it is possible to observe that shape-induced SA consists of ⅓ of the total SA for myopia and more than ½ for hyperopia. When considering the trend line slope, it is possible to observe that shape-induced SA consists of more than ½ for myopia and less than ¼ for hyperopia. Therefore, a shape-induced SA can be a significant component for an observed post-surgery spherical aberration. For the data presented in FIG. 26, the healing effect for the shape-induced SA was included in the simulation.

Low Pass Filter

Figure 27:
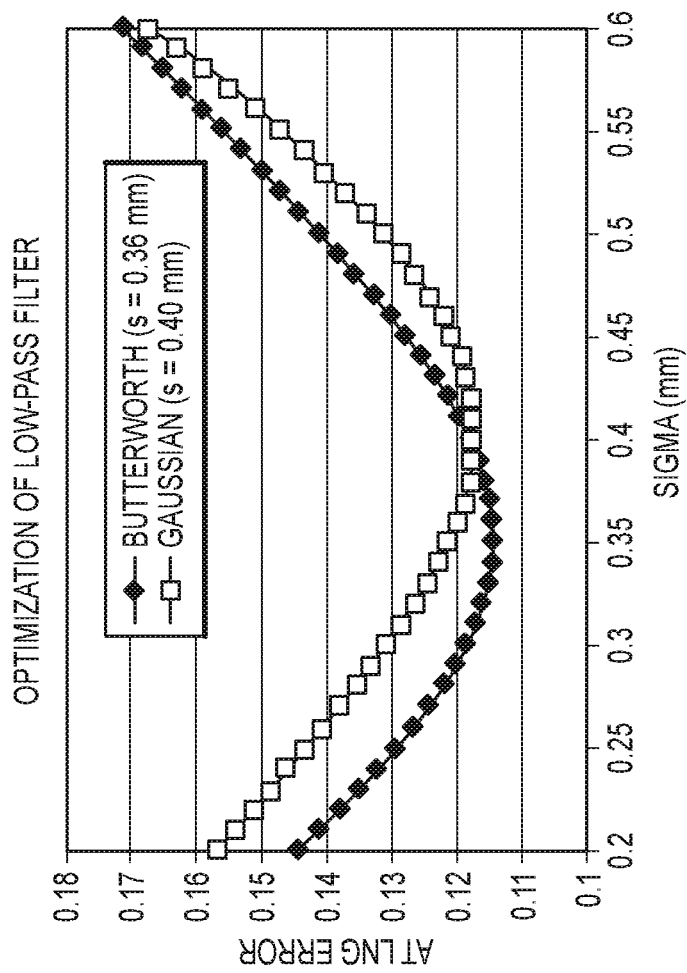
FIG. 27 illustrates aspects of low pass filter according to embodiments of the present invention.
Figure 28A:
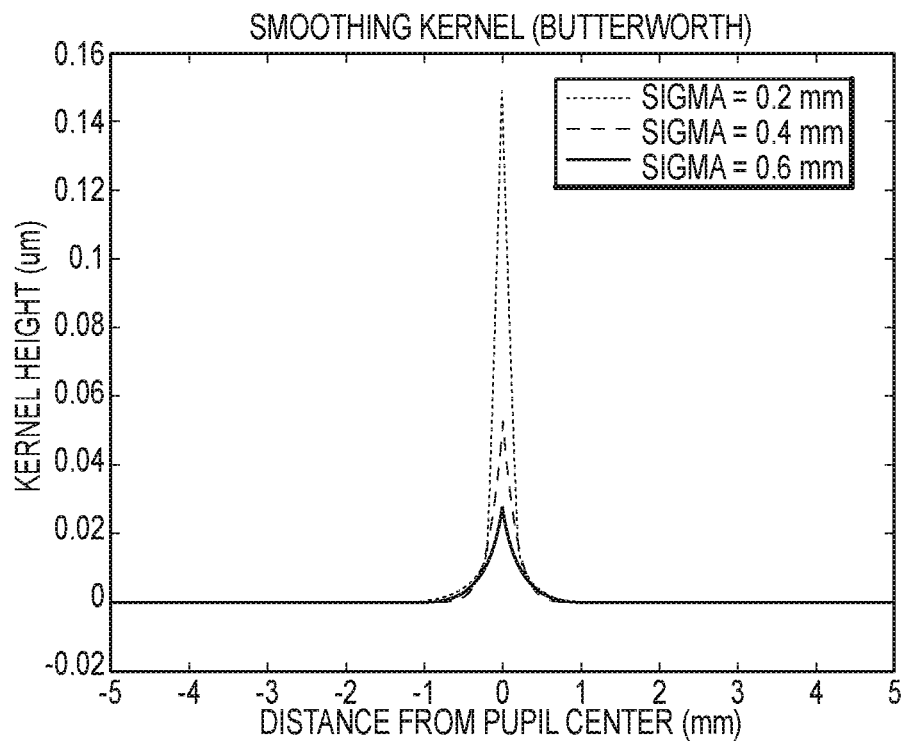
FIGS. 28A and 28B illustrate aspects of kernel and inverse kernel according to embodiments of the present invention.
Figure 28B:
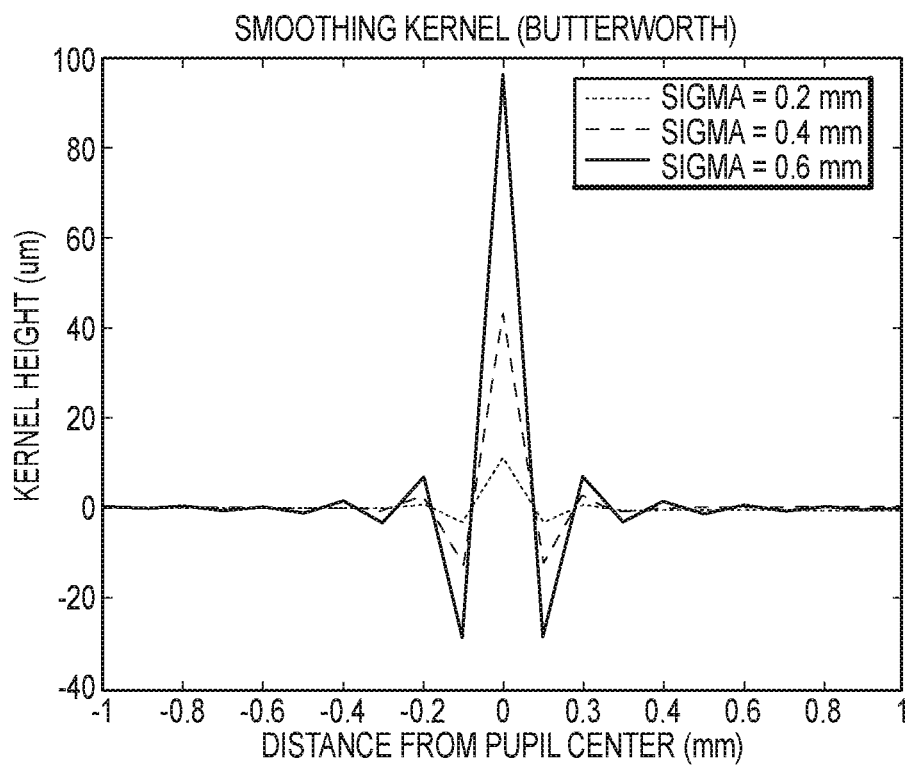

Assuming that a particular theoretical target shape provides a best fit for low order correction it is possible to perform an optimization as follows. First, an ablation target for an eye (e.g. an eye from a study) can be calculated according to a respective scaling factor and sphere adjustment. Second, a low pass filter (e.g. Butterworth or Gaussian) can be applied to obtain a healed shape. Third, a residual shape can be obtained by subtracting the healed shape from a pre-operative CV (CustomVue®) treatment shape. Fourth, a residual error in SA (e.g. predicted SA) can be calculated. Fifth, a merit function can be calculated. For example, the merit function may be the square root of the average sum of the square difference between the observed SA and the predicted SA. FIG. 27 shows aspects of optimization of a low pass filter, according to embodiments of the present invention. FIGS. 28A and 28B show aspects of a kernel and an inverse kernel, according to embodiments of the present invention.

Shape Deconvolution and Verification

Figure 29:
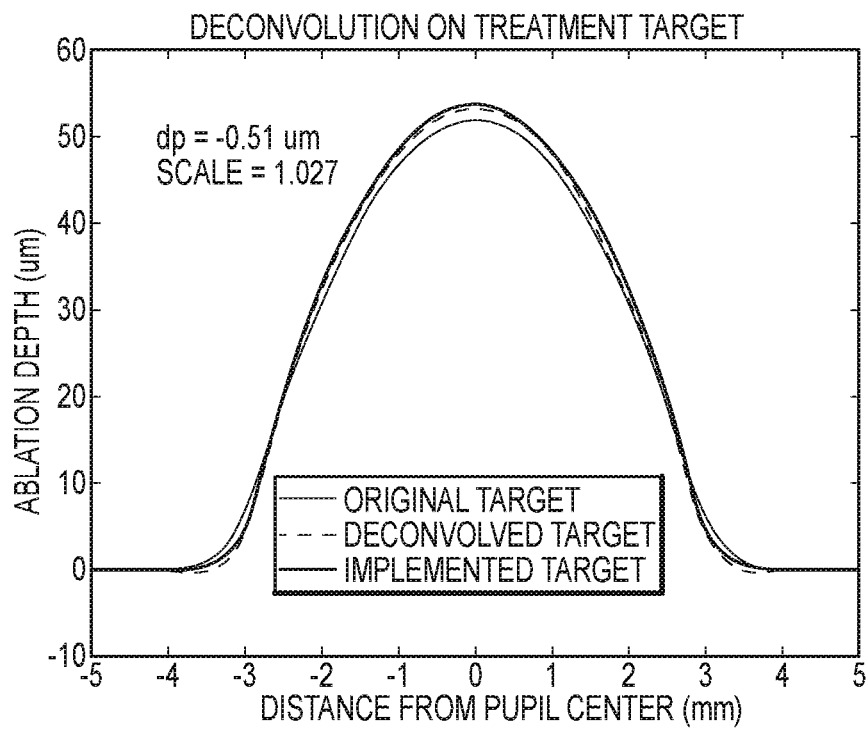
FIG. 29 illustrates aspects of treatment target deconvolution according to embodiments of the present invention.

According to some embodiments, it is possible to process a target shape as follows. First, a theoretical target is created, optionally using a zone-extended target algorithm. The target shape is then convolved with an inverse kernel. The convolved shape is them lifted to avoid negative ablation. A scaling factor can then be applied to preserved SE over a 4 mm zone. Subsequently, a cosine effect can be applied. FIG. 29 depicts aspects of a treatment target deconvolution according to embodiments of the present invention.

Figure 30:
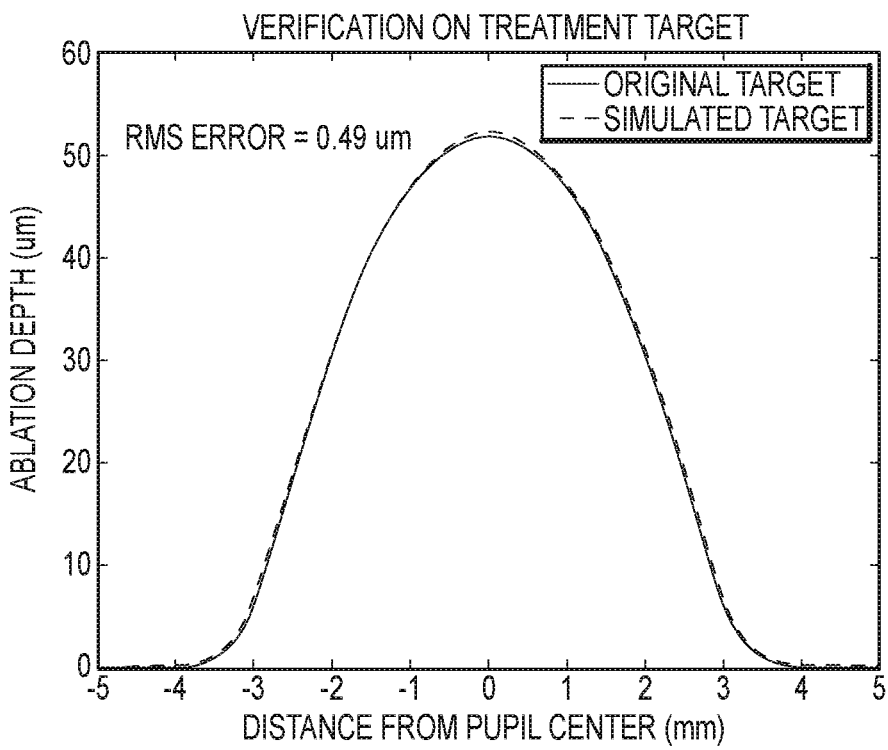
FIG. 30 depicts aspects of target verification according to embodiments of the present invention.
Figure 31A:
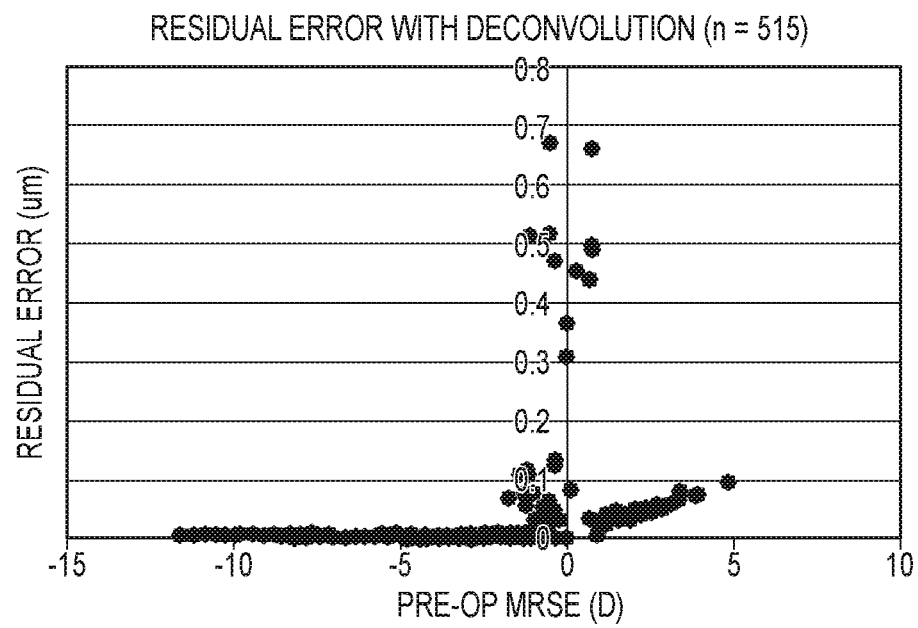
FIGS. 31A to 31C illustrate aspects of residual error with deconvolution according to embodiments of the present invention.
Figure 31B:
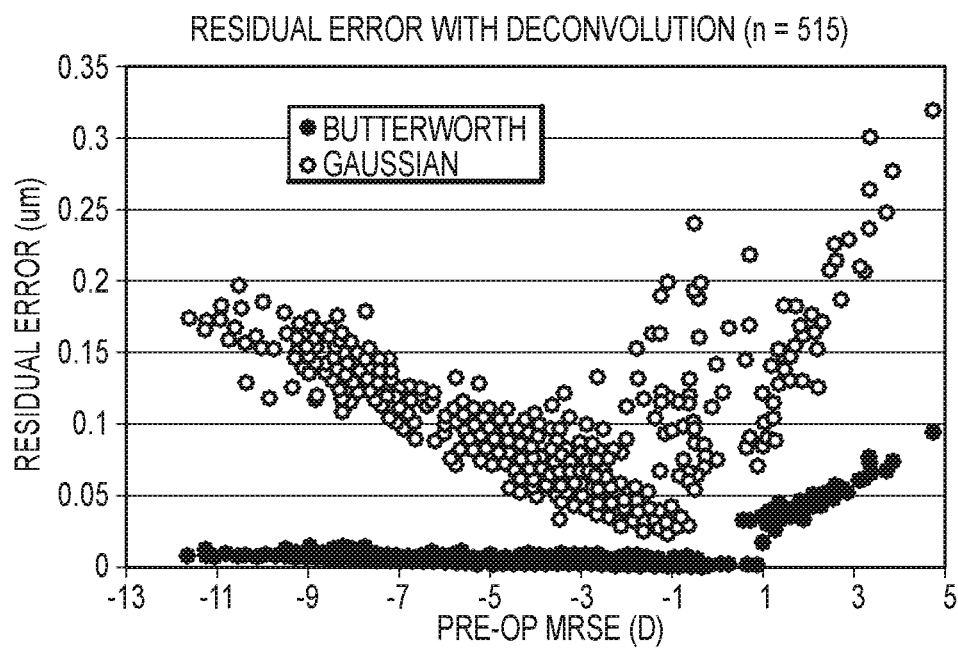
Figure 31C:
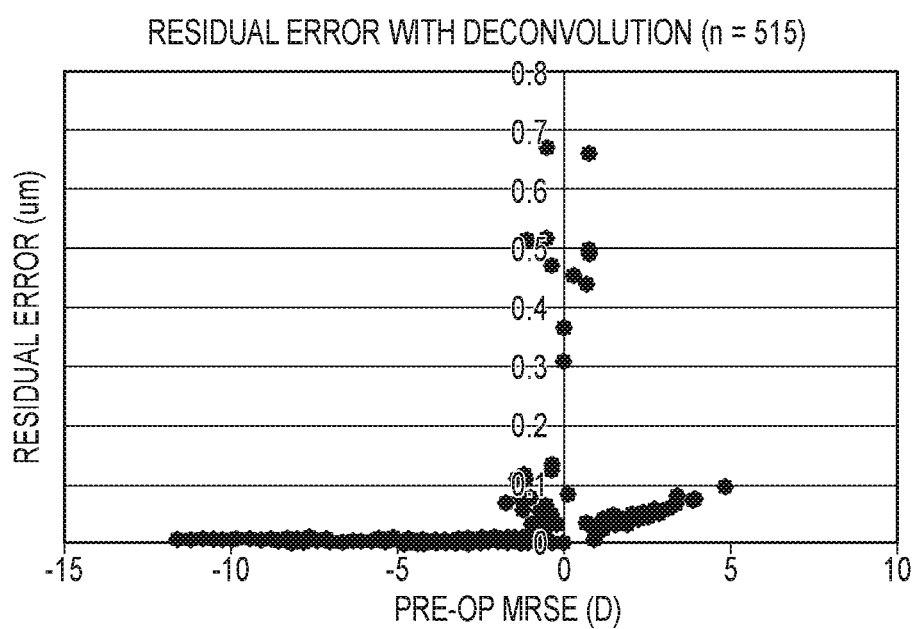

According to some embodiments, it is possible to verify such target shape procedures as follows. First, obtain a theoretical target shape for an eye (e.g. each eye from a study set). Second, obtain a deconvolved target by convolving the target shape with an inverse kernel. Third, convolve the target with a determined kernel (e.g. healed target). Fourth, calculate the difference between the theoretical target and the simulated healed target (e.g. healed target subtracted from theoretical target). FIG. 30 depicts aspects of a target verification procedure according to embodiments of the present invention. FIGS. 31A, 31B, and 31C depict residual error with deconvolution, according to embodiments of the present invention.

Figure 32C:
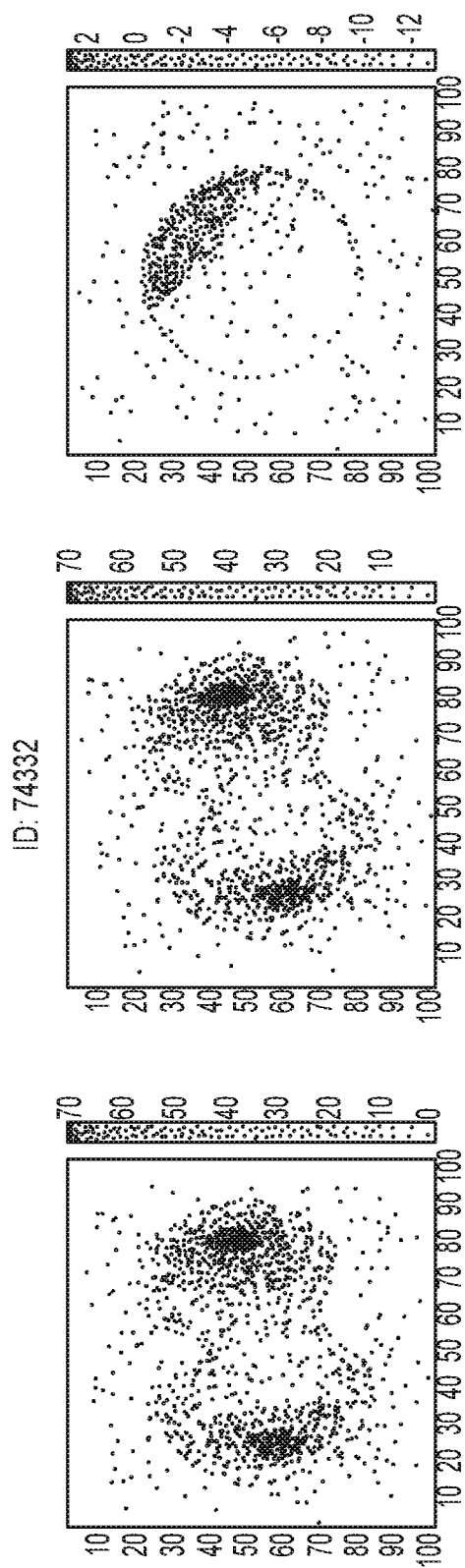

FIGS. 32A-32C depicts expected targets (left column), inversed convolved targets (middle column), and the difference between expected and inversed convolved targets (right column), according to embodiments of the present invention.

Optimization of Kernel

Figure 33:
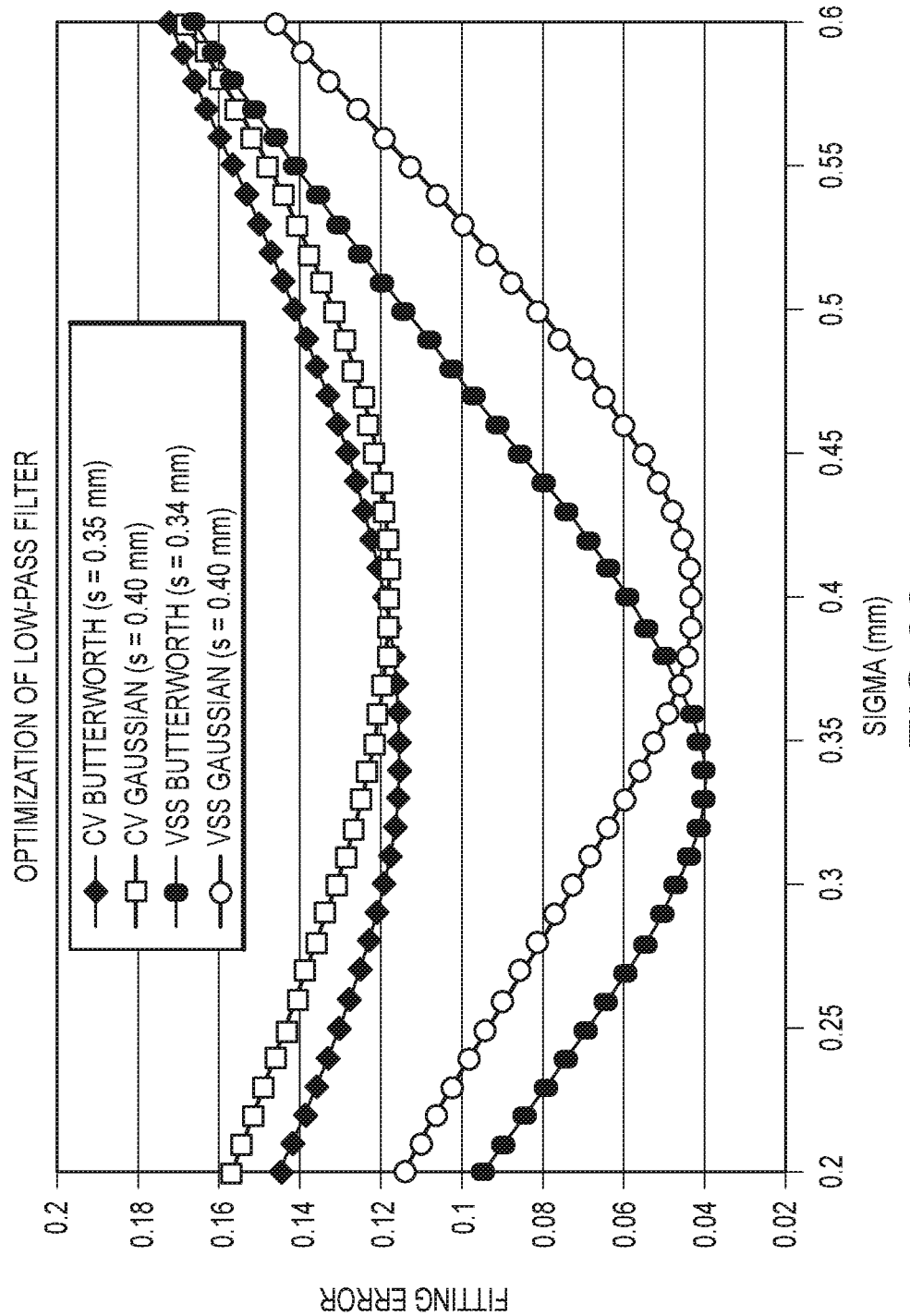
FIG. 33 illustrates aspects of low pass filter according to embodiments of the present invention.

FIG. 33 depicts CV data from a study (515 eyes, including myopia, hyperopia, high myopia, and mixed cases, as well as VSSR™ treatment data from a Canadian study (77 eyes, including myopia [mostly], and a few hyperopia and mixed cases). FIG. 33 indicates that the optimized sigma for various data sets suggests a range between about 0.33 mm and about 0.40 mm.

Post-Operative SA (Expected vs. Actual)

Figure 34:
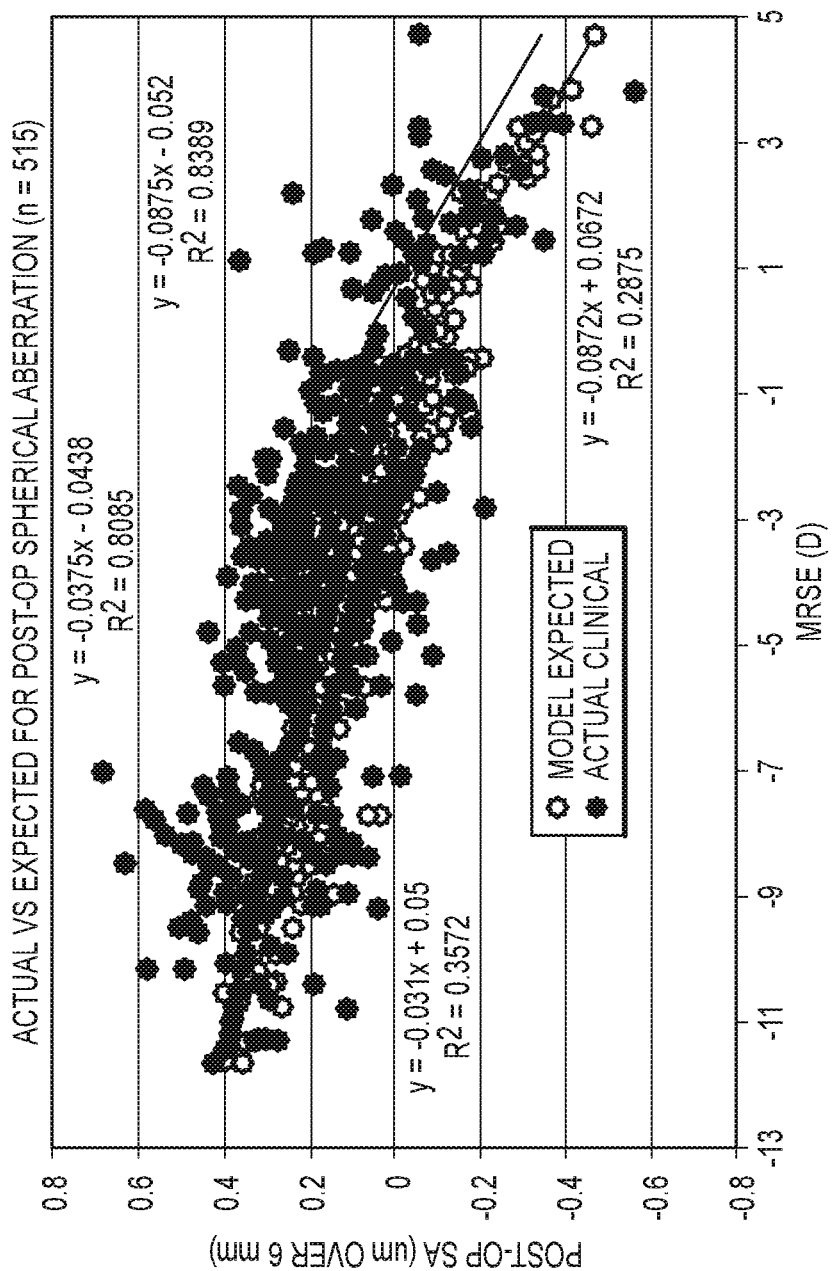
FIG. 34 illustrates aspects of post-operative SA according to embodiments of the present invention.

FIG. 34 depicts actual vs. expected post-operative spherical aberrations.

Other Features

Figure 35C:
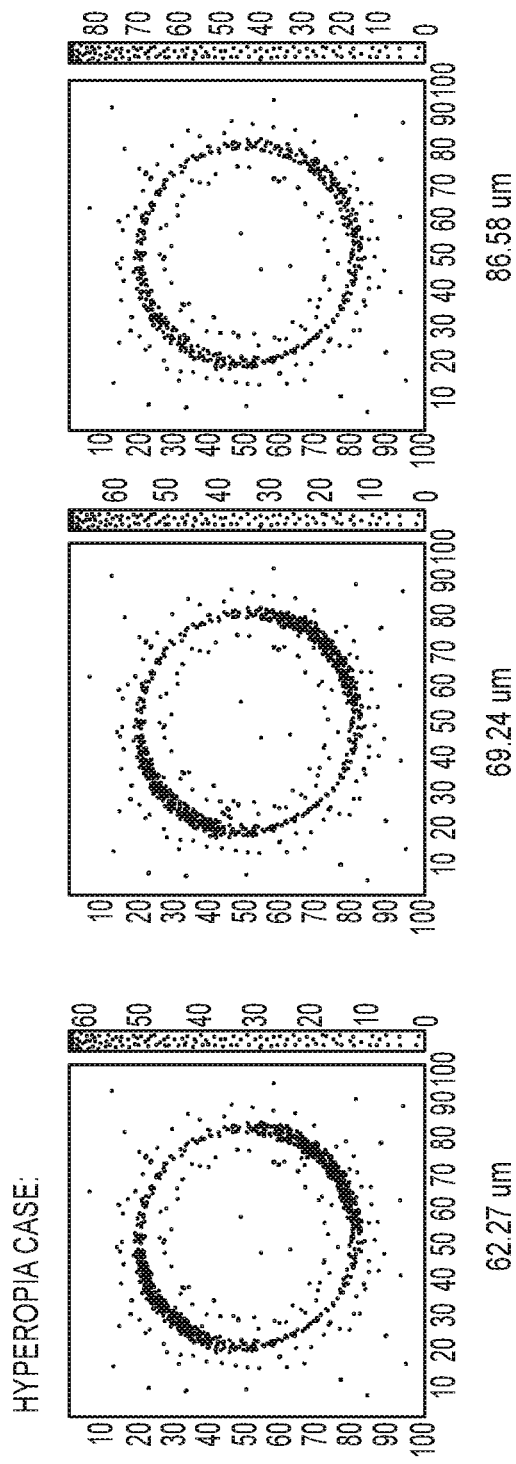

FIGS. 35A-35C depicts cylinder like cases, mixed cases, and hyperopia cases, respectively, according to embodiments of the present invention.

Dual Scale Kernel Techniques

Embodiments of the present invention encompass systems and methods which implement dual scale kernel techniques, triple scale kernel techniques, and other multi-scale kernel techniques. In some cases, embodiments of the present invention encompass multi-scale processes that account for corneal healing. Exemplary embodiments encompass filters having multiple parameters (e.g. dual scale filters) that can be developed by comparing simulated and observed data.

Laser vision correction is a rapidly growing field for correcting nearsightedness, farsightedness as well as astigmatism with dominating laser-assisted in situ keratomileusis (LASIK) procedures. Such techniques works well for correcting spherocylindrical aberrations, although there may be challenges with sufficiently correcting high order aberrations (HOAs), in particular spherical aberration (SA), due to induction of HOAs post-surgery. Embodiments of the present invention encompass systems and methods involving dual-scale linear filtering kernels (and other multi-scale approaches) that model or account for corneal epithelial remodeling as a source that accounts for HOA induction processes. As discussed herein, dual-scale kernels were developed based on several retrospective clinical data sets used as training data sets. In some cases, a downhill simplex algorithm can be used to develop two free parameters of the kernel. The performance of the kernel was tested on new clinical data sets that were not previously used for the development. Hence, embodiments of the present invention encompass systems and methods for generating linear filters that predict post-LASIK corneal smoothing, for example based on training data sets.

Historically, eyeglasses and contact lenses have been used to alleviate refractive problems such as nearsightedness, farsightedness, and astigmatism. With the advent of excimer lasers specially designed for laser-assisted in situ keratomeliusis (LASIK) and photorefractive keratectomy (PRK), patients have started to enjoy a new type of vision correction that is free of eyeglasses. With wavefront-guided LASIK, the correction of ocular aberrations is no longer limited to the so-called low-order aberrations, i.e., the spherocylindrical error that can be corrected with traditional eyeglasses. This technology enables the correction of higher-order aberrations (HOAs) that are beyond the spherocylindrical error, most notably spherical aberration and coma. Thus, super sharp vision can be targeted with the wavefront-guided LASIK.

LASIK often involves first cutting a flap on the corneal stroma, lifting it to the side, then delivering the UV laser pulses to remove tissue, and finally putting back the flap, which heals shortly after surgery. The precise design of an ablation target may cut the corneal stroma as needed to achieve a desired shape immediately after surgery. However, the biomechanical process and the corneal epithelial remodeling after surgery change the surface of the cornea, resulting in deviations from the original optical design of the ablation shape. The post-operative induction of HOAs, especially spherical aberration (SA), is currently among the most serious challenges for laser vision correction technology. It has been discovered that post-operative cornea remodeling can be a root cause of SA induction. One main effect of the cornea remodeling is the smoothing of epithelial anterior surface, when the epithelium tends to grow thicker at the center and fill in the dips of the cornea surface, created by refractive surgery. The epithelial smoothing can cause some spherocylindrical regression after refractive surgery, which can be corrected by a linear adjustment of the intended refractive correction. It can also lead to the induction of high-order aberrations, which can be increasingly strong for high myopia and hyperopia cases.

Figure 36:
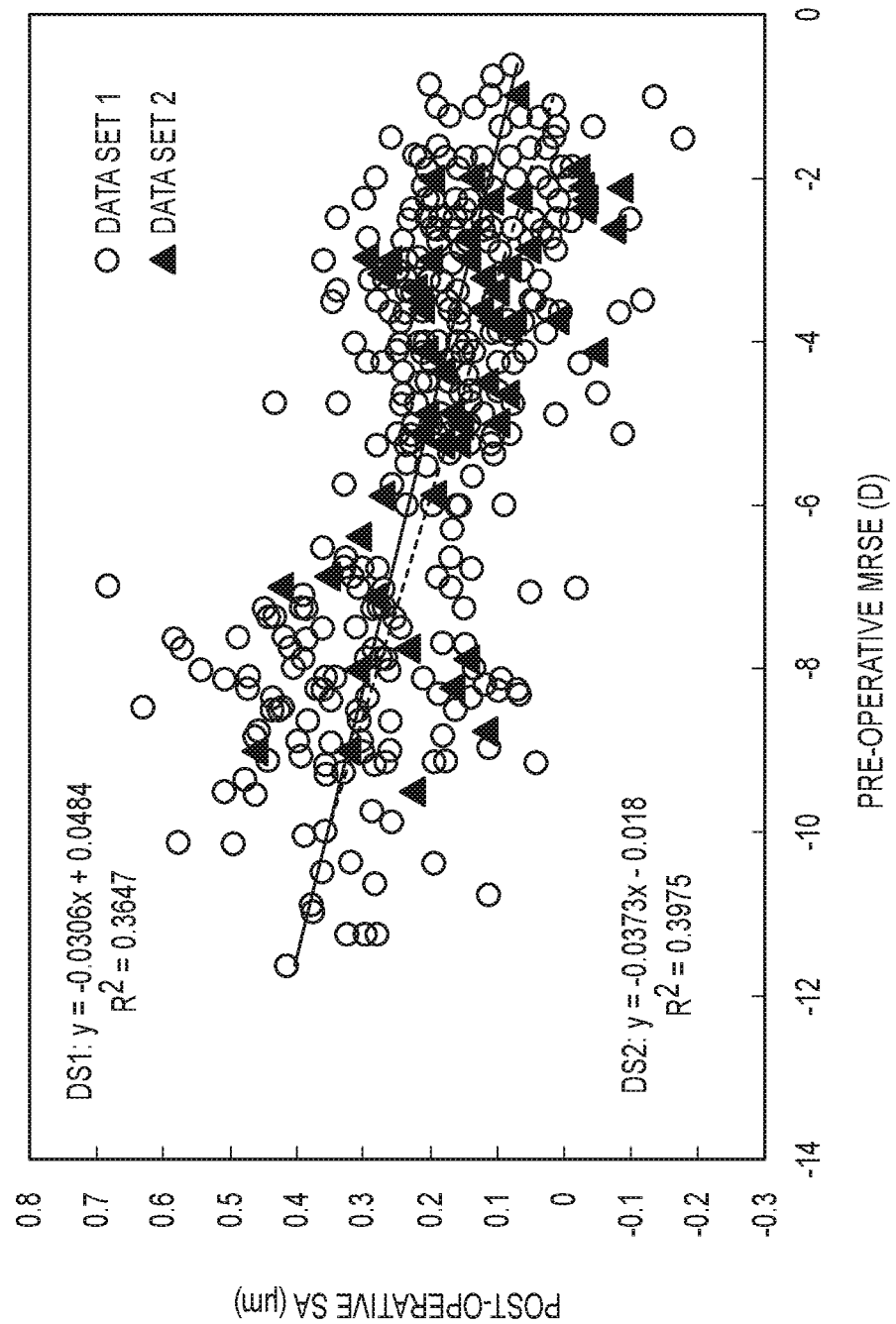
FIG. 36 depicts post-operative SA as a function of pre-operative manifest refraction according to embodiments of the present invention.

In general, the amount of the SA induction tends to increase with post-surgery time. Several months after surgery when the cornea stabilizes, the induced SA shows statistically significant trend versus the magnitude of the treated refraction. FIG. 36 shows the post-operative SA over a 6 mm diameter as a function of the pre-operative manifest refraction in spherical equivalent (MRSE). The regression slope of the induction is remarkably consistent between different data sets. This graph depicts post-LASIK spherical aberration (SA) as a function of the pre-operative manifest refraction in spherical equivalent (MRSE) for two data sets.

Embodiments of the present invention involve the development of corneal smoothing techniques that represent the corneal change post-surgery, for example based on retrospectively available clinical data. Exemplary kernels can be tested with other clinical data sets that were not previously used for the development. Such kernels can then be used to "reverse" the biological corneal smoothing effect by a mathematical deconvolution process. Vision treatments can be designed so as to reduce or avoid induced spherical aberration.

Figure 37:
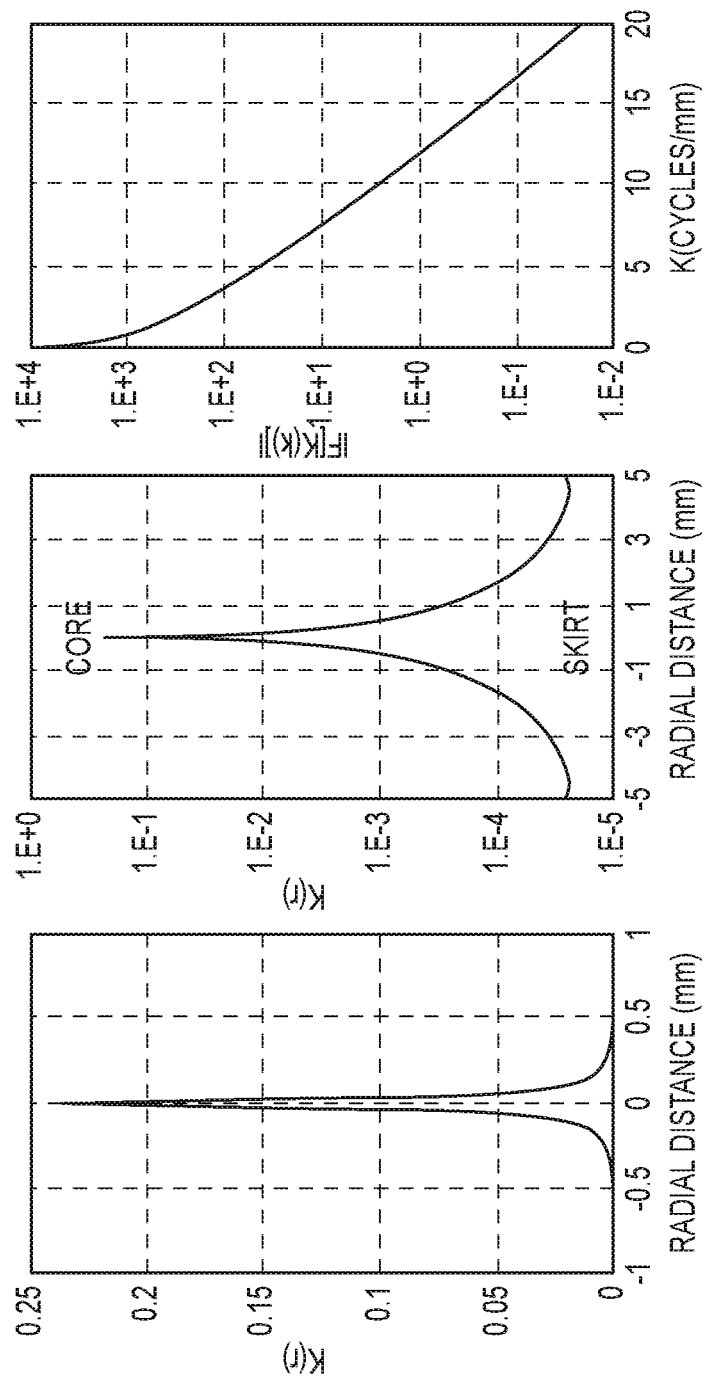
FIG. 37 shows aspects of kernels according to embodiments of the present invention.

Various techniques can be used to capture geometric changes to the surface of the human cornea occurring after the surgery (e.g. post-operative corneal smoothing). For example, a linear filter (LF) technique can be used to describe post-operative smoothing of the corneal ablation. Such techniques can be characterized by a small set of parameters determined by a filter development process based on retrospective clinical data. According to some embodiments, the post-operative epithelial smoothing process can be simulated by a technique that defines the shape of the post-operative cornea surface as a convolution of the ablation target profile with a linear smoothing filter as:

$$h_{post-op} = h_{pre-op} - K(x,y) \otimes T(x,y) \quad \text{Equation 23}$$

where h stands for the elevation maps of the corneal surface for pre-operative and post-operative situations, respectively, $\otimes$ denotes a convolution operation, $T(x, y)$ is the ablation target profile and $K(x, y)$ is the linear smoothing filter kernel. A squared Butterworth filter of the first order can take a form with the square term of the spatial frequency as:

$$K(k_x, k_y) = \frac{1}{1 + \frac{k_r^2}{s^2}} \quad \text{Equation 24}$$

where $K(k_x, k_y)$ is the Fourier transform of $K(x, y)$, $k_r = \sqrt{k_x^2 + k_y^2}$, and s is a parameter representing the scale of the kernel. The term $k_r^2$ can be represented as $k_x^2 + k_y^2$. Eq. (24) is in the Fourier domain. Embodiments of the present invention also encompass dual-scale and triple-scale linear filters that may have a somewhat similar shape as a squared Butterworth filter. According to some embodiments, various tests show that a dual-scale linear filter technique has the advantage of fast convergence and proper account of biological change of the epithelial tissue. For example, a dual-scale or dual parameter linear filter kernel can be defined as:

$$K(x, y) = \frac{1}{1 + \left[\frac{r}{s_2}\right]^2 - \left[\frac{r}{s_4}\right]^4} \quad \text{Equation 25}$$

where $r = \sqrt{x^2 + y^2}$ is the radial distance from the coordinate origin, $s_2$ and $s_4$ are two free parameters that can be determined. Eq. (25) is in the spatial domain. According to some embodiments, r, $s_2$ and $s_4$ all have dimensions in mm. Here, the power expansion is in the denominator. According to some embodiments, this can be considered as an inverse of a power expansion. FIG. 37 shows the cross-section of such a kernel and its power spectrum. As depicted here, the left panel provides a linear scale of the center of the kernel, the middle panel provides a logarithmic scale of the entire kernel, and the right panel provides a power spectrum of the kernel (e.g. in Fourier domain). As shown in the middle panel, the profile provides a sharp core and a wide skirt or wings.

By using Eq. (25) in Eq. (23) using the pre-operative and post-operative wavefront data as well as the treatment targets for various previously treated eyes, the two kernel parameters $s_2$ and $s_4$ can be obtained by minimizing the difference between the simulated post-operative wavefront error and the observed post-operative wavefront error. This minimization is a least-squares type which minimizes the regression slopes of the post-operative spherical equivalent (SE) and post-operative SA as a function of the pre-operative SE for all eyes as:

$$\sigma^2 = \sum \left[ \left( \frac{slopeSE_{simu} - slopeSE_{obs}}{\delta[slopeSE_{obs}]} \right)^2 + \left( \frac{slopeSA_{simu} - slopeSA_{obs}}{\delta[slopeSA_{obs}]} \right)^2 \right] \quad \text{Equation 26}$$

where slopeSE and slopeSA are the regression slopes of the post-operative SE versus pre-operative SE and post-operative SA versus pre-operative SE, respectively. $\delta$ stands for 95% confidence interval of the observed slope. Subscript "simu" stands for simulation and subscript "obs" stands for observation, i.e., clinical outcome. According to some embodiments, such a two scale technique can involve a short scale (e.g. that accounts for high order aberrations) and a long scale (e.g. the accounts for regression of lower order aberrations, or refraction). Hence, the short scale can relate to the SA term of Eq. (26) and the long scale can relate to the SE term of Eq. (26).

Several different development techniques have been tested. It has been discovered that a downhill simplex method works well in the context of this approach and the data sets. With four clinical data sets (two parts of Data Set 1, low myopia and high myopia, and Data Sets 3 and 5) used for development, it was found that $s_2 = 0.0334$ mm and $s_4 = 0.464$ mm give the minimum a as defined in Eq. (26). Hence, multi-scale kernel techniques, including such dual scale kernel techniques, can provide multi-parameter approaches that exhibit a good fit between data sets, which are in line with clinical observations or outcomes. For example, the $s_2$ and $s_4$ values of Eq. (25) as discussed herein can provide a good fit with clinical data.

Figure 38:
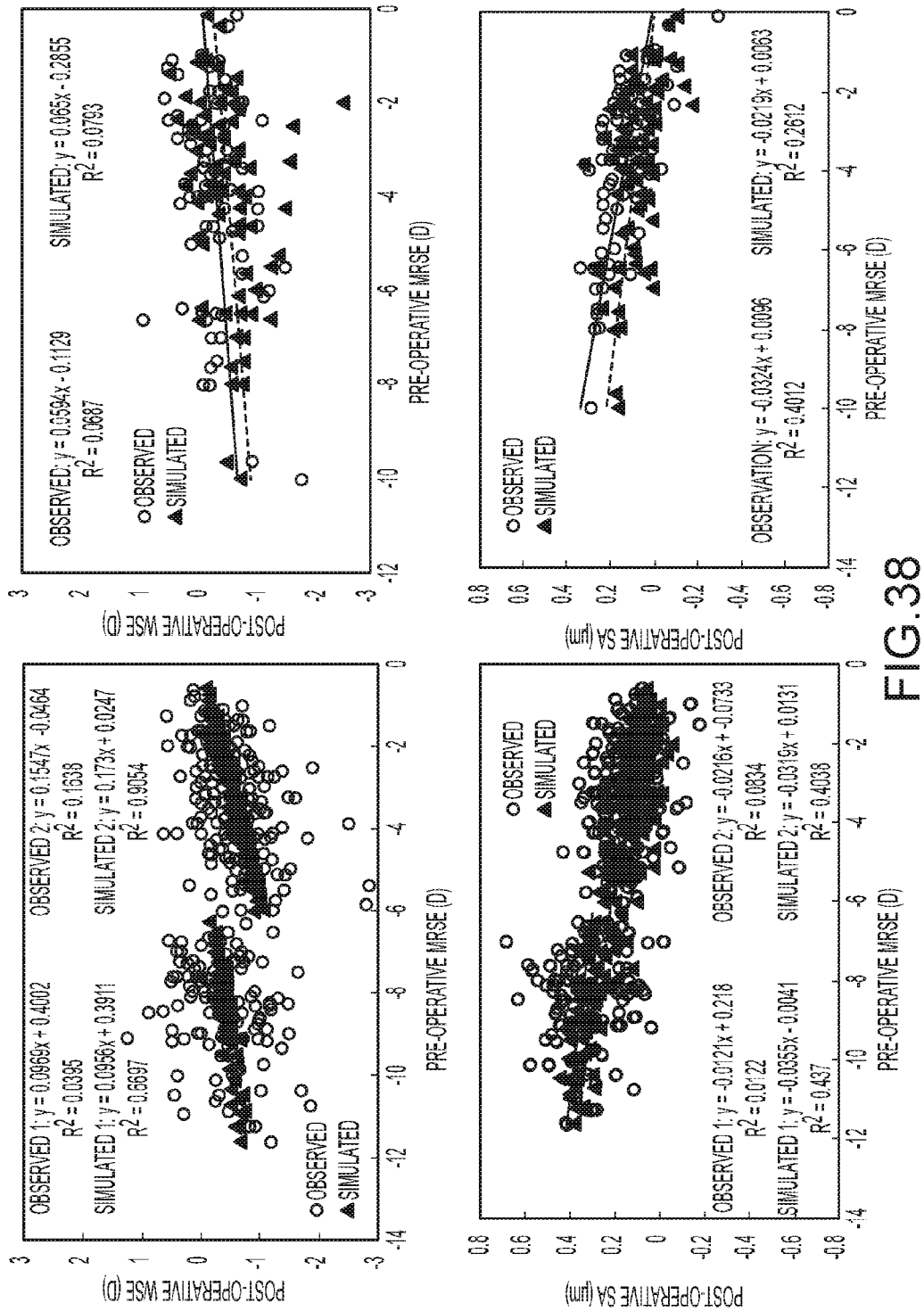
FIG. 38 provides comparisons between observed and simulated post-operative outcomes according to embodiments of the present invention.

With these two kernel parameters, application of the treatment parameters for those eyes using Eq. (23) makes it possible to obtain the simulated clinical outcome, which includes spherocylindrical error (wavefront spherical equivalent, or WSE) and SA. The WSE can be measured in diopters (D) and the SA can be measured in microns (μm) over a 6 mm diameter. FIG. 38 shows a comparison between the observed and simulated post-operative outcome for two data sets that were used for the development. Both the post-operative WSE and SA as a function of the pre-operative WRSE are plotted. It can be seen that the regression slopes of the simulated eyes agree well with those of the observed eyes. This comparison shows simulated and observed post-operative aberrations (WSE and SA) for Data Set 1 (left panels, two subsets, n=390) and Data Set 3 (right panels, n=76).

Once the parameters $s_2$ and $s_4$ are determined, the linear filter kernel can be determined based on Eq. (25). To obtain a new target shape that is capable of removing the post-operative induction of spherical aberration, a deconvolution process of Eq. (23) can be employed as:

$$T_{new} = K_{INV} \otimes T_{current} = F\left[\frac{[K(k_x, k_y)]^*}{[K(k_x, k_y)]^2 + SNR^2}\right] \otimes T_{current} \quad \text{Equation 27}$$

where F(•) stands for a Fourier transform, * denotes a complex conjugate, $T_{current}$ is the current treatment target with induction of post-operative SA, $T_{new}$ is the new target that is expected to remove the post-operative SA, and $K_{INV}$ is the inverse kernel of K(x,y). According to some embodiments, this approach can involve a Wiener filtering technique. The SNR can be used to prevent noise amplification and oscillation at the edge. A value of 0.1 can be used for practical purposes.

The effect of post-LASIK central corneal thickening caused by epithelial smoothing can provide at least partial explanation for regression after refractive surgery for myopia. Linear filter embodiments as disclosed herein can reflect a central corneal thickening phenomena, which gives biological support of the kernel.

Figure 39:
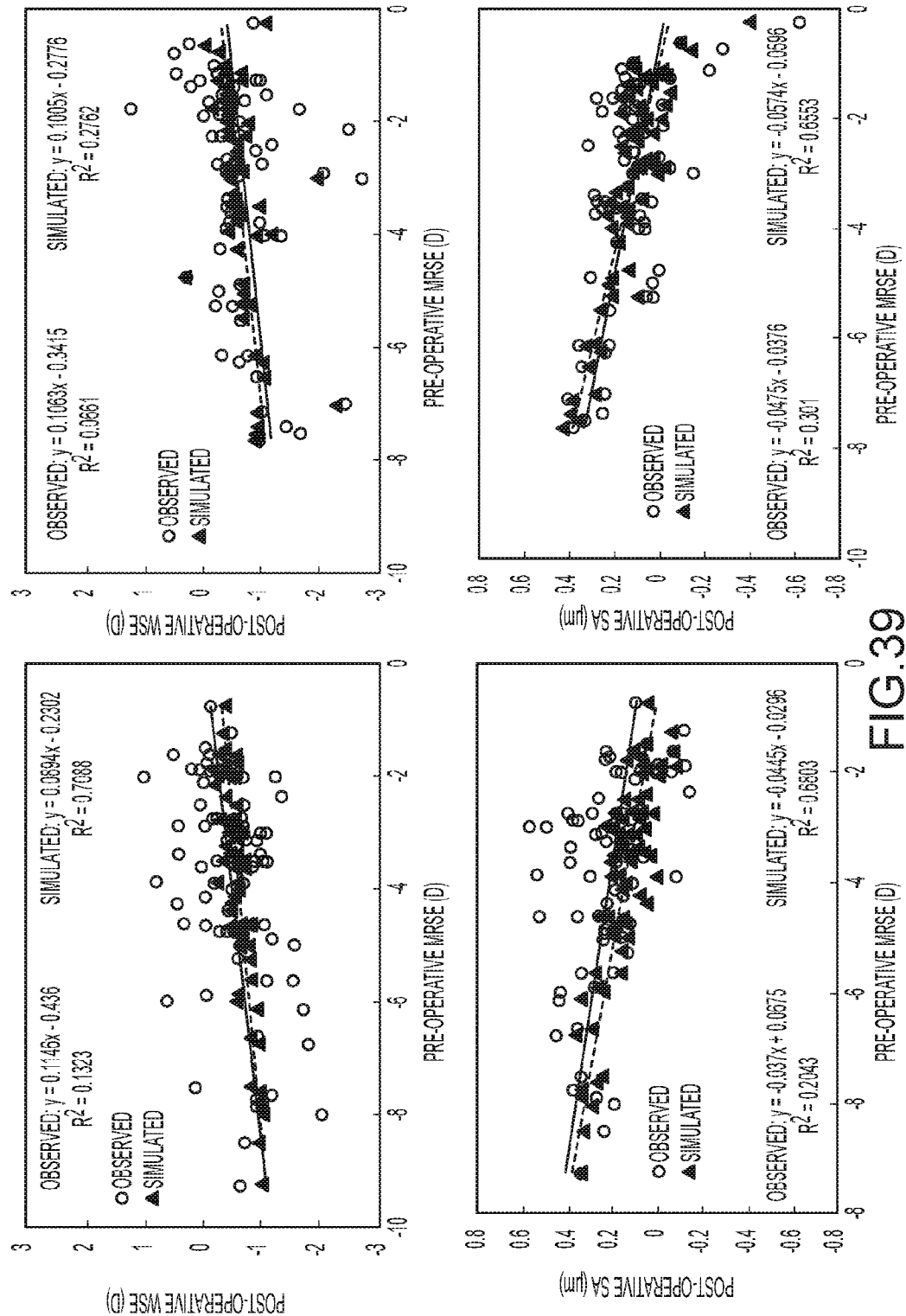
FIG. 39 provides comparisons between observed and simulated post-operative outcomes according to embodiments of the present invention.

In one verification approach using new test data, a kernel developed with Data Sets 1, 3 and 5 was applied to Data Sets 2 and 4, as depicted in FIG. 39. Specifically, this figure provides a comparison of simulated and observed post-operative aberrations (WSE and SA) for Data Set 2 (left panels, n=74) and Data Set 4 (right panels, n=72). As shown here, the regression slopes of the simulated eyes agree well with those of the observed eyes, even though these data sets were not used for the development. This result is consistent because the technique is intended to simulate the post-operative corneal smoothing process, which should not be different for different data sets.

Figure 40:
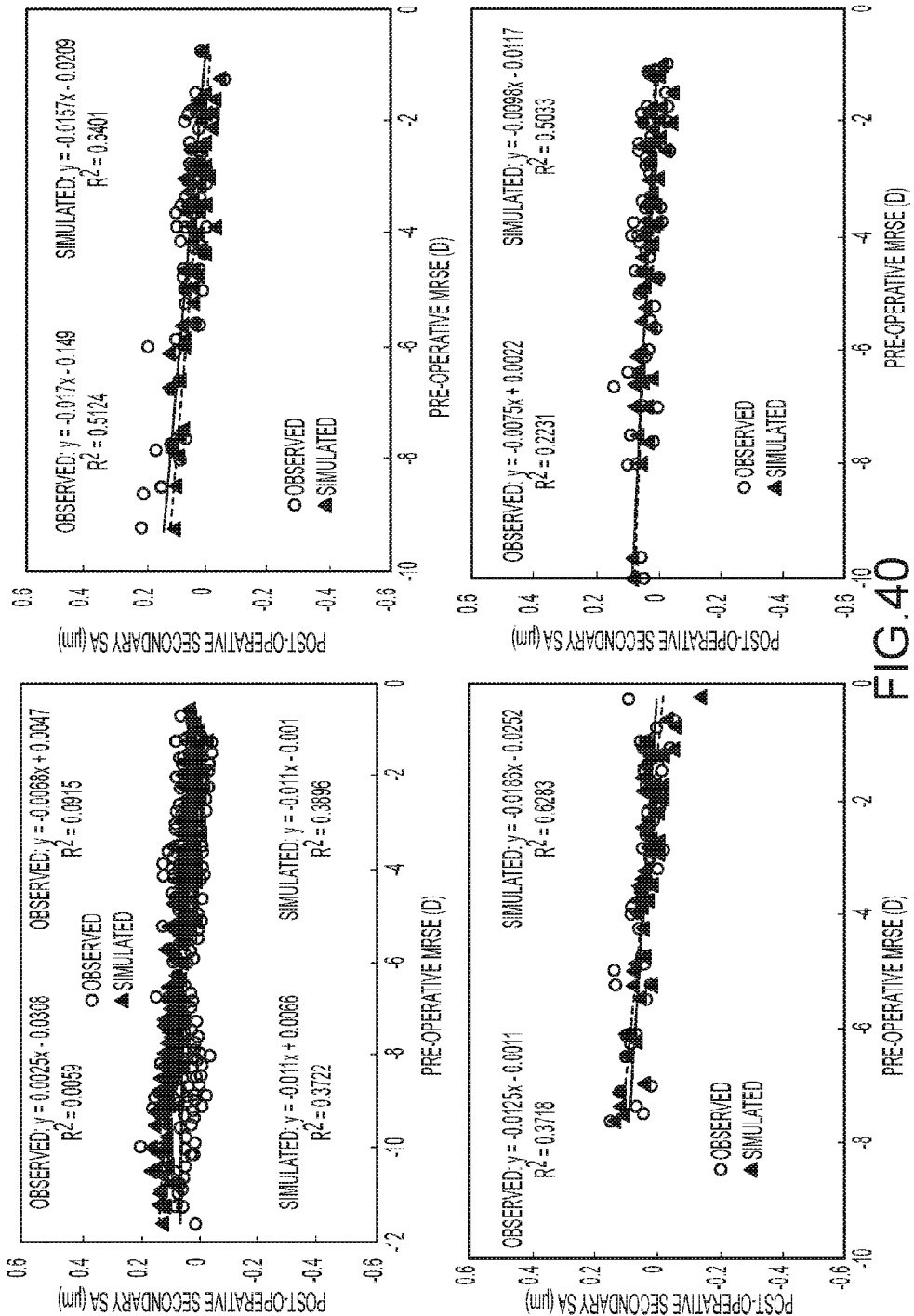
FIG. 40 provides comparisons between observed and simulated post-operative outcomes according to embodiments of the present invention.

Another verification approach was employed, with reference to the use of SE and SA as two aberration parameters for development in Eq. (26). The same kernel was used to obtain similar regression slopes for the secondary spherical aberration, which is not a parameter used in the development, as shown in FIG. 40. Here, post-operative secondary SA is depicted as a function of the pre-operative SE for simulated and observed eyes in the Data Set 1 (upper left, n=390), Data Set 2 (upper right, n=74), Data Set 3 (lower left, n=76), and Data Set 4 (lower right, n=76). All eyes are myopic. Good matches can be seen between the observed and the simulated slopes. This result is consistent, as the induction of HOAs from the corneal smoothing can be primarily rotationally symmetric. Secondary spherical aberration is an important rotationally symmetric aberration, in addition to sphere and primary spherical aberrations.

Some regression plots show a constant offset between the simulated and the observed trend lines. These offsets for post-operative SE or SA trend are about the same for all pre-operative MRSE values, indicating that they do not depend on ablation depth. They may be resulted by the creation of the LASIK flap. Depending on the choice of microkeratome and individual surgeon technique, the flap-induced aberrations may differ from site to site or surgeon to surgeon.

Embodiments of the present invention encompass the use of a smoothing kernel to assess the post-operative induction of spherical aberration. Exemplary embodiments provide satisfactory fitting for the regression slopes for both post-operative low-order refraction and high order aberrations simultaneously. Development based on both refraction and spherical aberration can lead to diverged outcomes.

Linear filters as disclosed herein having two free parameters can approximate a dual-scale smoothing. With reference to the cross-section of the kernel in logarithmic scale in FIG. 37, the sharp core corresponds to the short scale diffusion process and the wide wings correspond to the long scale smoothing process. These two separated processes can be linked to the post-operative corneal change in low-order and high-order aberrations, respectively. Consequently, the linear filter can be considered to yield a good match for both low-order aberrations (WSE) and high order aberrations (SA) observed clinically. Furthermore, this match can be extended to different data sets and different aberration types (secondary spherical aberration).

Figure 41:
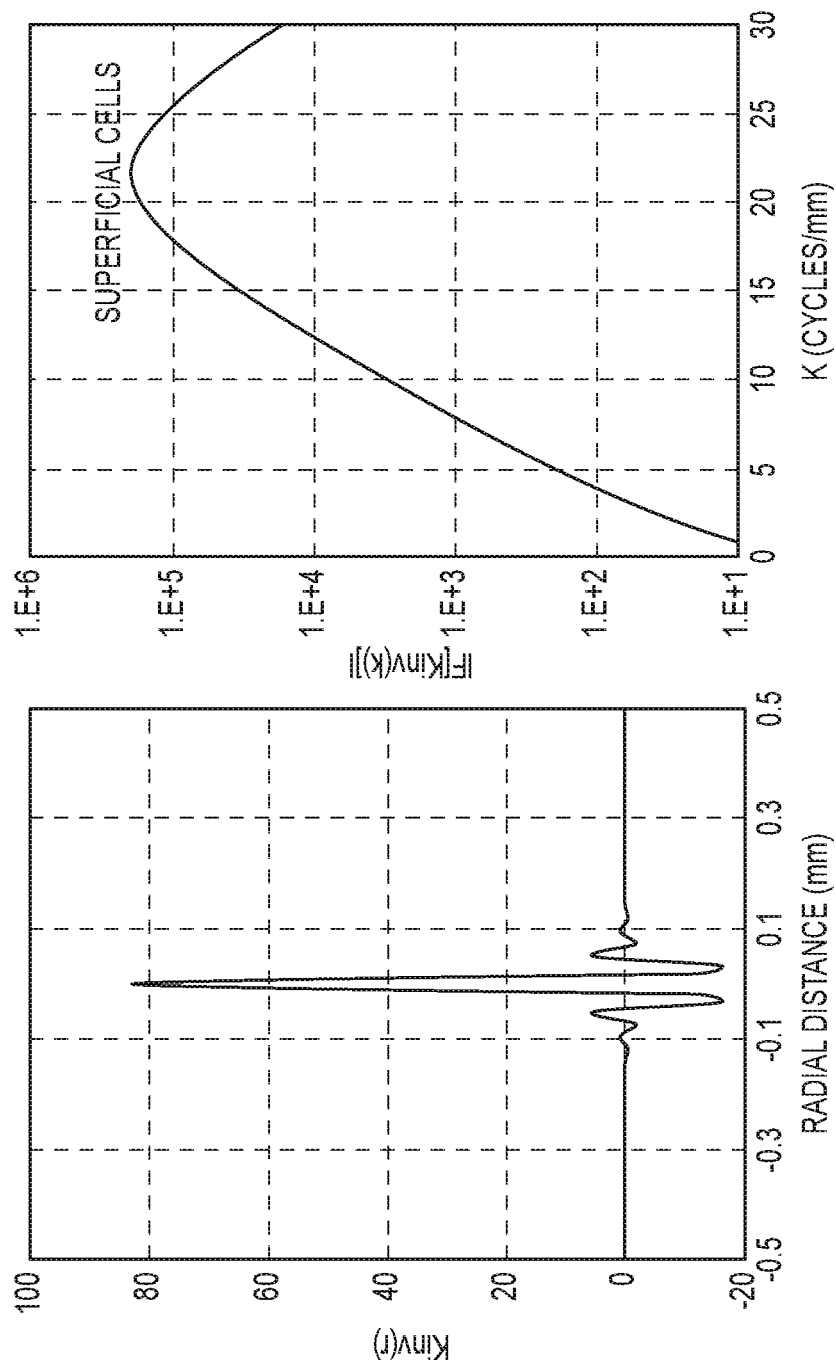
FIG. 41 depicts aspects of kernels according to embodiments of the present invention.

With reference to the inverse kernel $K_{INV}$, as depicted in FIG. 41, it can be seen that the peak of the power spectrum of the inverse kernel corresponds to the size of the superficial cells of the epithelium. As shown here, the cross-section of the inverse kernel of the linear filter is in the left panel (e.g. spatial domain), and the power spectrum of the inverse kernel is in the right panel (e.g. Fourier domain). Without being bound by any particular theory, it is believed that this relationship may be related to movement of the epithelial cells, especially the superficial cells, as attributed to the mechanism of the post-operative corneal smoothing. As the smoothing kernels generally smooth high curvature areas, the effect of the inverse kernel works in an opposite manner, sharpening areas that have high curvature changes. The link of the peak of the power spectrum of the inverse kernel to the size of the superficial cells of the epithelium can provide an additional level of confirmation for the kernel development process.

The epithelium of the eye often can have a depth of about 50 μm, representing five layers of cells. Individual superficial cells may have a height of about 5 μm and a diameter of about 20 μm. As depicted in the right panel of FIG. 41, the power spectrum peak can corresponds to the cell diameter (e.g. at about 20 cycles/mm).

As disclosed herein, it is possible to use certain combinations of data sets to develop a kernel, and certain other combinations of data sets to test or evaluate the kernel. A successful test of the developed kernel can lend strength to the usefulness of the kernel, which can be important when determining whether or how to proceed with costly clinical trials.

All patent filings, scientific journals, books, treatises, and other publications and materials discussed in this application are hereby incorporated by reference for all purposes. A variety of modifications are possible within the scope of the present invention. A variety of parameters, variables, factors, and the like can be incorporated into the exemplary method steps or system modules. While the specific embodiments have been described in some detail, by way of example and for clarity of understanding, a variety of adaptations, changes, and modifications will be obvious to those of skill in the art. Although the invention has been described with specific reference to a wavefront system using lenslets, other suitable wavefront systems that measure angles of light passing through the eye may be employed. For example, systems using the principles of ray tracing aberrometry, tscherning aberrometry, and dynamic skiascopy may be used with the current invention. The above systems are available from TRACEY Technologies of Bellaire, Tex., Wavelight of Erlangen, Germany, and Nidek, Inc. of Fremont, Calif., respectively. The invention may also be practiced with a spatially resolved refractometer as described in U.S. Pat. Nos. 6,099,125; 6,000,800; and 5,258,791, the full disclosures of which are incorporated herein by reference. Treatments that may benefit from the invention include intraocular lenses, contact lenses, spectacles and other surgical methods in addition to refractive laser corneal surgery.

Each of the calculations discussed herein may be performed using a computer or other processor having hardware, software, and/or firmware. The various method steps may be performed by modules, and the modules may comprise any of a wide variety of digital and/or analog data processing hardware and/or software arranged to perform the method steps described herein. The modules optionally comprising data processing hardware adapted to perform one or more of these steps by having appropriate machine programming code associated therewith, the modules for two or more steps (or portions of two or more steps) being integrated into a single processor board or separated into different processor boards in any of a wide variety of integrated and/or distributed processing architectures. These methods and systems will often employ a tangible media embodying machine-readable code with instructions for performing the method steps described above. Suitable tangible media may comprise a memory (including a volatile memory and/or a non-volatile memory), a storage media (such as a magnetic recording on a floppy disk, a hard disk, a tape, or the like; on an optical memory such as a CD, a CD-R/W, a CD-ROM, a DVD, or the like; or any other digital or analog storage media), or the like. While the exemplary embodiments have been described in some detail, by way of example and for clarity of understanding, those of skill in the art will recognize that a variety of modification, adaptations, and changes may be employed.

While the above provides a full and complete disclosure of exemplary embodiments of the present invention, various modifications, alternate constructions and equivalents may be employed as desired. Consequently, although the embodiments have been described in some detail, by way of example and for clarity of understanding, a variety of modifications, changes, and adaptations will be obvious to those of skill in the art. Accordingly, the above description and illustrations should not be construed as limiting the invention, which can be defined by the claims.

What is claimed is:

1. A method of determining a laser-ablation vision treatment plan for an eye of a patient, the method executed by a computer-based treatment-planning system, the method comprising:
   receiving, at an input of the treatment-planning system, an original target profile for the eye of the patient, the original target profile based on a desired cornea shape of the eye after the laser-ablation vision treatment;
   obtaining a spatial domain kernel filter that simulates post-operative corneal epithelial remodeling of the eye occurring after the laser-ablation vision treatment, wherein the spatial domain kernel filter is an inverse of a power expansion;
   convolving the original target profile with the spatial domain kernel filter to obtain a convolved target profile; and
   determining the laser-ablation vision treatment plan based on the convolved target profile.

2. The method of claim 1, wherein the power expansion is in spatial coordinates.

3. The method of claim 1, wherein the power expansion is a multi-parameter power expansion.

4. The method of claim 1, wherein the power expansion is a dual parameter power expansion.

5. The method of claim 1, wherein the power expansion is a triple parameter power expansion.

6. The method of claim 1, wherein the spatial domain kernel filter is based on a comparison between simulated post-operative wavefront error data and observed post-operative wavefront error data.

7. The method of claim 1, wherein the spatial domain kernel filter is based on a minimum value of σ, according to the equation $$\sigma^2 = \sum \left[ \left( \frac{slopeSE_{simu} - slopeSE_{obs}}{\delta[slopeSE_{obs}]} \right)^2 + \left( \frac{slopeSA_{simu} - slopeSA_{obs}}{\delta[slopeSA_{obs}]} \right)^2 \right]$$

wherein slopeSE and slopeSA are regression slopes of post-operative SE versus pre-operative SE and post-operative SA versus pre-operative SE, respectively, and wherein δ represents a 95% confidence interval of the respective slope.

8. The method of claim 1, wherein the spatial domain kernel filter is represented as K(x,y), and is characterized by the equation $$K(x, y) = \frac{1}{1 + \left[\frac{r}{s_2}\right]^2 - \left[\frac{r}{s_4}\right]^4}$$

wherein $r = \sqrt{x^2 + y^2}$ is a radial distance from a coordinate origin, and
wherein $s_2$ and $s_4$ are each free parameters.

9. A computer-based system for determining a laser-ablation vision treatment plan for an eye of a patient, the system comprising:
   an input configured to receive an original target profile for the eye of the patient, the original target profile based on a desired cornea shape of the eye after the laser-ablation vision treatment;
   a convolution module comprising a processor and a tangible non-transitory computer readable medium, the computer readable medium programmed with a computer application that, when executed by the processor, causes the processor to convolve the original target profile with a spatial domain kernel filter to obtain a convolved target profile, the spatial domain kernel filter simulating post-operative cornea remodeling of the eye occurring after the laser-ablation vision treatment, wherein the spatial domain kernel filter is an inverse of a power expansion; and
   a treatment planning module configured to determine the laser-ablation vision treatment plan based on the convolved target profile.

10. The computer-based system of claim 9, wherein the power expansion is in spatial coordinates.

11. The computer-based system of claim 9, wherein the power expansion is a multi-parameter power expansion.

12. The computer-based system of claim 9, wherein the power expansion is a dual parameter power expansion.

13. The computer-based system of claim 9, wherein the power expansion is a triple parameter power expansion.

14. The computer-based system of claim 9, wherein the spatial domain kernel filter is based on a comparison between simulated post-operative wavefront error data and observed post-operative wavefront error data.

15. The computer-based system of claim 9, wherein the spatial domain kernel filter is based on a minimum value of σ, according to the equation $$\sigma^2 = \sum \left[ \left( \frac{slopeSE_{simu} - slopeSE_{obs}}{\delta[slopeSE_{obs}]} \right)^2 + \left( \frac{slopeSA_{simu} - slopeSA_{obs}}{\delta[slopeSA_{obs}]} \right)^2 \right]$$

wherein slopeSE and slopeSA are regression slopes of post-operative SE versus pre-operative SE and post-operative SA versus pre-operative SE, respectively, and wherein δ represents a 95% confidence interval of the respective slope.

16. The computer-based system of claim 9, wherein the spatial domain kernel filter is represented as K(x,y), and is characterized by the equation $$K(x, y) = \frac{1}{1 + \left[\frac{r}{s_2}\right]^2 - \left[\frac{r}{s_4}\right]^4}$$

wherein $r = \sqrt{x^2 + y^2}$ is a radial distance from a coordinate origin, and wherein $s_2$ and $s_4$ are each free parameters.

17. A computer program product for determining a laser-ablation vision treatment plan for an eye of a patient, the computer program product embodied on a non-transitory tangible computer readable medium, the computer program product comprising:

computer code for receiving an original target profile for the eye of the patient, the original target profile based on a desired cornea shape of the eye after the laser-ablation vision treatment;

computer code for convolving the original target profile with a spatial domain kernel filter to obtain a convolved target profile, the spatial domain kernel filter simulating post-operative cornea remodeling of the eye occurring after the laser ablation vision treatment, wherein the spatial domain kernel filter is an inverse of a power expansion; and computer code for determining the laser-ablation vision treatment plan based on the convolved target profile.

18. The computer program product of claim 17, wherein the power expansion is in spatial coordinates.

19. The computer program product of claim 17, wherein the power expansion is a multi-parameter power expansion.

20. The computer program product of claim 17, wherein the power expansion is a dual parameter power expansion.

21. The computer program product of claim 17, wherein the power expansion is a triple parameter power expansion.

22. The computer program product of claim 17, wherein the spatial domain kernel filter is based on a minimum value of σ, according to the equation $$\sigma^2 = \sum \left[ \left( \frac{slopeSE_{simu} - slopeSE_{obs}}{\delta[slopeSE_{obs}]} \right)^2 + \left( \frac{slopeSA_{simu} - slopeSA_{obs}}{\delta[slopeSA_{obs}]} \right)^2 \right]$$

wherein slopeSE and slopeSA are regression slopes of post-operative SE versus pre-operative SE and post-operative SA versus pre-operative SE, respectively, and wherein δ represents a 95% confidence interval of the respective slope.

23. The computer program product of claim 17, wherein the spatial domain kernel filter is represented as K(x,y), and is characterized by the equation $$K(x, y) = \frac{1}{1 + \left[\frac{r}{s_2}\right]^2 - \left[\frac{r}{s_4}\right]^4}$$

wherein $r = \sqrt{x^2 + y^2}$ is a radial distance from a coordinate origin, and wherein $s_2$ and $s_4$ are each free parameters.

* * * * *